United States Patent [19]
Kuberasampath et al.

[11] Patent Number: 6,022,853
[45] Date of Patent: *Feb. 8, 2000

[54] MORPHOGEN-ENRICHED DIETARY COMPOSITION

[75] Inventors: Thangavel Kuberasampath; Charles M. Cohen, both of Medway; David C. Rueger, Hopkinton; Hermann Oppermann, Medway, all of Mass.; Roy H. L. Pang, Etna, N.H.

[73] Assignee: Creative BioMolecules, Inc., Boston, Mass.

[*] Notice: This patent is subject to a terminal disclaimer.

[21] Appl. No.: 08/278,730

[22] Filed: Jul. 20, 1994

Related U.S. Application Data

[63] Continuation of application No. 07/946,235, Sep. 16, 1992, abandoned, which is a continuation-in-part of application No. 07/922,813, Jul. 31, 1992, abandoned, application No. 07/923,780, Jul. 31, 1992, abandoned, application No. 07/938,336, Aug. 28, 1992, abandoned, application No. 07/938,337, Aug. 28, 1992, abandoned, and application No. 07/752,764, Aug. 30, 1991, abandoned, said application No. 07/922,813, is a continuation-in-part of application No. 07/752,764, Aug. 30, 1991, abandoned, which is a continuation-in-part of application No. 07/667,274, Mar. 11, 1991, abandoned, said application No. 07/923,780, is a continuation-in-part of application No. 07/752,857, Aug. 30, 1991, abandoned, which is a continuation-in-part of application No. 07/667,274, said application No. 07/938,336, is a continuation-in-part of application No. 07/753,059, Aug. 30, 1991, abandoned, which is a continuation-in-part of application No. 07/667,274, said application No. 07/938,337, is a continuation-in-part of application No. 07/753,059, Aug. 30, 1991, abandoned, which is a continuation-in-part of application No. 07/667,274, said application No. 07/752,764, is a continuation-in-part of application No. 07/667,274.

[51] Int. Cl.$^7$ .................................................. A61K 38/18

[52] U.S. Cl. ................................ 514/12; 514/2; 424/439; 424/464

[58] Field of Search ........................ 514/12; 424/439, 424/464; 426/657, 800, 801

[56] References Cited

U.S. PATENT DOCUMENTS

| | | |
|---|---|---|
| 3,626,069 | 12/1971 | Ott et al. .................................. 424/273 |
| 4,177,293 | 12/1979 | Formán et al. ........................... 424/43 |
| 4,418,091 | 11/1983 | Glas ......................................... 426/580 |
| 4,440,860 | 4/1984 | Klagsburn ............................. 435/240.3 |
| 4,466,958 | 8/1984 | Morrison ................................. 424/724 |
| 4,877,864 | 10/1989 | Wang et al. ............................... 514/12 |
| 4,968,590 | 11/1990 | Kuberasampath et al. ............. 530/326 |
| 4,975,526 | 12/1990 | Kuberasampath et al. ............. 530/350 |
| 4,994,442 | 2/1991 | Gil et al. .................................. 514/45 |
| 5,008,240 | 4/1991 | Bentz et al. ............................... 514/12 |
| 5,011,691 | 4/1991 | Oppermann et al. .................. 535/69.1 |
| 5,013,569 | 5/1991 | Rubin ...................................... 426/585 |
| 5,013,649 | 5/1991 | Wang et al. .......................... 530/387.2 |
| 5,066,500 | 11/1991 | Gil et al. .................................. 426/72 |
| 5,106,626 | 4/1992 | Parsons et al. ......................... 424/423 |
| 5,108,753 | 4/1992 | Kuberasampath et al. ............. 424/422 |
| 5,108,989 | 4/1992 | Amento et al. ........................... 514/12 |
| 5,141,905 | 8/1992 | Rosen et al. ........................... 435/69.1 |
| 5,169,666 | 12/1992 | Woychik .................................. 426/580 |
| 5,221,734 | 6/1993 | Bürk et al. ............................... 530/399 |

FOREIGN PATENT DOCUMENTS

| | | |
|---|---|---|
| 0148155 | 7/1985 | European Pat. Off. . |
| 0 295 009 | 12/1988 | European Pat. Off. . |
| 0 313 515 | 4/1989 | European Pat. Off. . |
| 0416578A2 | 3/1991 | European Pat. Off. . |
| 88/00205 | 1/1988 | WIPO . |
| 89/09787 | 10/1989 | WIPO . |
| 89/09788 | 10/1989 | WIPO . |
| 89/10409 | 11/1989 | WIPO . |
| 90/03733 | 4/1990 | WIPO . |

OTHER PUBLICATIONS

Letterio et al. Science 264:1936–1938, 1994.
Reinhardt. Annals od Allergy 53:597–601, 1984.
Rosen et al.; Wang et al.; and Wozney et al. (1988), 3 Abstracts *Calc. Tissue Int.* 42 (Suppl.): A35(136), A37(146, 147).
Rosen et al. (1989), "Purification and Molecular Cloning of a Novel Group of BMPS and Localization of BMP MRNA In Developing Bone," 20 *Connect. Tissue Res.* 1–4:313–319.
Wozney et al. (1990), "Bone Morphogenic Proteins," 1 *Prog. In Growth Factor Res.* 267–280.
Rosen et al.; Celeste et al. (1990), 2 Abstracts *J. Cell Biochem. Suppl.* 14 Part E, 004:33, 54:105.
Katagiri et al. (1990), "The Non–Osteogenic Mouse Pluripotent Cell Line, C3H10T1/2 is Induced to Differentiate Into Osteoblastic Cells by Recombinant Human Bone Morphogenetic Protein–2," 172 *Biochem. Biophys. Res.* 1:295–299.
Wozney et al. (1990), "Growth Factors Influencing Bone Development," 13 *J. Cell Sci. Suppl.* 149–156.
Takuwa et al. (1991), "Bone Morphogenetic Protein–2 Stimulates Alkaline Phosphatase Activity and Collagen Synthesis in Cultured Osteoblastic Cells, MC3T3–E1," 174 *Biochem. Biophys. Res. Comm.* 1:96–101.
Yamaguchi et al. (1991), "Recombinant Human Bone Morphogenetic Protein–2 Stimulates Osteoblastic Maturation and Inhibits Myogenic Differentiation In Vitro," 113 *J. Cell Biol.* 3:681–687.
D'Allesandro et al. (1991), Abstract Q–105 *J. Cell. Biochem.*
Israel et al. (1991), Abstract Q–111 *J. Cell. Biochem.*
Thies et al. (1992), "Recombinant Human Bone Morphogenetic Protein–2 Induces Osteoblastic Differentiation in W–20–17 Stromal Cells," 130 *Endocrinology* 3:1318–1324.
Wozney et al. (1992), "The Bone Morphogenetic Protein Family and Osteogenesis," 32 *Mol. Reprod. Dev.* 2:160–167.

(List continued on next page.)

*Primary Examiner*—Elizabeth Kemmerer
*Attorney, Agent, or Firm*—Ivor R. Elriff; Michael Morency; Mintz, Levin, Cohn, Ferris, Glovsky and Popeo, P.C.

[57] ABSTRACT

Disclosed are methods and compositions useful in dietary applications and capable of enhancing tissue morphogenesis, including tissue development and viability in a mammal, particularly a human. The methods and compositions include a morphogen which, when provided to an individual as a food formulation or supplement, is capable of enhancing tissue development and viability in the individual.

22 Claims, 9 Drawing Sheets

OTHER PUBLICATIONS

Rogers et al. (1992), "Bone Morphogenetic Proteins–2 and –4 are Involved In The Retinoic Acid–Induced Differentiation of Embryonal Carcinoma Cells," 3 *Mol. Biol. Cell* 2:189–196.

Wozney et al.; Celeste et al.; Rosen et al. (1992), Abstracts 76(WO26), 100(W502) and 103(W513) *J. Cell Biochem. Suppl.* 16 Part F.

Israel et al. (1992), "Expression and Characterization of Bone Morphogenetic Protein–2 in Chinese Hamster Ovary Cells," 7 *Growth Factors* 139–150.

Padgett et al. (1993), "Human BMP Sequences Can Confer Normal Dorsal–Ventral Patterning in the Drosophila Embryo," 90 *PNAS* 2905–2909.

AAP Committee on Nutrition, *Pediatrics*, 75:976–986 (1985).

Behringer et al., *Nature*, 345:167–170 (1990).

Cate et al., *Cell*, 45:685–698 (1986).

Celeste et al., *PNAS*, 87:9843–9847 (1990).

Chomczyaski et al., *Anal. Bioch.*, 162:156–159 (1987).

Edelman, *Ann. Rev. Cell. Biol.*, 2:81–116 (1986).

ESPGAN Committee of Nutrition, *Acta Paed. Scan. Suppl.*, 330:7–27 (1987).

Engvall, *Methods in Enzymology*, 70:419–439 (1980).

Green et al., *Nature*, 347:391–394 (1990).

Jin et al., *J. Protein Chemistry*, 10:565–575 (1991).

Kuberasampath et al., *J. Biol. Chem.*, 265:13198–13205 (1990).

Lee, *Molecular Endocrinology*, 4:1034–1040 (1990).

Lee, *PNAS*, 88:4250–4254 (1991).

Lyons et al., *PNAS*, 86:4554–4558 (1989).

Lyons et al., *Genes & Development*, 3:1657–1668 (1989).

Mason et al., *Nature*, 318:659–663 (1985).

Mason et al., *Mol. Endocrinology*, 3:1352–1358 (1989).

Miller et al., *Cancer Research*, 42:2589–3594 (1987).

Ozkaynak et al., *Embo J.*, 9:2085–2093 (1990).

Ozkaynak et al., *Biochem. Biophys. Res. Comm.*, 179:116–123 (1991).

Padgett et al., *Nature*, 325:81–84 (1987).

Panganiban et al., *Mol. and Cell. Biol.*, 10:2669–2677 (1990).

Sampath et al., *PNAS*, 80:6591–6595 (1983).

Schubert et al., *Nature*, 344:868–870 (1990).

Smith et al., *Nature*, 345:729–731 (1990).

Sokol et al., *Science*, 249:561–563 (1990).

Wang et al., *PNAS*, 87:2220–2224 (1990).

Wang et al., *PNAS*, 85:9484–9488 (1988).

Weeks, *Cell*, 51:861–867 (1987).

Wharton et al., *PNAS*, 88:9214–9218 (1991).

Wozney et al., *Science*, 242:1528–1534 (1988).

Yannas, *Angew. Chem. Int. Ed. Engl.*, 29:20–35 (1990).

Bowie et al. 1990. Science 247:1306–1310.

Gennaro (1990) Remington's Pharmaceutical Sciences (Mack Publishers, N.Y.).

Lefer et al. (1990) Science, vol. 249, pp. 61–64.

Massagué (1987) Cell, vol. 49, pp. 437–438.

Pepinsky et al. (1988) Journal of Biological Chemistry, vol. 263, pp. 18961–18964.

Berkow et al, *The Merck Manual*, $14^{th}$ ed., pp. 869–889 (1982).

//0

```
                           SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
          (A) LENGTH: 97 amino acids
          (B) TYPE: amino acid
          (C) STRANDEDNESS: single
          (D) TOPOLOGY: linear (ii) MOLECULE TYPE: protein (ix) FEATURE:
          (A) NAME/KEY: Protein
          (B) LOCATION: 1..97
          (D) OTHER INFORMATION: /label= GENERIC-SEQ-1
              /note= "EACH XAA INDICATES ONE OF THE 20 NATURALLY
              OCCURRING L-ISOMER, ALPHA-AMINO ACIDS, OR A DERIVATIVE
              THEREOF"

(xi) SEQUENCE DESCRIPTION: SEQ ID NO:1:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Cys Xaa Xaa Xaa Cys Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Cys Cys Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Cys Xaa Cys
                85                  90                  95

Xaa (2) INFORMATION FOR SEQ ID NO:2:

(i) SEQUENCE CHARACTERISTICS:
          (A) LENGTH: 97 amino acids
          (B) TYPE: amino acid
          (C) STRANDEDNESS: single
          (D) TOPOLOGY: linear (ii) MOLECULE TYPE: protein (ix) FEATURE:
          (A) NAME/KEY: Protein
          (B) LOCATION: 1..97
          (D) OTHER INFORMATION: /label= GENERIC-SEQ-2
```

/note= "EACH XAA INDICATES ONE OF THE 20 NATURALLY
OCCURING L-ISOMER, ALPHA-AMINO ACIDS, OR A DERIVATIVE
THEREOF"

(xi) SEQUENCE DESCRIPTION: SEQ ID NO:2:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Cys Xaa Xaa Xaa Cys Xaa Xaa Xaa
            20                  25                  30

Xaa Xaa Xaa Cys Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Cys Cys Xaa Xaa
    50                  55                  60

Xaa Xaa Xaa Xaa Xaa Xaa Xaa Xaa Xaa Xaa Xaa Xaa Xaa Xaa Xaa
65              70                  75                  80

Xaa Xaa Xaa Xaa Xaa Xaa Xaa Xaa Xaa Xaa Xaa Xaa Cys Xaa Cys
            85                  90                  95

Xaa (2) INFORMATION FOR SEQ ID NO:3:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= GENERIC-SEQ-3
            /note= "WHEREIN EACH XAA IS INDEPENDENTLY SELECTED FROM A
            GROUP OF ONE OR MORE SPECIFIED AMINO ACIDS AS DEFINED IN
            THE SPECIFICATION "

(xi) SEQUENCE DESCRIPTION: SEQ ID NO:3:

Leu Tyr Val Xaa Phe Xaa Xaa Xaa Gly Trp Xaa Xaa Trp Xaa Xaa Ala
1               5                   10                  15

Pro Xaa Gly Xaa Xaa Ala Xaa Tyr Cys Xaa Gly Xaa Cys Xaa Xaa Pro
            20                  25                  30

Xaa Xaa Xaa Xaa Xaa Xaa Xaa Xaa Asn His Ala Xaa Xaa Xaa Xaa Leu
        35                  40                  45

Xaa Xaa Xaa Xaa Xaa Xaa Xaa Xaa Xaa Xaa Xaa Cys Cys Xaa Pro
    50                  55                  60

Xaa Xaa Xaa Xaa Xaa Xaa Xaa Xaa Leu Xaa Xaa Xaa Xaa Xaa Xaa
65              70                  75                  80

Val Xaa Leu Xaa Xaa Xaa Xaa Xaa Met Xaa Val Xaa Xaa Cys Gly Cys
            85                  90                  95

Xaa (2) INFORMATION FOR SEQ ID NO:4:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:

(A) NAME/KEY: Protein
                    (B) LOCATION: 1..102
                    (D) OTHER INFORMATION: /label= GENERIC-SEQ-4
                         /note= "WHEREIN EACH XAA IS INDEPENDENTLY SELECTED FROM A
                         GROUP OF ONE OR MORE SPECIFIED AMINO ACIDS AS DEFINED IN
                         THE SPECIFICATION"

(xi) SEQUENCE DESCRIPTION: SEQ ID NO:4:

Cys Xaa Xaa Xaa Xaa Leu Tyr Val Xaa Phe Xaa Xaa Xaa Gly Trp Xaa
1               5                   10                  15

Xaa Trp Xaa Xaa Ala Pro Xaa Gly Xaa Xaa Ala Xaa Tyr Cys Xaa Gly
            20                  25                  30

Xaa Cys Xaa Xaa Pro Xaa Xaa Xaa Xaa Xaa Xaa Xaa Asn His Ala
        35                  40                  45

Xaa Xaa Xaa Xaa Leu Xaa Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Leu Xaa Xaa
65                  70                  75                  80

Xaa Xaa Xaa Xaa Xaa Val Xaa Leu Xaa Xaa Xaa Xaa Xaa Met Xaa Val
                85                  90                  95

Xaa Xaa Cys Gly Cys Xaa
            100

(2) INFORMATION FOR SEQ ID NO:5:

(i) SEQUENCE CHARACTERISTICS:
          (A) LENGTH: 139 amino acids
          (B) TYPE: amino acid
          (C) STRANDEDNESS: single
          (D) TOPOLOGY: linear (ii) MOLECULE TYPE: protein (ix) FEATURE:
          (A) NAME/KEY: Protein
          (B) LOCATION: 1..139
          (D) OTHER INFORMATION: /note= "HOP-1 (MATURE FORM)"

(xi) SEQUENCE DESCRIPTION: SEQ ID NO:5:

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

(2) INFORMATION FOR SEQ ID NO:6:

(i) SEQUENCE CHARACTERISTICS:

(A) LENGTH: 139 amino acids
         (B) TYPE: amino acid
         (C) STRANDEDNESS: single
         (D) TOPOLOGY: linear (ii) MOLECULE TYPE: protein (ix) FEATURE:
         (A) NAME/KEY: Protein
         (B) LOCATION: 1..139
         (D) OTHER INFORMATION: /note= "MOP-1 (MATURE FORM)"

(xi) SEQUENCE DESCRIPTION: SEQ ID NO:6:

```
Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

(2) INFORMATION FOR SEQ ID NO:7:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (ix) FEATURE:
         (A) NAME/KEY: Protein
         (B) LOCATION: 1..139
         (D) OTHER INFORMATION: /note= "HOP-2 (MATURE FORM)"

(xi) SEQUENCE DESCRIPTION: SEQ ID NO:7:

```
Ala Val Arg Pro Leu Arg Arg Arg Gln Pro Lys Lys Ser Asn Glu Leu
1               5                   10                  15

Pro Gln Ala Asn Arg Leu Pro Gly Ile Phe Asp Asp Val His Gly Ser
            20                  25                  30

His Gly Arg Gln Val Cys Arg Arg His Glu Leu Tyr Val Ser Phe Gln
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ser Phe Pro Leu Asp Ser Cys Met Asn
65                  70                  75                  80

Ala Thr Asn His Ala Ile Leu Gln Ser Leu Val His Leu Met Lys Pro
                85                  90                  95

Asn Ala Val Pro Lys Ala Cys Cys Ala Pro Thr Lys Leu Ser Ala Thr
            100                 105                 110
```

```
Ser Val Leu Tyr Tyr Asp Ser Ser Asn Asn Val Ile Leu Arg Lys His
        115                 120                 125

Arg Asn Met Val Val Lys Ala Cys Gly Cys His
        130                 135

(2) INFORMATION FOR SEQ ID NO:8:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..139
        (D) OTHER INFORMATION: /note= "MOP-2 (MATURE FORM)"

(xi) SEQUENCE DESCRIPTION: SEQ ID NO:8:

Ala Ala Arg Pro Leu Lys Arg Arg Gln Pro Lys Lys Thr Asn Glu Leu
1               5                   10                  15

Pro His Pro Asn Lys Leu Pro Gly Ile Phe Asp Asp Gly His Gly Ser
            20                  25                  30

Arg Gly Arg Glu Val Cys Arg Arg His Glu Leu Tyr Val Ser Phe Arg
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ala Phe Pro Leu Asp Ser Cys Met Asn
65                  70                  75                  80

Ala Thr Asn His Ala Ile Leu Gln Ser Leu Val His Leu Met Lys Pro
            85                  90                  95

Asp Val Val Pro Lys Ala Cys Cys Ala Pro Thr Lys Leu Ser Ala Thr
                100                 105                 110

Ser Val Leu Tyr Tyr Asp Ser Ser Asn Asn Val Ile Leu Arg Lys His
        115                 120                 125

Arg Asn Met Val Val Lys Ala Cys Gly Cys His
        130                 135

(2) INFORMATION FOR SEQ ID NO:9:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..101
        (D) OTHER INFORMATION: /note= "CBMP-2A(FX)"

(xi) SEQUENCE DESCRIPTION: SEQ ID NO:9:

Cys Lys Arg His Pro Leu Tyr Val Asp Phe Ser Asp Val Gly Trp Asn
1               5                   10                  15

Asp Trp Ile Val Ala Pro Pro Gly Tyr His Ala Phe Tyr Cys His Gly
            20                  25                  30

Glu Cys Pro Phe Pro Leu Ala Asp His Leu Asn Ser Thr Asn His Ala
        35                  40                  45
```

```
Ile Val Gln Thr Leu Val Asn Ser Val Asn Ser Lys Ile Pro Lys Ala
        50                  55                  60

Cys Cys Val Pro Thr Glu Leu Ser Ala Ile Ser Met Leu Tyr Leu Asp
 65                  70                  75                  80

Glu Asn Glu Lys Val Val Leu Lys Asn Tyr Gln Asp Met Val Val Glu
                    85                  90                  95

Gly Cys Gly Cys Arg
            100
```

(2) INFORMATION FOR SEQ ID NO:10:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..101
        (D) OTHER INFORMATION: /note= "CBMP-2B(FX)"

(xi) SEQUENCE DESCRIPTION: SEQ ID NO:10:

```
Cys Arg

```
                50                  55                  60
Ala Cys Cys Val Pro Thr Gln Leu Asp Ser Val Ala Met Leu Tyr Leu
65                  70                  75                  80

Asn Asp Gln Ser Thr Val Val Leu Lys Asn Tyr Gln Glu Met Thr Val
                85                  90                  95

Val Gly Cys Gly Cys Arg
            100
```

(2) INFORMATION FOR SEQ ID NO:12:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /note= "VGL(FX)"

(xi) SEQUENCE DESCRIPTION: SEQ ID NO:12:

```
Cys Lys Lys Arg His Leu Tyr Val Glu Phe Lys Asp Val Gly Trp Gln
1               5                   10                  15

Asn Trp Val Ile Ala Pro Gln Gly Tyr Met Ala Asn Tyr Cys Tyr Gly
                20                  25                  30

Glu Cys Pro Tyr Pro Leu Thr Glu Ile Leu Asn Gly Ser Asn His Ala
            35                  40                  45

Ile Leu Gln Thr Leu Val His Ser Ile Glu Pro Glu Asp Ile Pro Leu
50                  55                  60

Pro Cys Cys Val Pro Thr Lys Met Ser Pro Ile Ser Met Leu Phe Tyr
65                  70                  75                  80

Asp Asn Asn Asp Asn Val Val Leu Arg His Tyr Glu Asn Met Ala Val
                85                  90                  95

Asp Glu Cys Gly Cys Arg
            100
```

(2) INFORMATION FOR SEQ ID NO:13:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /note= "VGR-1(FX)"

(xi) SEQUENCE DESCRIPTION: SEQ ID NO:13:

```
Cys Lys Lys His Glu Leu Tyr Val Ser Phe Gln Asp Val Gly Trp Gln
1               5                   10                  15

Asp Trp Ile Ile Ala Pro Lys Gly Tyr Ala Ala Asn Tyr Cys Asp Gly
                20                  25                  30

Glu Cys Ser Phe Pro Leu Asn Ala His Met Asn Ala Thr Asn His Ala
            35                  40                  45

Ile Val Gln Thr Leu Val His Val Met Asn Pro Glu Tyr Val Pro Lys
50                  55                  60
```

-continued

```
Pro Cys Cys Ala Pro Thr Lys Val Asn Ala Ile Ser Val Leu Tyr Phe
65                  70                  75                  80

Asp Asp Asn Ser Asn Val Ile Leu Lys Lys Tyr Arg Asn Met Val Val
                85                  90                  95

Arg Ala Cys Gly Cys His
            100
```

(2) INFORMATION FOR SEQ ID NO:14:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..106
        (D) OTHER INFORMATION: /note= "GDF-1 (FX)"

(xi) SEQUENCE DESCRIPTION: SEQ ID NO:14:

```
Cys Arg Ala Arg Arg Leu Tyr Val Ser Phe Arg Glu Val Gly Trp His
1               5                   10                  15

Arg Trp Val Ile Ala Pro Arg Gly Phe Leu Ala Asn Tyr Cys Gln Gly
                20                  25                  30

Gln Cys Ala Leu Pro Val Ala Leu Ser Gly Ser Gly Gly Pro Pro Ala
            35                  40                  45

Leu Asn His Ala Val Leu Arg Ala Leu Met His Ala Ala Ala Pro Gly
        50                  55                  60

Ala Ala Asp Leu Pro Cys Cys Val Pro Ala Arg Leu Ser Pro Ile Ser
65                  70                  75                  80

Val Leu Phe Phe Asp Asn Ser Asp Asn Val Val Leu Arg Gln Tyr Glu
                85                  90                  95

Asp Met Val Val Asp Glu Cys Gly Cys Arg
                100                 105
```

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Cys Xaa Xaa Xaa Xaa
1               5
```

(2) INFORMATION FOR SEQ ID NO:16:

(i) SEQUENCE CHARACTERISTICS:
        (A) LENGTH: 1822 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 49..1341

(D) OTHER INFORMATION: /product= "HOP-1"

(xi) SEQUENCE DESCRIPTION: SEQ ID NO:16:

| | | | | | | | | | | | | | | | | |
|---|---|---|---|---|---|---|---|---|---|---|---|---|---|---|---|---|
| GGTGCGGGCC | CGGAGCCCGG | AGCCCGGGTA | GCGCGTAGAG | CCGGCGCG | ATG | CAC | GTG | | | | | | | | | 57 |
| | | | | | Met | His | Val | | | | | | | | | |
| | | | | | 1 | | | | | | | | | | | |

```
CGC TCA CTG CGA GCT GCG GCG CCG CAC AGC TTC GTG GCG CTC TGG GCA        105
Arg Ser Leu Arg Ala Ala Ala Pro His Ser Phe Val Ala Leu Trp Ala
    5                  10                  15

CCC CTG TTC CTG CTG CGC TCC GCC CTG GCC GAC TTC AGC CTG GAC AAC        153
Pro Leu Phe Leu Leu Arg Ser Ala Leu Ala Asp Phe Ser Leu Asp Asn
 20                  25                  30                  35

GAG GTG CAC TCG AGC TTC ATC CAC CGG CGC CTC CGC AGC CAG GAG CGG        201
Glu Val His Ser Ser Phe Ile His Arg Arg Leu Arg Ser Gln Glu Arg
                 40                  45                  50

CGG GAG ATG CAG CGC GAG ATC CTC TCC ATT TTG GGC TTG CCC CAC CGC        249
Arg Glu Met Gln Arg Glu Ile Leu Ser Ile Leu Gly Leu Pro His Arg
             55                  60                  65

CCG CGC CCG CAC CTC CAG GGC AAG CAC AAC TCG GCA CCC ATG TTC ATG        297
Pro Arg Pro His Leu Gln Gly Lys His Asn Ser Ala Pro Met Phe Met
         70                  75                  80

CTG GAC CTG TAC AAC GCC ATG GCG GTG GAG GAG GGC GGC GGG CCC GGC        345
Leu Asp Leu Tyr Asn Ala Met Ala Val Glu Glu Gly Gly Gly Pro Gly
     85                  90                  95

GGC CAG GGC TTC TCC TAC CCC TAC AAG GCC GTC TTC AGT ACC CAG GGC        393
Gly Gln Gly Phe Ser Tyr Pro Tyr Lys Ala Val Phe Ser Thr Gln Gly
100                 105                 110                 115

CCC CCT CTG GCC AGC CTG CAA GAT AGC CAT TTC CTC ACC GAC GCC GAC        441
Pro Pro Leu Ala Ser Leu Gln Asp Ser His Phe Leu Thr Asp Ala Asp
                120                 125                 130

ATG GTC ATG AGC TTC GTC AAC CTC GTG GAA CAT GAC AAG GAA TTC TTC        489
Met Val Met Ser Phe Val Asn Leu Val Glu His Asp Lys Glu Phe Phe
            135                 140                 145

CAC CCA CGC TAC CAC CAT CGA GAG TTC CGG TTT GAT CTT TCC AAG ATC        537
His Pro Arg Tyr His His Arg Glu Phe Arg Phe Asp Leu Ser Lys Ile
        150                 155                 160

CCA GAA GGG GAA GCT GTC ACG GCA GCC GAA TTC CGG ATC TAC AAG GAC        585
Pro Glu Gly Glu Ala Val Thr Ala Ala Glu Phe Arg Ile Tyr Lys Asp
    165                 170                 175

TAC ATC CGG GAA CGC TTC GAC AAT GAG ACG TTC CGG ATC AGC GTT TAT        633
Tyr Ile Arg Glu Arg Phe Asp Asn Glu Thr Phe Arg Ile Ser Val Tyr
180                 185                 190                 195

CAG GTG CTC CAG GAG CAC TTG GGC AGG GAA TCG GAT CTC TTC CTG CTC        681
Gln Val Leu Gln Glu His Leu Gly Arg Glu Ser Asp Leu Phe Leu Leu
                200                 205                 210

GAC AGC CGT ACC CTC TGG GCC TCG GAG GAG GGC TGG CTG GTG TTT GAC        729
Asp Ser Arg Thr Leu Trp Ala Ser Glu Glu Gly Trp Leu Val Phe Asp
            215                 220                 225

ATC ACA GCC ACC AGC AAC CAC TGG GTG GTC AAT CCG CGG CAC AAC CTG        777
Ile Thr Ala Thr Ser Asn His Trp Val Val Asn Pro Arg His Asn Leu
        230                 235                 240

GGC CTG CAG CTC TCG GTG GAG ACG CTG GAT GGG CAG AGC ATC AAC CCC        825
Gly Leu Gln Leu Ser Val Glu Thr Leu Asp Gly Gln Ser Ile Asn Pro
    245                 250                 255

AAG TTG GCG GGC CTG ATT GGG CGG CAC GGG CCC CAG AAC AAG CAG CCC        873
Lys Leu Ala Gly Leu Ile Gly Arg His Gly Pro Gln Asn Lys Gln Pro
260                 265                 270                 275

TTC ATG GTG GCT TTC TTC AAG GCC ACG GAG GTC CAC TTC CGC AGC ATC        921
Phe Met Val Ala Phe Phe Lys Ala Thr Glu Val His Phe Arg Ser Ile
                280                 285                 290
```

```
CGG TCC ACG GGG AGC AAA CAG CGC AGC CAG AAC CGC TCC AAG ACG CCC       969
Arg Ser Thr Gly Ser Lys Gln Arg Ser Gln Asn Arg Ser Lys Thr Pro
            295                 300                 305

AAG AAC CAG GAA GCC CTG CGG ATG GCC AAC GTG GCA GAG AAC AGC AGC      1017
Lys Asn Gln Glu Ala Leu Arg Met Ala Asn Val Ala Glu Asn Ser Ser
            310                 315                 320

AGC GAC CAG AGG CAG GCC TGT AAG AAG CAC GAG CTG TAT GTC AGC TTC      1065
Ser Asp Gln Arg Gln Ala Cys Lys Lys His Glu Leu Tyr Val Ser Phe
325                 330                 335

CGA GAC CTG GGC TGG CAG GAC TGG ATC ATC GCG CCT GAA GGC TAC GCC      1113
Arg Asp Leu Gly Trp Gln Asp Trp Ile Ile Ala Pro Glu Gly Tyr Ala
340                 345                 350                 355

GCC TAC TAC TGT GAG GGG GAG TGT GCC TTC CCT CTG AAC TCC TAC ATG      1161
Ala Tyr Tyr Cys Glu Gly Glu Cys Ala Phe Pro Leu Asn Ser Tyr Met
                360                 365                 370

AAC GCC ACC AAC CAC GCC ATC GTG CAG ACG CTG GTC CAC TTC ATC AAC      1209
Asn Ala Thr Asn His Ala Ile Val Gln Thr Leu Val His Phe Ile Asn
            375                 380                 385

CCG GAA ACG GTG CCC AAG CCC TGC TGT GCG CCC ACG CAG CTC AAT GCC      1257
Pro Glu Thr Val Pro Lys Pro Cys Cys Ala Pro Thr Gln Leu Asn Ala
            390                 395                 400

ATC TCC GTC CTC TAC TTC GAT GAC AGC TCC AAC GTC ATC CTG AAG AAA      1305
Ile Ser Val Leu Tyr Phe Asp Asp Ser Ser Asn Val Ile Leu Lys Lys
405                 410                 415

TAC AGA AAC ATG GTG GTC CGG GCC TGT GGC TGC CAC TAGCTCCTCC           1351
Tyr Arg Asn Met Val Val Arg Ala Cys Gly Cys His
420                 425                 430

GAGAATTCAG ACCCTTTGGG GCCAAGTTTT TCTGGATCCT CCATTGCTCG CCTTGGCCAG    1411

GAACCAGCAG ACCAACTGCC TTTTGTGAGA CCTTCCCCTC CCTATCCCCA ACTTTAAAGG    1471

TGTGAGAGTA TTAGGAAACA TGAGCAGCAT ATGGCTTTTG ATCAGTTTTT CAGTGGCAGC    1531

ATCCAATGAA CAAGATCCTA CAAGCTGTGC AGGCAAAACC TAGCAGGAAA AAAAAACAAC    1591

GCATAAAGAA AAATGGCCGG GCCAGGTCAT TGGCTGGGAA GTCTCAGCCA TGCACGGACT    1651

CGTTTCCAGA GGTAATTATG AGCGCCTACC AGCCAGGCCA CCCAGCCGTG GGAGGAAGGG    1711

GGCGTGGCAA GGGGTGGGCA CATTGGTGTC TGTGCGAAAG GAAATTGAC CCGGAAGTTC     1771

CTGTAATAAA TGTCACAATA AAACGAATGA ATGAAAAAAA AAAAAAAAA A              1822

(2) INFORMATION FOR SEQ ID NO:17:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:17:

Met His Val Arg Ser Leu Arg Ala Ala Pro His Ser Phe Val Ala
 1               5                  10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80
```

```
Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

(2) INFORMATION FOR SEQ ID NO:18:

(i) SEQUENCE CHARACTERISTICS:
        (A) LENGTH: 1873 base pairs
        (B) TYPE: nucleic acid
        (C) STRANDEDNESS: single
        (D) TOPOLOGY: linear (ii) MOLECULE TYPE: cDNA (ix) FEATURE:
```

(A) NAME/KEY: CDS
(B) LOCATION: 104..1393
(D) OTHER INFORMATION: /product= "MOP1 (CDNA)"

(xi) SEQUENCE DESCRIPTION: SEQ ID NO:18:

```
CTGCAGCAAG TGACCTCGGG TCGTGGACCG CTGCCCTGCC CCCTCCGCTG CCACCTGGGG        60

CGGCGCGGGC CCGGTGCCCC GGATCGCGCG TAGAGCCGGC GCG ATG CAC GTG CGC       115
                                              Met His Val Arg
                                                1

TCG CTG CGC GCT GCG GCG CCA CAC AGC TTC GTG GCG CTC TGG GCG CCT       163
Ser Leu Arg Ala Ala Ala Pro His Ser Phe Val Ala Leu Trp Ala Pro
  5              10                  15                  20

CTG TTC TTG CTG CGC TCC GCC CTG GCC GAT TTC AGC CTG GAC AAC GAG       211
Leu Phe Leu Leu Arg Ser Ala Leu Ala Asp Phe Ser Leu Asp Asn Glu
             25                  30                  35

GTG CAC TCC AGC TTC ATC CAC CGG CGC CTC CGC AGC CAG GAG CGG CGG       259
Val His Ser Ser Phe Ile His Arg Arg Leu Arg Ser Gln Glu Arg Arg
                 40                  45                  50

GAG ATG CAG CGG GAG ATC CTG TCC ATC TTA GGG TTG CCC CAT CGC CCG       307
Glu Met Gln Arg Glu Ile Leu Ser Ile Leu Gly Leu Pro His Arg Pro
             55                  60                  65

CGC CCG CAC CTC CAG GGA AAG CAT AAT TCG GCG CCC ATG TTC ATG TTG       355
Arg Pro His Leu Gln Gly Lys His Asn Ser Ala Pro Met Phe Met Leu
 70                  75                  80

GAC CTG TAC AAC GCC ATG GCG GTG GAG GAG AGC GGG CCG GAC GGA CAG       403
Asp Leu Tyr Asn Ala Met Ala Val Glu Glu Ser Gly Pro Asp Gly Gln
 85                  90                  95                 100

GGC TTC TCC TAC CCC TAC AAG GCC GTC TTC AGT ACC CAG GGC CCC CCT       451
Gly Phe Ser Tyr Pro Tyr Lys Ala Val Phe Ser Thr Gln Gly Pro Pro
                105                 110                 115

TTA GCC AGC CTG CAG GAC AGC CAT TTC CTC ACT GAC GCC GAC ATG GTC       499
Leu Ala Ser Leu Gln Asp Ser His Phe Leu Thr Asp Ala Asp Met Val
            120                 125                 130

ATG AGC TTC GTC AAC CTA GTG GAA CAT GAC AAA GAA TTC TTC CAC CCT       547
Met Ser Phe Val Asn Leu Val Glu His Asp Lys Glu Phe Phe His Pro
Ser Phe Val Asn Leu Val Glu His Asp Lys Glu Phe Phe His Pro
            135                 140                 145

CGA TAC CAC CAT CGG GAG TTC CGG TTT GAT CTT TCC AAG ATC CCC GAG       595
Arg Tyr His His Arg Glu Phe Arg Phe Asp Leu Ser Lys Ile Pro Glu
150                 155                 160

GGC GAA CGG GTG ACC GCA GCC GAA TTC AGG ATC TAT AAG GAC TAC ATC       643
Gly Glu Arg Val Thr Ala Ala Glu Phe Arg Ile Tyr Lys Asp Tyr Ile
165                 170                 175                 180

CGG GAG CGA TTT GAC AAC GAG ACC TTC CAG ATC ACA GTC TAT CAG GTG       691
Arg Glu Arg Phe Asp Asn Glu Thr Phe Gln Ile Thr Val Tyr Gln Val
                185                 190                 195

CTC CAG GAG CAC TCA GGC AGG GAG TCG GAC CTC TTC TTG CTG GAC AGC       739
Leu Gln Glu His Ser Gly Arg Glu Ser Asp Leu Phe Leu Leu Asp Ser
            200                 205                 210

CGC ACC ATC TGG GCT TCT GAG GAG GGC TGG TTG GTG TTT GAT ATC ACA       787
Arg Thr Ile Trp Ala Ser Glu Glu Gly Trp Leu Val Phe Asp Ile Thr
            215                 220                 225

GCC ACC AGC AAC CAC TGG GTG GTC AAC CCT CGG CAC AAC CTG GGC TTA       835
Ala Thr Ser Asn His Trp Val Val Asn Pro Arg His Asn Leu Gly Leu
230                 235                 240

CAG CTC TCT GTG GAG ACC CTG GAT GGG CAG AGC ATC AAC CCC AAG TTG       883
Gln Leu Ser Val Glu Thr Leu Asp Gly Gln Ser Ile Asn Pro Lys Leu
245                 250                 255                 260

GCA GGC CTG ATT GGA CGG CAT GGA CCC CAG AAC AAG CAA CCC TTC ATG       931
Ala Gly Leu Ile Gly Arg His Gly Pro Gln Asn Lys Gln Pro Phe Met
                265                 270                 275
```

```
GTG GCC TTC TTC AAG GCC ACG GAA GTC CAT CTC CGT AGT ATC CGG TCC      979
Val Ala Phe Phe Lys Ala Thr Glu Val His Leu Arg Ser Ile Arg Ser
            280                 285                 290

ACG GGG GGC AAG CAG CGC AGC CAG AAT CGC TCC AAG ACG CCA AAG AAC     1027
Thr Gly Gly Lys Gln Arg Ser Gln Asn Arg Ser Lys Thr Pro Lys Asn
            295                 300                 305

CAA GAG GCC CTG AGG ATG GCC AGT GTG GCA GAA AAC AGC AGC AGT GAC     1075
Gln Glu Ala Leu Arg Met Ala Ser Val Ala Glu Asn Ser Ser Ser Asp
            310                 315                 320

CAG AGG CAG GCC TGC AAG AAA CAT GAG CTG TAC GTC AGC TTC CGA GAC     1123
Gln Arg Gln Ala Cys Lys Lys His Glu Leu Tyr Val Ser Phe Arg Asp
325                 330                 335                 340

CTT GGC TGG CAG GAC TGG ATC ATT GCA CCT GAA GGC TAT GCT GCC TAC     1171
Leu Gly Trp Gln Asp Trp Ile Ile Ala Pro Glu Gly Tyr Ala Ala Tyr
                345                 350                 355

TAC TGT GAG GGA GAG TGC GCC TTC CCT CTG AAC TCC TAC ATG AAC GCC     1219
Tyr Cys Glu Gly Glu Cys Ala Phe Pro Leu Asn Ser Tyr Met Asn Ala
                360                 365                 370

ACC AAC CAC GCC ATC GTC CAG ACA CTG GTT CAC TTC ATC AAC CCA GAC     1267
Thr Asn His Ala Ile Val Gln Thr Leu Val His Phe Ile Asn Pro Asp
            375                 380                 385

ACA GTA CCC AAG CCC TGC TGT GCG CCC ACC CAG CTC AAC GCC ATC TCT     1315
Thr Val Pro Lys Pro Cys Cys Ala Pro Thr Gln Leu Asn Ala Ile Ser
            390                 395                 400

GTC CTC TAC TTC GAC GAC AGC TCT AAT GTC ATC CTG AAG AAG TAC AGA     1363
Val Leu Tyr Phe Asp Asp Ser Ser Asn Val Ile Leu Lys Lys Tyr Arg
405                 410                 415                 420

AAC ATG GTG GTC CGG GCC TGT GGC TGC CAC TAGCTCTTCC TGAGACCCTG       1413
Asn Met Val Val Arg Ala Cys Gly Cys His
                425                 430

ACCTTTGCGG GGCCACACCT TTCCAAATCT TCGATGTCTC ACCATCTAAG TCTCTCACTG   1473

CCCACCTTGG CGAGGAGAAC AGACCAACCT CTCCTGAGCC TTCCCTCACC TCCCAACCGG   1533

AAGCATGTAA GGGTTCCAGA AACCTGAGCG TGCAGCAGCT GATGAGCGCC CTTTCCTTCT   1593

GGCACGTGAC GGACAAGATC CTACCAGCTA CCACAGCAAA CGCCTAAGAG CAGGAAAAAT   1653

GTCTGCCAGG AAAGTGTCCA GTGTCCACAT GGCCCCTGGC GCTCTGAGTC TTTGAGGAGT   1713

AATCGCAAGC CTCGTTCAGC TGCAGCAGAA GGAAGGGCTT AGCCAGGGTG GGCGCTGGCG   1773

TCTGTGTTGA AGGGAAACCA AGCAGAAGCC ACTGTAATGA TATGTCACAA TAAAACCCAT   1833

GAATGAAAAA AAAAAAAAAA AAAAAAAAAA AAAAGAATTC                        1873

(2) INFORMATION FOR SEQ ID NO:19:

(i) SEQUENCE CHARACTERISTICS:
        (A) LENGTH: 430 amino acids
        (B) TYPE: amino acid
        (D) TOPOLOGY: linear (ii) MOLECULE TYPE: protein (xi) SEQUENCE DESCRIPTION: SEQ ID NO:19:

Met His Val Arg Ser Leu Arg Ala Ala Pro His Ser Phe Val Ala
 1               5                  10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
```

```
             50                  55                  60
Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Ser Gly
                 85                  90                  95

Pro Asp Gly Gln Gly Phe Ser Tyr Pro Tyr Lys Ala Val Phe Ser Thr
            100                 105                 110

Gln Gly Pro Pro Leu Ala Ser Leu Gln Asp Ser His Phe Leu Thr Asp
            115                 120                 125

Ala Asp Met Val Met Ser Phe Val Asn Leu Val Glu His Asp Lys Glu
130                 135                 140

Phe Phe His Pro Arg Tyr His Arg Glu Phe Arg Phe Asp Leu Ser
145                 150                 155                 160

Lys Ile Pro Glu Gly Glu Arg Val Thr Ala Ala Glu Phe Arg Ile Tyr
                165                 170                 175

Lys Asp Tyr Ile Arg Glu Arg Phe Asp Asn Glu Thr Phe Gln Ile Thr
            180                 185                 190

Val Tyr Gln Val Leu Gln Glu His Ser Gly Arg Glu Ser Asp Leu Phe
            195                 200                 205

Leu Leu Asp Ser Arg Thr Ile Trp Ala Ser Glu Glu Gly Trp Leu Val
210                 215                 220

Phe Asp Ile Thr Ala Thr Ser Asn His Trp Val Val Asn Pro Arg His
225                 230                 235                 240

Asn Leu Gly Leu Gln Leu Ser Val Glu Thr Leu Asp Gly Gln Ser Ile
                245                 250                 255

Asn Pro Lys Leu Ala Gly Leu Ile Gly Arg His Gly Pro Gln Asn Lys
            260                 265                 270

Gln Pro Phe Met Val Ala Phe Phe Lys Ala Thr Glu Val His Leu Arg
            275                 280                 285

Ser Ile Arg Ser Thr Gly Gly Lys Gln Arg Ser Gln Asn Arg Ser Lys
290                 295                 300

Thr Pro Lys Asn Gln Glu Ala Leu Arg Met Ala Ser Val Ala Glu Asn
305                 310                 315                 320

Ser Ser Ser Asp Gln Arg Gln Ala Cys Lys Lys His Glu Leu Tyr Val
                325                 330                 335

Ser Phe Arg Asp Leu Gly Trp Gln Asp Trp Ile Ile Ala Pro Glu Gly
            340                 345                 350

Tyr Ala Ala Tyr Tyr Cys Glu Gly Glu Cys Ala Phe Pro Leu Asn Ser
            355                 360                 365

Tyr Met Asn Ala Thr Asn His Ala Ile Val Gln Thr Leu Val His Phe
            370                 375                 380

Ile Asn Pro Asp Thr Val Pro Lys Pro Cys Cys Ala Pro Thr Gln Leu
385                 390                 395                 400

Asn Ala Ile Ser Val Leu Tyr Phe Asp Asp Ser Ser Asn Val Ile Leu
                405                 410                 415

Lys Lys Tyr Arg Asn Met Val Val Arg Ala Cys Gly Cys His
            420                 425                 430

(2) INFORMATION FOR SEQ ID NO:20:

(i) SEQUENCE CHARACTERISTICS:
        (A) LENGTH: 1723 base pairs
        (B) TYPE: nucleic acid
        (C) STRANDEDNESS: single
        (D) TOPOLOGY: linear
```

(ii) MOLECULE TYPE: cDNA (ix) FEATURE:
    (A) NAME/KEY: CDS
    (B) LOCATION: 490..1695

(xi) SEQUENCE DESCRIPTION: SEQ ID NO:20:

```
GGCGCCGGCA GAGCAGGAGT GGCTGGAGGA GCTGTGGTTG GAGCAGGAGG TGGCACGGCA        60

GGGCTGGAGG GCTCCCTATG AGTGGCGGAG ACGGCCCAGG AGGCGCTGGA GCAACAGCTC       120

CCACACCGCA CCAAGCGGTG GCTGCAGGAG CTCGCCCATC GCCCCTGCGC TGCTCGGACC       180

GCGGCCACAG CCGGACTGGC GGGTACGGCG GCGACAGAGG CATTGGCCGA GAGTCCCAGT       240

CCGCAGAGTA GCCCCGGCCT CGAGGCGGTG GCGTCCCGGT CCTCTCCGTC CAGGAGCCAG       300

GACAGGTGTC GCGCGGCGGG GCTCCAGGGA CCGCGCCTGA GGCCGGCTGC CCGCCCGTCC       360

CGCCCCGCCC CGCCGCCCGC CGCCCGCCGA GCCCAGCCTC CTTGCCGTCG GGGCGTCCCC       420

AGGCCCTGGG TCGGCCGCGG AGCCGATGCG CGCCCGCTGA GCGCCCCAGC TGAGCGCCCC       480

CGGCCTGCC ATG ACC GCG CTC CCC GGC CCG CTC TGG CTC CTG GGC CTG          528
           Met Thr Ala Leu Pro Gly Pro Leu Trp Leu Leu Gly Leu
             1               5                  10

GCG CTA TGC GCG CTG GGC GGG GGC GGC CCC GGC CTG CGA CCC CCG CCC        576
Ala Leu Cys Ala Leu Gly Gly Gly Gly Pro Gly Leu Arg Pro Pro Pro
         15                  20                  25

GGC TGT CCC CAG CGA CGT CTG GGC GCG CGC GAG CGC CGG GAC GTG CAG        624
Gly Cys Pro Gln Arg Arg Leu Gly Ala Arg Glu Arg Arg Asp Val Gln
 30                  35                  40                  45

CGC GAG ATC CTG GCG GTG CTC GGG CTG CCT GGG CGG CCC CGG CCC CGC        672
Arg Glu Ile Leu Ala Val Leu Gly Leu Pro Gly Arg Pro Arg Pro Arg
                 50                  55                  60

GCG CCA CCC GCC GCC TCC CGG CTG CCC GCG TCC GCG CCG CTC TTC ATG        720
Ala Pro Pro Ala Ala Ser Arg Leu Pro Ala Ser Ala Pro Leu Phe Met
             65                  70                  75

CTG GAC CTG TAC CAC GCC ATG GCC GGC GAC GAC GAC GAG GAC GGC GCG        768
Leu Asp Leu Tyr His Ala Met Ala Gly Asp Asp Asp Glu Asp Gly Ala
             80                  85                  90

CCC GCG GAG CGG CGC CTG GGC CGC GCC GAC CTG GTC ATG AGC TTC GTT        816
Pro Ala Glu Arg Arg Leu Gly Arg Ala Asp Leu Val Met Ser Phe Val
         95                 100                 105

AAC ATG GTG GAG CGA GAC CGT GCC CTG GGC CAC CAG GAG CCC CAT TGG        864
Asn Met Val Glu Arg Asp Arg Ala Leu Gly His Gln Glu Pro His Trp
110                 115                 120                 125

AAG GAG TTC CGC TTT GAC CTG ACC CAG ATC CCG GCT GGG GAG GCG GTC        912
Lys Glu Phe Arg Phe Asp Leu Thr Gln Ile Pro Ala Gly Glu Ala Val
                130                 135                 140

ACA GCT GCG GAG TTC CGG ATT TAC AAG GTG CCC AGC ATC CAC CTG CTC        960
Thr Ala Ala Glu Phe Arg Ile Tyr Lys Val Pro Ser Ile His Leu Leu
            145                 150                 155

AAC AGG ACC CTC CAC GTC AGC ATG TTC CAG GTG GTC CAG GAG CAG TCC       1008
Asn Arg Thr Leu His Val Ser Met Phe Gln Val Val Gln Glu Gln Ser
        160                 165                 170

AAC AGG GAG TCT GAC TTG TTC TTT TTG GAT CTT CAG ACG CTC CGA GCT       1056
Asn Arg Glu Ser Asp Leu Phe Phe Leu Asp Leu Gln Thr Leu Arg Ala
    175                 180                 185

GGA GAC GAG GGC TGG CTG GTG CTG GAT GTC ACA GCA GCC AGT GAC TGC       1104
Gly Asp Glu Gly Trp Leu Val Leu Asp Val Thr Ala Ala Ser Asp Cys
190                 195                 200                 205

TGG TTG CTG AAG CGT CAC AAG GAC CTG GGA CTC CGC CTC TAT GTG GAG       1152
Trp Leu Leu Lys Arg His Lys Asp Leu Gly Leu Arg Leu Tyr Val Glu
```

```
            210                 215                 220
ACT GAG GAC GGG CAC AGC GTG GAT CCT GGC CTG GCC GGC CTG CTG GGT      1200
Thr Glu Asp Gly His Ser Val Asp Pro Gly Leu Ala Gly Leu Leu Gly
            225                 230                 235

CAA CGG GCC CCA CGC TCC CAA CAG CCT TTC GTG GTC ACT TTC TTC AGG      1248
Gln Arg Ala Pro Arg Ser Gln Gln Pro Phe Val Val Thr Phe Phe Arg
            240                 245                 250

GCC AGT CCG AGT CCC ATC CGC ACC CCT CGG GCA GTG AGG CCA CTG AGG      1296
Ala Ser Pro Ser Pro Ile Arg Thr Pro Arg Ala Val Arg Pro Leu Arg
    255                 260                 265

AGG AGG CAG CCG AAG AAA AGC AAC GAG CTG CCG CAG GCC AAC CGA CTC      1344
Arg Arg Gln Pro Lys Lys Ser Asn Glu Leu Pro Gln Ala Asn Arg Leu
270                 275                 280                 285

CCA GGG ATC TTT GAT GAC GTC CAC GGC TCC CAC GGC CGG CAG GTC TGC      1392
Pro Gly Ile Phe Asp Asp Val His Gly Ser His Gly Arg Gln Val Cys
                290                 295                 300

CGT CGG CAC GAG CTC TAC GTC AGC TTC CAG GAC CTC GGC TGG CTG GAC      1440
Arg Arg His Glu Leu Tyr Val Ser Phe Gln Asp Leu Gly Trp Leu Asp
                305                 310                 315

TGG GTC ATC GCT CCC CAA GGC TAC TCG GCC TAT TAC TGT GAG GGG GAG      1488
Trp Val Ile Ala Pro Gln Gly Tyr Ser Ala Tyr Tyr Cys Glu Gly Glu
            320                 325                 330

TGC TCC TTC CCA CTG GAC TCC TGC ATG AAT GCC ACC AAC CAC GCC ATC      1536
Cys Ser Phe Pro Leu Asp Ser Cys Met Asn Ala Thr Asn His Ala Ile
            335                 340                 345

CTG CAG TCC CTG GTG CAC CTG ATG AAG CCA AAC GCA GTC CCC AAG GCG      1584
Leu Gln Ser Leu Val His Leu Met Lys Pro Asn Ala Val Pro Lys Ala
350                 355                 360                 365

TGC TGT GCA CCC ACC AAG CTG AGC GCC ACC TCT GTG CTC TAC TAT GAC      1632
Cys Cys Ala Pro Thr Lys Leu Ser Ala Thr Ser Val Leu Tyr Tyr Asp
                370                 375                 380

AGC AGC AAC AAC GTC ATC CTG CGC AAA CAC CGC AAC ATG GTG GTC AAG      1680
Ser Ser Asn Asn Val Ile Leu Arg Lys His Arg Asn Met Val Val Lys
                385                 390                 395

GCC TGC GGC TGC CAC TGAGTCAGCC CGCCCAGCCC TACTGCAG                   1723
Ala Cys Gly Cys His
            400

(2) INFORMATION FOR SEQ ID NO:21:

(i) SEQUENCE CHARACTERISTICS:
         (A) LENGTH: 402 amino acids
         (B) TYPE: amino acid
         (D) TOPOLOGY: linear (ii) MOLECULE TYPE: protein (xi) SEQUENCE DESCRIPTION: SEQ ID NO:21:

Met Thr Ala Leu Pro Gly Pro Leu Trp Leu Leu Gly Leu Ala Leu Cys
 1               5                  10                  15

Ala Leu Gly Gly Gly Gly Pro Gly Leu Arg Pro Pro Gly Cys Pro
            20                  25                  30

Gln Arg Arg Leu Gly Ala Arg Glu Arg Arg Asp Val Gln Arg Glu Ile
            35                  40                  45

Leu Ala Val Leu Gly Leu Pro Gly Arg Pro Arg Pro Arg Ala Pro Pro
        50                  55                  60

Ala Ala Ser Arg Leu Pro Ala Ser Ala Pro Leu Phe Met Leu Asp Leu
65                  70                  75                  80

Tyr His Ala Met Ala Gly Asp Asp Asp Glu Asp Gly Ala Pro Ala Glu
                85                  90                  95
```

```
Arg Arg Leu Gly Arg Ala Asp Leu Val Met Ser Phe Val Asn Met Val
            100                 105                 110

Glu Arg Asp Arg Ala Leu Gly His Gln Glu Pro His Trp Lys Glu Phe
        115                 120                 125

Arg Phe Asp Leu Thr Gln Ile Pro Ala Gly Glu Ala Val Thr Ala Ala
    130                 135                 140

Glu Phe Arg Ile Tyr Lys Val Pro Ser Ile His Leu Leu Asn Arg Thr
145                 150                 155                 160

Leu His Val Ser Met Phe Gln Val Val Gln Gln Ser Asn Arg Glu
                165                 170                 175

Ser Asp Leu Phe Phe Leu Asp Leu Gln Thr Leu Arg Ala Gly Asp Glu
            180                 185                 190

Gly Trp Leu Val Leu Asp Val Thr Ala Ala Ser Asp Cys Trp Leu Leu
        195                 200                 205

Lys Arg His Lys Asp Leu Gly Leu Arg Leu Tyr Val Glu Thr Glu Asp
    210                 215                 220

Gly His Ser Val Asp Pro Gly Leu Ala Gly Leu Leu Gly Gln Arg Ala
225                 230                 235                 240

Pro Arg Ser Gln Gln Pro Phe Val Val Thr Phe Phe Arg Ala Ser Pro
                245                 250                 255

Ser Pro Ile Arg Thr Pro Arg Ala Val Arg Pro Leu Arg Arg Arg Gln
            260                 265                 270

Pro Lys Lys Ser Asn Glu Leu Pro Gln Ala Asn Arg Leu Pro Gly Ile
        275                 280                 285

Phe Asp Asp Val His Gly Ser His Gly Arg Gln Val Cys Arg Arg His
    290                 295                 300

Glu Leu Tyr Val Ser Phe Gln Asp Leu Gly Trp Leu Asp Trp Val Ile
305                 310                 315                 320

Ala Pro Gln Gly Tyr Ser Ala Tyr Tyr Cys Glu Gly Glu Cys Ser Phe
                325                 330                 335

Pro Leu Asp Ser Cys Met Asn Ala Thr Asn His Ala Ile Leu Gln Ser
            340                 345                 350

Leu Val His Leu Met Lys Pro Asn Ala Val Pro Lys Ala Cys Cys Ala
        355                 360                 365

Pro Thr Lys Leu Ser Ala Thr Ser Val Leu Tyr Tyr Asp Ser Ser Asn
    370                 375                 380

Asn Val Ile Leu Arg Lys His Arg Asn Met Val Val Lys Ala Cys Gly
385                 390                 395                 400

Cys His (2) INFORMATION FOR SEQ ID NO:22:

(i) SEQUENCE CHARACTERISTICS:
        (A) LENGTH: 1926 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 93..1289
        (D) OTHER INFORMATION: /product= "MOP2 CDNA"

(xi) SEQUENCE DESCRIPTION: SEQ ID NO:22:

GCCAGGCACA GGTGCGCCGT CTGGTCCTCC CCGTCTGGCG TCAGCCGAGC CCGACCAGCT      60
```

-continued

```
ACCAGTGGAT GCGCGCCGGC TGAAAGTCCG AG ATG GCT ATG CGT CCC GGG CCA        113
                                   Met Ala Met Arg Pro Gly Pro
                                    1               5

CTC TGG CTA TTG GGC CTT GCT CTG TGC GCG CTG GGA GGC GGC CAC GGT        161
Leu Trp Leu Leu Gly Leu Ala Leu Cys Ala Leu Gly Gly Gly His Gly
             10                  15                  20

CCG CGT CCC CCG CAC ACC TGT CCC CAG CGT CGC CTG GGA GCG CGC GAG        209
Pro Arg Pro Pro His Thr Cys Pro Gln Arg Arg Leu Gly Ala Arg Glu
 25                  30                  35

CGC CGC GAC ATG CAG CGT GAA ATC CTG GCG GTG CTC GGG CTA CCG GGA        257
Arg Arg Asp Met Gln Arg Glu Ile Leu Ala Val Leu Gly Leu Pro Gly
 40                  45                  50                  55

CGG CCC CGA CCC CGT GCA CAA CCC GCC GCT GCC CGG CAG CCA GCG TCC        305
Arg Pro Arg Pro Arg Ala Gln Pro Ala Ala Ala Arg Gln Pro Ala Ser
                 60                  65                  70

GCG CCC CTC TTC ATG TTG GAC CTA TAC CAC GCC ATG ACC GAT GAC GAC        353
Ala Pro Leu Phe Met Leu Asp Leu Tyr His Ala Met Thr Asp Asp Asp
             75                  80                  85

GAC GGC GGG CCA CCA CAG GCT CAC TTA GGC CGT GCC GAC CTG GTC ATG        401
Asp Gly Gly Pro Pro Gln Ala His Leu Gly Arg Ala Asp Leu Val Met
         90                  95                 100

AGC TTC GTC AAC ATG GTG GAA CGC GAC CGT ACC CTG GGC TAC CAG GAG        449
Ser Phe Val Asn Met Val Glu Arg Asp Arg Thr Leu Gly Tyr Gln Glu
    105                 110                 115

CCA CAC TGG AAG GAA TTC CAC TTT GAC CTA ACC CAG ATC CCT GCT GGG        497
Pro His Trp Lys Glu Phe His Phe Asp Leu Thr Gln Ile Pro Ala Gly
120                 125                 130                 135

GAG GCT GTC ACA GCT GCT GAG TTC CGG ATC TAC AAA GAA CCC AGC ACC        545
Glu Ala Val Thr Ala Ala Glu Phe Arg Ile Tyr Lys Glu Pro Ser Thr
                140                 145                 150

CAC CCG CTC AAC ACA ACC CTC CAC ATC AGC ATG TTC GAA GTG GTC CAA        593
His Pro Leu Asn Thr Thr Leu His Ile Ser Met Phe Glu Val Val Gln
            155                 160                 165

GAG CAC TCC AAC AGG GAG TCT GAC TTG TTC TTT TTG GAT CTT CAG ACG        641
Glu His Ser Asn Arg Glu Ser Asp Leu Phe Phe Leu Asp Leu Gln Thr
        170                 175                 180

CTC CGA TCT GGG GAC GAG GGC TGG CTG GTG CTG GAC ATC ACA GCA GCC        689
Leu Arg Ser Gly Asp Glu Gly Trp Leu Val Leu Asp Ile Thr Ala Ala
    185                 190                 195

AGT GAC CGA TGG CTG CTG AAC CAT CAC AAG GAC CTG GGA CTC CGC CTC        737
Ser Asp Arg Trp Leu Leu Asn His His Lys Asp Leu Gly Leu Arg Leu
200                 205                 210                 215

TAT GTG GAA ACC GCG GAT GGG CAC AGC ATG GAT CCT GGC CTG GCT GGT        785
Tyr Val Glu Thr Ala Asp Gly His Ser Met Asp Pro Gly Leu Ala Gly
                220                 225                 230

CTG CTT GGA CGA CAA GCA CCA CGC TCC AGA CAG CCT TTC ATG GTA ACC        833
Leu Leu Gly Arg Gln Ala Pro Arg Ser Arg Gln Pro Phe Met Val Thr
            235                 240                 245

TTC TTC AGG GCC AGC CAG AGT CCT GTG CGG GCC CCT CGG GCA GCG AGA        881
Phe Phe Arg Ala Ser Gln Ser Pro Val Arg Ala Pro Arg Ala Ala Arg
        250                 255                 260

CCA CTG AAG AGG AGG CAG CCA AAG AAA ACG AAC GAG CTT CCG CAC CCC        929
Pro Leu Lys Arg Arg Gln Pro Lys Lys Thr Asn Glu Leu Pro His Pro
    265                 270                 275

AAC AAA CTC CCA GGG ATC TTT GAT GAT GGC CAC GGT TCC CGC GGC AGA        977
Asn Lys Leu Pro Gly Ile Phe Asp Asp Gly His Gly Ser Arg Gly Arg
280                 285                 290                 295

GAG GTT TGC CGC AGG CAT GAG CTC TAC GTC AGC TTC CGT GAC CTT GGC       1025
Glu Val Cys Arg Arg His Glu Leu Tyr Val Ser Phe Arg Asp Leu Gly
```

```
                    300               305               310
TGG CTG GAC TGG GTC ATC GCC CCC CAG GGC TAC TCT GCC TAT TAC TGT       1073
Trp Leu Asp Trp Val Ile Ala Pro Gln Gly Tyr Ser Ala Tyr Tyr Cys
            315               320               325

GAG GGG GAG TGT GCT TTC CCA CTG GAC TCC TGT ATG AAC GCC ACC AAC       1121
Glu Gly Glu Cys Ala Phe Pro Leu Asp Ser Cys Met Asn Ala Thr Asn
        330               335               340

CAT GCC ATC TTG CAG TCT CTG GTG CAC CTG ATG AAG CCA GAT GTT GTC       1169
His Ala Ile Leu Gln Ser Leu Val His Leu Met Lys Pro Asp Val Val
    345               350               355

CCC AAG GCA TGC TGT GCA CCC ACC AAA CTG AGT GCC ACC TCT GTG CTG       1217
Pro Lys Ala Cys Cys Ala Pro Thr Lys Leu Ser Ala Thr Ser Val Leu
360               365               370               375

TAC TAT GAC AGC AGC AAC AAT GTC ATC CTG CGT AAA CAC CGT AAC ATG       1265
Tyr Tyr Asp Ser Ser Asn Asn Val Ile Leu Arg Lys His Arg Asn Met
            380               385               390

GTG GTC AAG GCC TGT GGC TGC CAC TGAGGCCCCG CCCAGCATCC TGCTTCTACT      1319
Val Val Lys Ala Cys Gly Cys His
        395

ACCTTACCAT CTGGCCGGGC CCCTCTCCAG AGGCAGAAAC CCTTCTATGT TATCATAGCT     1379

CAGACAGGGG CAATGGGAGG CCCTTCACTT CCCCTGGCCA CTTCCTGCTA AAATTCTGGT     1439

CTTTCCCAGT TCCTCTGTCC TTCATGGGGT TTCGGGGCTA TCACCCCGCC CTCTCCATCC     1499

TCCTACCCCA AGCATAGACT GAATGCACAC AGCATCCCAG AGCTATGCTA ACTGAGAGGT     1559

CTGGGGTCAG CACTGAAGGC CCACATGAGG AAGACTGATC CTTGGCCATC CTCAGCCCAC     1619

AATGGCAAAT TCTGGATGGT CTAAGAAGGC CGTGGAATTC TAAACTAGAT GATCTGGGCT     1679

CTCTGCACCA TTCATTGTGG CAGTTGGGAC ATTTTTAGGT ATAACAGACA CATACACTTA     1739

GATCAATGCA TCGCTGTACT CCTTGAAATC AGAGCTAGCT TGTTAGAAAA AGAATCAGAG     1799

CCAGGTATAG CGGTGCATGT CATTAATCCC AGCGCTAAAG AGACAGAGAC AGGAGAATCT     1859

CTGTGAGTTC AAGGCCACAT AGAAAGAGCC TGTCTCGGGA GCAGGAAAAA AAAAAAAAC      1919

GGAATTC                                                              1926

(2) INFORMATION FOR SEQ ID NO:23:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO:23:

Met Ala Met Arg Pro Gly Pro Leu Trp Leu Leu Gly Leu Ala Leu Cys
 1               5                   10                  15

Ala Leu Gly Gly Gly His Gly Pro Arg Pro Pro His Thr Cys Pro Gln
                20                  25                  30

Arg Arg Leu Gly Ala Arg Glu Arg Arg Asp Met Gln Arg Glu Ile Leu
            35                  40                  45

Ala Val Leu Gly Leu Pro Gly Arg Pro Arg Pro Arg Ala Gln Pro Ala
        50                  55                  60

Ala Ala Arg Gln Pro Ala Ser Ala Pro Leu Phe Met Leu Asp Leu Tyr
65                  70                  75                  80

His Ala Met Thr Asp Asp Asp Gly Gly Pro Pro Gln Ala His Leu
                85                  90                  95

Gly Arg Ala Asp Leu Val Met Ser Phe Val Asn Met Val Glu Arg Asp
```

```
                100                 105                 110
Arg Thr Leu Gly Tyr Gln Glu Pro His Trp Lys Glu Phe His Phe Asp
        115                 120                 125

Leu Thr Gln Ile Pro Ala Gly Glu Ala Val Thr Ala Ala Glu Phe Arg
    130                 135                 140

Ile Tyr Lys Glu Pro Ser Thr His Pro Leu Asn Thr Leu His Ile
145                 150                 155                 160

Ser Met Phe Glu Val Val Gln Glu His Ser Asn Arg Glu Ser Asp Leu
                165                 170                 175

Phe Phe Leu Asp Leu Gln Thr Leu Arg Ser Gly Asp Glu Gly Trp Leu
            180                 185                 190

Val Leu Asp Ile Thr Ala Ala Ser Asp Arg Trp Leu Leu Asn His His
        195                 200                 205

Lys Asp Leu Gly Leu Arg Leu Tyr Val Glu Thr Ala Asp Gly His Ser
    210                 215                 220

Met Asp Pro Gly Leu Ala Gly Leu Leu Gly Arg Gln Ala Pro Arg Ser
225                 230                 235                 240

Arg Gln Pro Phe Met Val Thr Phe Phe Arg Ala Ser Gln Ser Pro Val
                245                 250                 255

Arg Ala Pro Arg Ala Ala Arg Pro Leu Lys Arg Arg Gln Pro Lys Lys
            260                 265                 270

Thr Asn Glu Leu Pro His Pro Asn Lys Leu Pro Gly Ile Phe Asp Asp
        275                 280                 285

Gly His Gly Ser Arg Gly Arg Glu Val Cys Arg Arg His Glu Leu Tyr
    290                 295                 300

Val Ser Phe Arg Asp Leu Gly Trp Leu Asp Trp Val Ile Ala Pro Gln
305                 310                 315                 320

Gly Tyr Ser Ala Tyr Tyr Cys Glu Gly Glu Cys Ala Phe Pro Leu Asp
                325                 330                 335

Ser Cys Met Asn Ala Thr Asn His Ala Ile Leu Gln Ser Leu Val His
            340                 345                 350

Leu Met Lys Pro Asp Val Val Pro Lys Ala Cys Cys Ala Pro Thr Lys
        355                 360                 365

Leu Ser Ala Thr Ser Val Leu Tyr Tyr Asp Ser Ser Asn Asn Val Ile
    370                 375                 380

Leu Arg Lys His Arg Asn Met Val Val Lys Ala Cys Gly Cys His
385                 390                 395

(2) INFORMATION FOR SEQ ID NO:24:

(i) SEQUENCE CHARACTERISTICS:
        (A) LENGTH: 1368 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1365

(xi) SEQUENCE DESCRIPTION: SEQ ID NO:24:

ATG TCG GGA CTG CGA AAC ACC TCG GAG GCC GTT GCA GTG CTC GCC TCC      48
Met Ser Gly Leu Arg Asn Thr Ser Glu Ala Val Ala Val Leu Ala Ser
  1               5                  10                  15

CTG GGA CTC GGA ATG GTT CTG CTC ATG TTC GTG GCG ACC ACG CCG CCG      96
Leu Gly Leu Gly Met Val Leu Leu Met Phe Val Ala Thr Thr Pro Pro
```

-continued

```
                20                      25                      30
GCC GTT GAG GCC ACC CAG TCG GGG ATT TAC ATA GAC AAC GGC AAG GAC      144
Ala Val Glu Ala Thr Gln Ser Gly Ile Tyr Ile Asp Asn Gly Lys Asp
             35                      40                      45

CAG ACG ATC ATG CAC AGA GTG CTG AGC GAG GAC GAC AAG CTG GAC GTC      192
Gln Thr Ile Met His Arg Val Leu Ser Glu Asp Asp Lys Leu Asp Val
         50                      55                      60

TCG TAC GAG ATC CTC GAG TTC CTG GGC ATC GCC GAA CGG CCG ACG CAC      240
Ser Tyr Glu Ile Leu Glu Phe Leu Gly Ile Ala Glu Arg Pro Thr His
 65                      70                      75                      80

CTG AGC AGC CAC CAG TTG TCG CTG AGG AAG TCG GCT CCC AAG TTC CTG      288
Leu Ser Ser His Gln Leu Ser Leu Arg Lys Ser Ala Pro Lys Phe Leu
                     85                      90                      95

CTG GAC GTC TAC CAC CGC ATC ACG GCG GAG GAG GGT CTC AGC GAT CAG      336
Leu Asp Val Tyr His Arg Ile Thr Ala Glu Glu Gly Leu Ser Asp Gln
                 100                     105                     110

GAT GAG GAC GAC GAC TAC GAA CGC GGC CAT CGG TCC AGG AGG AGC GCC      384
Asp Glu Asp Asp Asp Tyr Glu Arg Gly His Arg Ser Arg Arg Ser Ala
             115                     120                     125

GAC CTC GAG GAG GAT GAG GGC GAG CAG CAG AAG AAC TTC ATC ACC GAC      432
Asp Leu Glu Glu Asp Glu Gly Glu Gln Gln Lys Asn Phe Ile Thr Asp
         130                     135                     140

CTG GAC AAG CGG GCC ATC GAC GAG AGC GAC ATC ATC ATG ACC TTC CTG      480
Leu Asp Lys Arg Ala Ile Asp Glu Ser Asp Ile Ile Met Thr Phe Leu
145                     150                     155                     160

AAC AAG CGC CAC CAC AAT GTG GAC GAA CTG CGT CAC GAG CAC GGC CGT      528
Asn Lys Arg His His Asn Val Asp Glu Leu Arg His Glu His Gly Arg
                     165                     170                     175

CGC CTG TGG TTC GAC GTC TCC AAC GTG CCC AAC GAC AAC TAC CTG GTG      576
Arg Leu Trp Phe Asp Val Ser Asn Val Pro Asn Asp Asn Tyr Leu Val
                 180                     185                     190

ATG GCC GAG CTG CGC ATC TAT CAG AAC GCC AAC GAG GGC AAG TGG CTG      624
Met Ala Glu Leu Arg Ile Tyr Gln Asn Ala Asn Glu Gly Lys Trp Leu
             195                     200                     205

ACC GCC AAC AGG GAG TTC ACC ATC ACG GTA TAC GCC ATT GGC ACC GGC      672
Thr Ala Asn Arg Glu Phe Thr Ile Thr Val Tyr Ala Ile Gly Thr Gly
         210                     215                     220

ACG CTG GGC CAG CAC ACC ATG GAG CCG CTG TCC TCG GTG AAC ACC ACC      720
Thr Leu Gly Gln His Thr Met Glu Pro Leu Ser Ser Val Asn Thr Thr
225                     230                     235                     240

GGG GAC TAC GTG GGC TGG TTG GAG CTC AAC GTG ACC GAG GGC CTG CAC      768
Gly Asp Tyr Val Gly Trp Leu Glu Leu Asn Val Thr Glu Gly Leu His
                     245                     250                     255

GAG TGG CTG GTC AAG TCG AAG GAC AAT CAT GGC ATC TAC ATT GGA GCA      816
Glu Trp Leu Val Lys Ser Lys Asp Asn His Gly Ile Tyr Ile Gly Ala
                 260                     265                     270

CAC GCT GTC AAC CGA CCC GAC CGC GAG GTG AAG CTG GAC GAC ATT GGA      864
His Ala Val Asn Arg Pro Asp Arg Glu Val Lys Leu Asp Asp Ile Gly
             275                     280                     285

CTG ATC CAC CGC AAG GTG GAC GAC GAG TTC CAG CCC TTC ATG ATC GGC      912
Leu Ile His Arg Lys Val Asp Asp Glu Phe Gln Pro Phe Met Ile Gly
         290                     295                     300

TTC TTC CGC GGA CCG GAG CTG ATC AAG GCG ACG GCC CAC AGC AGC CAC      960
Phe Phe Arg Gly Pro Glu Leu Ile Lys Ala Thr Ala His Ser Ser His
305                     310                     315                     320

CAC AGG AGC AAG CGA AGC GCC AGC CAT CCA CGC AAG CGC AAG AAG TCG     1008
His Arg Ser Lys Arg Ser Ala Ser His Pro Arg Lys Arg Lys Lys Ser
                     325                     330                     335

GTG TCG CCC AAC AAC GTG CCG CTG CTG GAA CCG ATG GAG AGC ACG CGC     1056
```

```
Val Ser Pro Asn Asn Val Pro Leu Leu Glu Pro Met Glu Ser Thr Arg
            340                 345                 350

AGC TGC CAG ATG CAG ACC CTG TAC ATA GAC TTC AAG GAT CTG GGC TGG      1104
Ser Cys Gln Met Gln Thr Leu Tyr Ile Asp Phe Lys Asp Leu Gly Trp
        355                 360                 365

CAT GAC TGG ATC ATC GCA CCA GAG GGC TAT GGC GCC TTC TAC TGC AGC      1152
His Asp Trp Ile Ile Ala Pro Glu Gly Tyr Gly Ala Phe Tyr Cys Ser
370                 375                 380

GGC GAG TGC AAT TTC CCG CTC AAT GCG CAC ATG AAC GCC ACG AAC CAT      1200
Gly Glu Cys Asn Phe Pro Leu Asn Ala His Met Asn Ala Thr Asn His
385                 390                 395                 400

GCG ATC GTC CAG ACC CTG GTC CAC CTG CTG GAG CCC AAG AAG GTG CCC      1248
Ala Ile Val Gln Thr Leu Val His Leu Leu Glu Pro Lys Lys Val Pro
            405                 410                 415

AAG CCC TGC TGC GCT CCG ACC AGG CTG GGA GCA CTA CCC GTT CTG TAC      1296
Lys Pro Cys Cys Ala Pro Thr Arg Leu Gly Ala Leu Pro Val Leu Tyr
            420                 425                 430

CAC CTG AAC GAC GAG AAT GTG AAC CTG AAA AAG TAT AGA AAC ATG ATT      1344
His Leu Asn Asp Glu Asn Val Asn Leu Lys Lys Tyr Arg Asn Met Ile
            435                 440                 445

GTG AAA TCC TGC GGG TGC CAT TGA                                      1368
Val Lys Ser Cys Gly Cys His
    450                 455

(2) INFORMATION FOR SEQ ID NO:25:

(i) SEQUENCE CHARACTERISTICS:
        (A) LENGTH: 455 amino acids
        (B) TYPE: amino acid
        (D) TOPOLOGY: linear (ii) MOLECULE TYPE: protein (xi) SEQUENCE DESCRIPTION: SEQ ID NO:25:

Met Ser Gly Leu Arg Asn Thr Ser Glu Ala Val Ala Val Leu Ala Ser
 1               5                  10                  15

Leu Gly Leu Gly Met Val Leu Leu Met Phe Val Ala Thr Thr Pro Pro
                20                  25                  30

Ala Val Glu Ala Thr Gln Ser Gly Ile Tyr Ile Asp Asn Gly Lys Asp
            35                  40                  45

Gln Thr Ile Met His Arg Val Leu Ser Glu Asp Asp Lys Leu Asp Val
        50                  55                  60

Ser Tyr Glu Ile Leu Glu Phe Leu Gly Ile Ala Glu Arg Pro Thr His
65                  70                  75                  80

Leu Ser Ser His Gln Leu Ser Leu Arg Lys Ser Ala Pro Lys Phe Leu
                85                  90                  95

Leu Asp Val Tyr His Arg Ile Thr Ala Glu Glu Gly Leu Ser Asp Gln
            100                 105                 110

Asp Glu Asp Asp Asp Tyr Glu Arg Gly His Arg Ser Arg Arg Ser Ala
        115                 120                 125

Asp Leu Glu Glu Asp Glu Gly Gln Gln Lys Asn Phe Ile Thr Asp
        130                 135                 140

Leu Asp Lys Arg Ala Ile Asp Glu Ser Asp Ile Ile Met Thr Phe Leu
145                 150                 155                 160

Asn Lys Arg His His Asn Val Asp Glu Leu Arg His Glu His Gly Arg
                165                 170                 175

Arg Leu Trp Phe Asp Val Ser Asn Val Pro Asn Asp Asn Tyr Leu Val
            180                 185                 190
```

-continued

```
Met Ala Glu Leu Arg Ile Tyr Gln Asn Ala Asn Glu Gly Lys Trp Leu
        195                 200                 205

Thr Ala Asn Arg Glu Phe Thr Ile Thr Val Tyr Ala Ile Gly Thr Gly
    210                 215                 220

Thr Leu Gly Gln His Thr Met Glu Pro Leu Ser Ser Val Asn Thr Thr
225                 230                 235                 240

Gly Asp Tyr Val Gly Trp Leu Glu Leu Asn Val Thr Glu Gly Leu His
                245                 250                 255

Glu Trp Leu Val Lys Ser Lys Asp Asn His Gly Ile Tyr Ile Gly Ala
                260                 265                 270

His Ala Val Asn Arg Pro Asp Arg Glu Val Lys Leu Asp Asp Ile Gly
        275                 280                 285

Leu Ile His Arg Lys Val Asp Asp Glu Phe Gln Pro Phe Met Ile Gly
    290                 295                 300

Phe Phe Arg Gly Pro Glu Leu Ile Lys Ala Thr Ala His Ser Ser His
305                 310                 315                 320

His Arg Ser Lys Arg Ser Ala Ser His Pro Arg Lys Arg Lys Lys Ser
                325                 330                 335

Val Ser Pro Asn Asn Val Pro Leu Leu Glu Pro Met Glu Ser Thr Arg
        340                 345                 350

Ser Cys Gln Met Gln Thr Leu Tyr Ile Asp Phe Lys Asp Leu Gly Trp
    355                 360                 365

His Asp Trp Ile Ile Ala Pro Glu Gly Tyr Gly Ala Phe Tyr Cys Ser
370                 375                 380

Gly Glu Cys Asn Phe Pro Leu Asn Ala His Met Asn Ala Thr Asn His
385                 390                 395                 400

Ala Ile Val Gln Thr Leu Val His Leu Leu Glu Pro Lys Lys Val Pro
                405                 410                 415

Lys Pro Cys Cys Ala Pro Thr Arg Leu Gly Ala Leu Pro Val Leu Tyr
        420                 425                 430

His Leu Asn Asp Glu Asn Val Asn Leu Lys Lys Tyr Arg Asn Met Ile
    435                 440                 445

Val Lys Ser Cys Gly Cys His
450                 455

(2) INFORMATION FOR SEQ ID NO:26:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..104
        (D) OTHER INFORMATION: /label= BMP3

(xi) SEQUENCE DESCRIPTION: SEQ ID NO:26:

Cys Ala Arg Arg Tyr Leu Lys Val Asp Phe Ala Asp Ile Gly Trp Ser
1               5                   10                  15

Glu Trp Ile Ile Ser Pro Lys Ser Phe Asp Ala Tyr Tyr Cys Ser Gly
                20                  25                  30

Ala Cys Gln Phe Pro Met Pro Lys Ser Leu Lys Pro Ser Asn His Ala
            35                  40                  45

Thr Ile Gln Ser Ile Val Ala Arg Ala Val Gly Val Val Pro Gly Ile
```

```
                  50                  55                  60
Pro Glu Pro Cys Cys Val Pro Glu Lys Met Ser Ser Leu Ser Ile Leu
 65                  70                  75                  80

Phe Phe Asp Glu Asn Lys Asn Val Val Leu Lys Val Tyr Pro Asn Met
                 85                  90                  95

Thr Val Glu Ser Cys Ala Cys Arg
                100

(2) INFORMATION FOR SEQ ID NO:27:

(i) SEQUENCE CHARACTERISTICS:
         (A) LENGTH: 102 amino acids
         (B) TYPE: amino acid
         (C) STRANDEDNESS: single
         (D) TOPOLOGY: linear (ii) MOLECULE TYPE: protein (ix) FEATURE:
         (A) NAME/KEY: Protein
         (B) LOCATION: 1..102
         (D) OTHER INFORMATION: /label= BMP5

(xi) SEQUENCE DESCRIPTION: SEQ ID NO:27:

Cys Lys Lys His Glu Leu Tyr Val Ser Phe Arg Asp Leu Gly Trp Gln
 1                   5                  10                  15

Asp Trp Ile Ile Ala Pro Glu Gly Tyr Ala Ala Phe Tyr Cys Asp Gly
                 20                  25                  30

Glu Cys Ser Phe Pro Leu Asn Ala His Met Asn Ala Thr Asn His Ala
                 35                  40                  45

Ile Val Gln Thr Leu Val His Leu Met Phe Pro Asp His Val Pro Lys
 50                  55                  60

Pro Cys Cys Ala Pro Thr Lys Leu Asn Ala Ile Ser Val Leu Tyr Phe
 65                  70                  75                  80

Asp Asp Ser Ser Asn Val Ile Leu Lys Lys Tyr Arg Asn Met Val Val
                 85                  90                  95

Arg Ser Cys Gly Cys His
                100

(2) INFORMATION FOR SEQ ID NO:28:

(i) SEQUENCE CHARACTERISTICS:
         (A) LENGTH: 102 amino acids
         (B) TYPE: amino acid
         (C) STRANDEDNESS: single
         (D) TOPOLOGY: linear (ii) MOLECULE TYPE: protein (ix) FEATURE:
         (A) NAME/KEY: Protein
         (B) LOCATION: 1..102
         (D) OTHER INFORMATION: /label= BMP6

(xi) SEQUENCE DESCRIPTION: SEQ ID NO:28:

Cys Arg Lys His Glu Leu Tyr Val Ser Phe Gln Asp Leu Gly Trp Gln
 1                   5                  10                  15

Asp Trp Ile Ile Ala Pro Lys Gly Tyr Ala Ala Asn Tyr Cys Asp Gly
                 20                  25                  30

Glu Cys Ser Phe Pro Leu Asn Ala His Met Asn Ala Thr Asn His Ala
                 35                  40                  45

Ile Val Gln Thr Leu Val His Leu Met Asn Pro Glu Tyr Val Pro Lys
 50                  55                  60
```

```
Pro Cys Cys Ala Pro Thr Lys Leu Asn Ala Ile Ser Val Leu Tyr Phe
 65                  70                  75                  80

Asp Asp Asn Ser Asn Val Ile Leu Lys Lys Tyr Arg Trp Met Val Val
                 85                  90                  95

Arg Ala Cys Gly Cys His
                100
```

(2) INFORMATION FOR SEQ ID NO:29:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= OPX
            /note= "WHEREIN XAA AT EACH POS'N IS INDEPENDENTLY
            SELECTED FROM THE RESIDUES OCCURING AT THE CORRESPONDING
            POS'N IN THE C-TERMINAL SEQUENCE OF MOUSE OR HUMAN OP1 OR
            OP2 (SEQ. ID NOS. 5,6,7&8 OR 16,18, 20&22"

(xi) SEQUENCE DESCRIPTION: SEQ ID NO:29:

```
Cys Xaa Xaa His Glu Leu Tyr Val Xaa Phe Xaa Asp Leu Gly Trp Xaa
 1               5                  10                  15

Asp Trp Xaa Ile Ala Pro Xaa Gly Tyr Xaa Ala Tyr Tyr Cys Glu Gly
                 20                  25                  30

Glu Cys Xaa Phe Pro Leu Xaa Ser Xaa Met Asn Ala Thr Asn His Ala
                 35                  40                  45

Ile Xaa Gln Xaa Leu Val His Xaa Xaa Xaa Pro Xaa Xaa Val Pro Lys
     50                  55                  60

Xaa Cys Cys Ala Pro Thr Xaa Leu Xaa Ala Xaa Ser Val Leu Tyr Xaa
 65                  70                  75                  80

Asp Xaa Ser Xaa Asn Val Xaa Leu Xaa Lys Xaa Arg Asn Met Val Val
                 85                  90                  95

Xaa Ala Cys Gly Cys His
                100
```

(2) INFORMATION FOR SEQ ID NO:30:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= GENERIC-SEQ-5
            /note= "WHEREIN EACH XAA IS INDEPENDENTLY SELECTED FROM A
            GROUP OF ONE OR MORE SPECIFIED AMINO ACIDS AS DEFINED IN
            THE SPECIFICATION"

(xi) SEQUENCE DESCRIPTION: SEQ ID NO:30:

```
Leu Xaa Xaa Xaa Phe Xaa Xaa Xaa Gly Trp Xaa Xaa Trp Xaa Xaa Xaa
 1               5                  10                  15

Pro Xaa Xaa Xaa Xaa Ala Xaa Tyr Cys Xaa Gly Xaa Cys Xaa Xaa Pro
                 20                  25                  30
```

```
Xaa Xaa Xaa Xaa Xaa Xaa Xaa Asn His Ala Xaa Xaa Xaa Xaa
        35                  40              45

Xaa Xaa Xaa Xaa Xaa Xaa Xaa Xaa Xaa Xaa Xaa Cys Cys Xaa Pro
    50                  55              60

Xaa Xaa Xaa Xaa Xaa Xaa Xaa Xaa Leu Xaa Xaa Xaa Xaa Xaa Xaa
65              70                  75                  80

Val Xaa Leu Xaa Xaa Xaa Xaa Xaa Met Xaa Val Xaa Xaa Cys Xaa Cys
            85                  90                  95

Xaa
```

(2) INFORMATION FOR SEQ ID NO:31:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= GENERIC-SEQ-6
            /note= "WHEREIN EACH XAA IS INDEPENDENTLY SELECTED FROM A
            GROUP OF ONE OR MORE SPECIFIED AMINO ACIDS AS DEFINED IN
            THE SPECIFICATION"

(xi) SEQUENCE DESCRIPTION: SEQ ID NO:31:

```
Cys Xaa Xaa Xaa Xaa Leu Xaa Xaa Xaa Phe Xaa Xaa Xaa Gly Trp Xaa
1               5                   10                  15

Xaa Trp Xaa Xaa Xaa Pro Xaa Xaa Xaa Xaa Ala Xaa Tyr Cys Xaa Gly
            20                  25                  30

Xaa Cys Xaa Xaa Pro Xaa Xaa Xaa Xaa Xaa Xaa Xaa Xaa Asn His Ala
        35                  40                  45

Xaa Xaa Xaa Xaa Xaa Xaa Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Xaa Leu Xaa Xaa
65              70                  75                  80

Xaa Xaa Xaa Xaa Xaa Val Xaa Leu Xaa Xaa Xaa Xaa Xaa Met Xaa Val
                85                  90                  95

Xaa Xaa Cys Xaa Cys Xaa
            100
```

(2) INFORMATION FOR SEQ ID NO:32:

(i) SEQUENCE CHARACTERISTICS:
        (A) LENGTH: 1247 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 84..1199
        (D) OTHER INFORMATION: /product= "GDF-1"

(xi) SEQUENCE DESCRIPTION: SEQ ID NO:32:

```
GGGGACACCG GCCCCGCCCT CAGCCCACTG GTCCCGGGCC GCCGCGGACC CTGCGCACTC         60

TCTGGTCATC GCCTGGGAGG AAG ATG CCA CCG CCG CAG CAA GGT CCC TGC           110
                         Met Pro Pro Pro Gln Gln Gly Pro Cys
```

-continued

```
                    1               5
GGC CAC CAC CTC CTC CTC CTC CTG GCC CTG CTG CTG CCC TCG CTG CCC        158
Gly His His Leu Leu Leu Leu Leu Ala Leu Leu Leu Pro Ser Leu Pro
 10              15                  20                  25

CTG ACC CGC GCC CCC GTG CCC CCA GGC CCA GCC GCC GCC CTG CTC CAG        206
Leu Thr Arg Ala Pro Val Pro Pro Gly Pro Ala Ala Ala Leu Leu Gln
             30                  35                  40

GCT CTA GGA CTG CGC GAT GAG CCC CAG GGT GCC CCC AGG CTC CGG CCG        254
Ala Leu Gly Leu Arg Asp Glu Pro Gln Gly Ala Pro Arg Leu Arg Pro
                 45                  50                  55

GTT CCC CCG GTC ATG TGG CGC CTG TTT CGA CGC CGG GAC CCC CAG GAG        302
Val Pro Pro Val Met Trp Arg Leu Phe Arg Arg Arg Asp Pro Gln Glu
             60                  65                  70

ACC AGG TCT GGC TCG CGG CGG ACG TCC CCA GGG GTC ACC CTG CAA CCG        350
Thr Arg Ser Gly Ser Arg Arg Thr Ser Pro Gly Val Thr Leu Gln Pro
     75                  80                  85

TGC CAC GTG GAG GAG CTG GGG GTC GCC GGA AAC ATC GTG CGC CAC ATC        398
Cys His Val Glu Glu Leu Gly Val Ala Gly Asn Ile Val Arg His Ile
 90                  95                 100                 105

CCG GAC CGC GGT GCG CCC ACC CGG GCC TCG GAG CCT GTC TCG GCC GCG        446
Pro Asp Arg Gly Ala Pro Thr Arg Ala Ser Glu Pro Val Ser Ala Ala
                110                 115                 120

GGG CAT TGC CCT GAG TGG ACA GTC GTC TTC GAC CTG TCG GCT GTG GAA        494
Gly His Cys Pro Glu Trp Thr Val Val Phe Asp Leu Ser Ala Val Glu
                125                 130                 135

CCC GCT GAG CGC CCG AGC CGG GCC CGC CTG GAG CTG CGT TTC GCG GCG        542
Pro Ala Glu Arg Pro Ser Arg Ala Arg Leu Glu Leu Arg Phe Ala Ala
                140                 145                 150

GCG GCG GCG GCA GCC CCG GAG GGC GGC TGG GAG CTG AGC GTG GCG CAA        590
Ala Ala Ala Ala Ala Pro Glu Gly Gly Trp Glu Leu Ser Val Ala Gln
        155                 160                 165

GCG GGC CAG GGC GCG GGC GCG GAC CCC GGG CCG GTG CTG CTC CGC CAG        638
Ala Gly Gln Gly Ala Gly Ala Asp Pro Gly Pro Val Leu Leu Arg Gln
170                 175                 180                 185

TTG GTG CCC GCC CTG GGG CCG CCA GTG CGC GCG GAG CTG CTG GGC GCC        686
Leu Val Pro Ala Leu Gly Pro Pro Val Arg Ala Glu Leu Leu Gly Ala
                190                 195                 200

GCT TGG GCT CGC AAC GCC TCA TGG CCG CGC AGC CTC CGC CTG GCG CTG        734
Ala Trp Ala Arg Asn Ala Ser Trp Pro Arg Ser Leu Arg Leu Ala Leu
                205                 210                 215

GCG CTA CGC CCC CGG GCC CCT GCC GCC TGC GCG CGC CTG GCC GAG GCC        782
Ala Leu Arg Pro Arg Ala Pro Ala Ala Cys Ala Arg Leu Ala Glu Ala
            220                 225                 230

TCG CTG CTG CTG GTG ACC CTC GAC CCG CGC CTG TGC CAC CCC CTG GCC        830
Ser Leu Leu Leu Val Thr Leu Asp Pro Arg Leu Cys His Pro Leu Ala
        235                 240                 245

CGG CCG CGG CGC GAC GCC GAA CCC GTG TTG GGC GGC GGC CCC GGG GGC        878
Arg Pro Arg Arg Asp Ala Glu Pro Val Leu Gly Gly Gly Pro Gly Gly
250                 255                 260                 265

GCT TGT CGC GCG CGG CGG CTG TAC GTG AGC TTC CGC GAG GTG GGC TGG        926
Ala Cys Arg Ala Arg Arg Leu Tyr Val Ser Phe Arg Glu Val Gly Trp
                270                 275                 280

CAC CGC TGG GTC ATC GCG CCG CGC GGC TTC CTG GCC AAC TAC TGC CAG        974
His Arg Trp Val Ile Ala Pro Arg Gly Phe Leu Ala Asn Tyr Cys Gln
                285                 290                 295

GGT CAG TGC GCG CTG CCC GTC GCG CTG TCG GGG TCC GGG GGG CCG CCG       1022
Gly Gln Cys Ala Leu Pro Val Ala Leu Ser Gly Ser Gly Gly Pro Pro
                300                 305                 310

GCG CTC AAC CAC GCT GTG CTG CGC GCG CTC ATG CAC GCG GCC GCC CCG       1070
```

```
          Ala Leu Asn His Ala Val Leu Arg Ala Leu Met His Ala Ala Ala Pro
              315                 320                 325

GGA GCC GCC GAC CTG CCC TGC TGC GTG CCC GCG CGC CTG TCG CCC ATC         1118
Gly Ala Ala Asp Leu Pro Cys Cys Val Pro Ala Arg Leu Ser Pro Ile
330                 335                 340                 345

TCC GTG CTC TTC TTT GAC AAC AGC GAC AAC GTG GTG CTG CGG CAG TAT         1166
Ser Val Leu Phe Phe Asp Asn Ser Asp Asn Val Val Leu Arg Gln Tyr
                350                 355                 360

GAG GAC ATG GTG GTG GAC GAG TGC GGC TGC CGC TAACCCGGGG CGGGCAGGGA       1219
Glu Asp Met Val Val Asp Glu Cys Gly Cys Arg
                365                 370

CCCGGGCCCA ACAATAAATG CCGCGTGG                                          1247

(2) INFORMATION FOR SEQ ID NO:33:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:33:

Met Pro Pro Gln Gln Gly Pro Cys Gly His His Leu Leu Leu Leu
 1               5                  10                  15

Leu Ala Leu Leu Leu Pro Ser Leu Pro Leu Thr Arg Ala Pro Val Pro
                20                  25                  30

Pro Gly Pro Ala Ala Ala Leu Leu Gln Ala Leu Gly Leu Arg Asp Glu
                35                  40                  45

Pro Gln Gly Ala Pro Arg Leu Arg Pro Val Pro Pro Val Met Trp Arg
    50                  55                  60

Leu Phe Arg Arg Arg Asp Pro Gln Glu Thr Arg Ser Gly Ser Arg Arg
65                  70                  75                  80

Thr Ser Pro Gly Val Thr Leu Gln Pro Cys His Val Glu Glu Leu Gly
                85                  90                  95

Val Ala Gly Asn Ile Val Arg His Ile Pro Asp Arg Gly Ala Pro Thr
                100                 105                 110

Arg Ala Ser Glu Pro Val Ser Ala Ala Gly His Cys Pro Glu Trp Thr
            115                 120                 125

Val Val Phe Asp Leu Ser Ala Val Glu Pro Ala Glu Arg Pro Ser Arg
    130                 135                 140

Ala Arg Leu Glu Leu Arg Phe Ala Ala Ala Ala Ala Ala Pro Glu
145                 150                 155                 160

Gly Gly Trp Glu Leu Ser Val Ala Gln Ala Gly Gln Gly Ala Gly Ala
                165                 170                 175

Asp Pro Gly Pro Val Leu Leu Arg Gln Leu Val Pro Ala Leu Gly Pro
            180                 185                 190

Pro Val Arg Ala Glu Leu Leu Gly Ala Ala Trp Ala Arg Asn Ala Ser
        195                 200                 205

Trp Pro Arg Ser Leu Arg Leu Ala Leu Ala Leu Arg Pro Arg Ala Pro
    210                 215                 220

Ala Ala Cys Ala Arg Leu Ala Glu Ala Ser Leu Leu Leu Val Thr Leu
225                 230                 235                 240

Asp Pro Arg Leu Cys His Pro Leu Ala Arg Pro Arg Arg Asp Ala Glu
                245                 250                 255

Pro Val Leu Gly Gly Pro Gly Gly Ala Cys Arg Ala Arg Arg Leu
                260                 265                 270
```

```
                                    -continued

Tyr Val Ser Phe Arg Glu Val Gly Trp His Arg Trp Val Ile Ala Pro
        275                 280                 285

Arg Gly Phe Leu Ala Asn Tyr Cys Gln Gly Gln Cys Ala Leu Pro Val
        290                 295                 300

Ala Leu Ser Gly Ser Gly Gly Pro Pro Ala Leu Asn His Ala Val Leu
305                     310                 315                 320

Arg Ala Leu Met His Ala Ala Ala Pro Gly Ala Ala Asp Leu Pro Cys
                325                 330                 335

Cys Val Pro Ala Arg Leu Ser Pro Ile Ser Val Leu Phe Phe Asp Asn
            340                 345                 350

Ser Asp Asn Val Val Leu Arg Gln Tyr Glu Asp Met Val Val Asp Glu
        355                 360                 365

Cys Gly Cys Arg
    370
```

MORPHOGEN-ENRICHED DIETARY COMPOSITION

CROSS REFERENCE TO RELAYED APPLICATIONS

This application is a continuation of Ser. No. 07/946,235, filed Sep. 16, 1992, now abandoned, which is continuation-in-part of (1) U.S. Ser. No. 07/922,813, filed Jul. 31, 1992, now abandoned which is a continuation-in-part of U.S. Ser. No. 07/752,764, filed Aug. 30, 1991, now abandoned, which in turn is a continuation in part of U.S. Ser. No. 07/667,274, filed Mar. 11, 1991, now abandoned; (2) U.S. Ser. No. 07/923,780, filed Jul. 31, 1992, now abandoned which is a continuation-in-part of U.S. Ser. No. 07/752,857, filed Aug. 30, 1991, now abandoned which in turn is a continuation-in-part of U.S. Ser. No. 07/667,274 filed Mar. 11, 1991, now abandoned; (3) U.S. Ser. No. 07/938,336 and U.S. Ser. No. 07/938,337, both, filed Aug. 28, 1992, both now abandoned and both continuations-in-part of U.S. Ser. No. 07/753,059, filed Aug. 30, 1991, now abandoned which in turn is a continuation-in-part of U.S. Ser. No. 07/667,274, filed Mar. 11, 1991, now abandoned; and (4) U.S. Ser. No. 07/752,764, filed Aug. 30, 1991, now abandoned which is a continuation-in-part of U.S. Ser. No. 07/667,274, filed Mar. 11, 1991, now abandoned. The disclosures of these applications are incorporated herein by reference. The disclosure of U.S. Ser. No. 07/946,238, filed Sep. 16, 1992, now abandoned, and currently pending as U.S. Ser. No. 08/445,468, filed May 22, 1995, now U.S. Pat. No. 5,849,686, is also incorporated herein by reference.

FIELD OF THE INVENTION

This invention relates generally to the field of dietary compositions and supplements.

BACKGROUND OF THE INVENTION

The present invention relates to compositions useful as mammalian dietary compositions and supplements. In particular, the invention relates to food additives and dietary supplements capable of enhancing tissue morphogenesis and development, particularly in individuals at risk for normal tissue development and viability. Examples of such individuals include infants, particularly prematurely-born ("preterm") and low birth weight infants, and juveniles; aged individuals; and individuals experiencing altered metabolic function and/or suffering from metabolic dysfunctions and other disorders that threaten organ or tissue function or viability, such as can result from malnutrition or starvation, autoimmune diseases, organ cirrhosis and other tissue necrotizing dysfunctions, or disorders associated with aging cells (cell senescence.)

Mammalian infants are nourished by mother's milk until such time as they can digest food solids. Infant formulas now exist for humans and other mammals which can supplant or supplement mother's milk. The formulas may be milk based (e.g., cow milk) or non-milk-based (e.g., soy). Particularly at risk are prematurely born infants whose tissues and organs are at an earlier stage of development, and whose nutritional requirements may differ from those of full term infants. Formula development is an ongoing endeavor to more accurately mimic the beneficial aspects of mother's milk. Nevertheless, despite the efforts of many researchers, infant formulas still differ in a number of significant ways from human milk. In part this is due because human milk has many substances, such as immunoglobulins, free amino acids, polyamines, nucleotides and polyunsaturated fatty acids not present, for example, in cow's milk. In addition, while infant formulas try to mimic the protein quantity found in human milk, the foreign proteins typically are present in the formula as hydrolysates to avoid rejection or reaction by the infant's digestive system. The proteins are present primarily as amino acid sources rather than as functional proteins as might normally be transmitted by the nursing mother to the infant. In addition, human milk may contain unidentified growth and differentiation factors that are important for overall tissue and skeletal development.

Another group of individuals with potentially unique nutritional requirements are individuals undergoing metabolic changes which may result from periods of intense growth or stress, including, for example, pregnant women and drowning victims. Other sources of stress to the body may result from malnutrition or starvation, or from metabolic disorders that affect organ viability, such as autoimmune disease and organ cirrhosis. Aged individuals, and postmenopausal women also have altered or slower metabolic function. All of these individuals are at risk for tissue damage or loss of tissue function due to altered metabolic function.

Reduced or lost tissue function due to malnutrition also is found in many patients admitted to hospitals (protein energy malnutrition, "PEM"). Proper nutritional support for such patients, while not a primary mode of treatment is, nevertheless, an important factor for therapy and recovery. It is, therefore important to administer a nutritionally balanced diet given orally, enterally or parenterally, adequate to the needs of the patient. This is especially true for those patients where conventional feeding is contraindicated (e.g., in dehydrated or gastroenterological patients) or is insufficient (e.g., in hypercatabolic patients). The enteral or oral mode of administration of foods typically is preferable to parenteral modes because of the lower morbidity, trophic effect upon the intestinal mucosa, reduced dependency on instrumentation and lower costs.

It is an object of this invention to provide dietary compositions and supplements for enhancing tissue morphogenesis, including tissue growth, development, maintenance and viability in a mammal, particularly a human. Another object of the invention is to provide an infant formula capable of enhancing tissue development in an infant or juvenile. Still another object is to provide an infant formula that more closely mimics a nursing mother's milk. Another object of the invention is to provide dietary supplements for individuals at risk for normal tissue development, growth, maintenance and viability, including premature infants, aged individuals and individuals with altered metabolic function and/or suffering from disorders or metabolic dysfunctions which threaten organ viability and function. These and other objects and features of the invention will be apparent from the description, drawings, and claims which follow.

SUMMARY OF THE INVENTION

The present invention provides compositions and methods useful in dietary applications and capable of enhancing tissue morphogenesis, including tissue growth, development, maintenance and viability in a mammal, particularly a human. The dietary compositions and supplements of this invention comprise a morphogenic protein ("morphogen"), as described herein, which, when provided to an individual as a food formulation or supplement, is capable of enhancing tissue development, growth, maintenance and/or viability in the individual. The compositions and processes provided herein are suitable for both infants and adults, and as part of clinical nutrition.

As used herein, "enhancing tissue viability" is understood to mean protecting tissue from lost or reduced tissue function due to cell damage or cell senescence, including inducing cells to maintain their differentiated phenotype, inducing regeneration of damaged tissue, and/or inhibiting additional damage thereto. "Morphogenically effective concentration" is understood to mean a concentration sufficient to enhance tissue development and tissue viability in an individual at risk for tissue damage and/or reduced or lost tissue function due to insufficient nutritional considerations, tissue damage associated therewith, and/or incomplete tissue development, regardless of etiology. The ability of morphogens to repair, regenerate and protect various disparate tissues, including but not limited to, tissues of the gastrointestinal tract, including the oral mucosa, liver tissue, dentin tissue, periodontal tissue, nerve tissue, bone tissue, and any tissue at risk of damage due to immune response-mediated tissue destruction, including ischemia-reperfusion related tissue damage are disposed in copending U.S. Ser. No. 07/945,286 filed Sep. 15, 1992, (currently pending as U.S. Ser. No. 08/461,397), U.S. Ser. No. 07/946,238, filed Sep. 16, 1992 (currently pending as U.S. Ser. No. 08/445,468), U.S. Ser. No. 07/752,764, filed Aug. 30, 1991 (currently pending as U.S. Ser. No. 08/404,113), U.S. Ser. No. 07/945,285, filed Sep. 15, 1992 (currently pending as U.S. Ser. No. 08/155, 343), U.S. Ser. No. 07/922,813, filed Jul. 31, 1992 (currently pending as U.S. Ser. No. 08/260,675), U.S. Ser. No. 07/923, 780, filed Jul. 31, 1992 (currently pending as U.S. Ser. No. 08/432,883), and U.S. Ser. No. 07/938,336, filed Aug. 2, 1992 (currently pending as U.S. Ser. No. 08/445,467), respectively, the disclosures of which are incorporated herein above by reference. "Morphogen-solubilizing molecule" is understood to mean a molecule capable of maintaining a morphogen in soluble form in physiologically buffered solutions. "Food formulation" is understood to mean a dietary composition normally ingested by an individual to satisfy the body's fundamental nutritional requirements; "dietary supplement" is understood to mean supplemental compositions ingested by an individual in addition to the food formulations ingested to satisfy the fundamental nutritional requirements. Multivitamin and iron tablets are examples of common dietary supplements. "Dietary composition" is understood to include both food formulations and dietary supplements. As used herein, the term "infant formula" is understood to refer to the well established infant compositions as defined by the American Academy of Pediatrics (AAP) and the AAP Committee on Nutrition ((1985) *Pediatrics* 75: 976, the European Society of Pediatric Gastroenterology and Nutrition (ESPGAN) and the ESPGAN Committee on Nutrition ((1987) *Acta Paed Scan Suppl:* 330), including recent updates published by these committees on infant formula nutritional guidelines.

The dietary composition or supplement preferably is administered orally, and may be provided in liquid form or as a powder to be dissolved in a beverage. Alternatively, the dietary supplement may be provided as a solid, e.g., in a capsular, tablet, troche or lozenge form; or, the supplement may be provided as an aerosol, for oral or nasal administration. Where oral administration is not possible or desirable, other administration routes are envisioned. For example, for some premature infants, or for intubated patients, parenteral administration may be required, e.g., via an enteral feeding tube.

The morphogen may be provided alone or in association with one or more suitable excipients or carriers, and/or in combination with other beneficial molecules such as vitamins, minerals, lipids, fiber sources and the like. The dietary supplements also may include pharmaceutically acceptable inert materials for use as binders or stabilizers, including magnesium stearate or calcium carbonate. The morphogen may be formulated together with one or more normal food ingredients, e.g., as part of a food formulation. Alternatively or, in addition, the morphogen may be provided as a dietary supplement in, for example, tablet or syrup form.

The mature form of the morphogen, or active truncated forms thereof which may be formulated in the composition, further may be provided in association with a morphogen precursor "pro" domain, which is known to enhance the solubility of the protein in physiologically buffered solutions. Other useful molecules known to enhance protein solubility include casein, including derivatives, salts and analogs thereof, as well as other milk components, and various serum and milk serum proteins. Additional useful molecules which may be associated with the morphogen include tissue targeting molecules capable of directing the morphogen to a desired target tissue. Tissue targeting molecules envisioned to be useful in the treatment protocols of this invention include antibodies, antibody fragments or other binding proteins which interact specifically with surface molecules on the target tissue cells.

Still another useful tissue targeting molecule may be part or all of a morphogen precursor "pro" domain. Morphogens may be synthesized in one tissue and secreted and transported to another tissue. For example, while the protein has been shown to be active in bone tissue, the primary source of OP-1 synthesis appears to be the tissue of the urogenic system (e.g., renal and bladder tissue), with secondary expression levels occurring in the brain, heart, lungs and gastrointestinal tract (GI tract, see below.) Moreover, the protein has been identified in serum, saliva and various milk forms. In addition, the secreted form of the protein comprises the mature dimer in association with the pro domain of the intact morphogen sequence. Accordingly, the associated morphogen pro domains may act to target specific morphogens to different tissues in vivo. As described below, morphogen species comprising the pro domain may be obtained from the culture medium of morphogen-secreting mammalian cells. Alternatively, a tissue-targeting species may be formulated by complexing the mature dimer (or an active fragment thereof) with part or all of a pro domain.

Associated tissue targeting or solubility-enhancing molecules also may be covalently linked to the morphogen using standard chemical means.

In one preferred embodiment, the morphogen comprises part of an infant formula. The infant formula may be milk-based or nonmilk-based, e.g., soy-based. A typical ready-to-feed morphogen-enriched formulation for infants, when diluted to feeding concentrations, comprises, in addition to the morphogen added to the formula, from about 1–5% by weight fat, from about 0.01 to about 0.5% by weight immunoglobulins as appropriate, from about 4–10% by weight carbohydrate in a quantity substantially to mimic the carbohydrate content of human mother's milk, from about 0.5 to 4% by weight protein in a quantity substantially to mimic the protein content of human mother's milk, optional vitamins and minerals as required, a total solids content of from about 8 to 17% by weight, and the remainder water.

In another preferred embodiment, the dietary composition is formulated for individuals at risk for reduced or lost tissue function, such as postmenopausal women, elderly individuals, undernourished or malnourished individuals, dehydrated individuals, drowning victims, individuals suffering from metabolic disorders including an endocrine imbalance, gastrointestinal disorders, or immune-compromised individuals. Undernourished or malnourished individuals include those suffering from a lack of food (starvation) and/or eating disorders (e.g., anorexia nervosa), and/or suffering from a maladsorption syndrome (e.g., individuals afflicted with digestive or intestinal fistulas, shortened bowel, or hypercatabolism.) Individuals receiving a medical therapy, including radiotherapy, chemotherapy or a surgical procedure also are at risk for reduced or lost tissue function as a result of a therapy-related malabsorption-malnutrition dysfunction. In another embodiment, the dietary supplement is formulated for individuals undergoing periods of increased growth or stress, such as infants and juveniles, or pregnant or lactating women. In another embodiment, the dietary supplement is formulated for individuals at risk for reduced or lost organ function as results from tissue cirrhosis or an autoimmune disease.

Morphogen-enriched nutritional products, particularly clinical nutrition products for use in hospital or other clinical settings, in addition to comprising a morphogen preferably are based on the utilization of diverse other protein sources (casein, sodium and calcium caseinate, isolated soy protein, protein hydrolyzates and/or crystalline amino acids) mixtures of vegetable and animal fats, carbohydrates (basically glucose polymers), vitamins and minerals to meet, at least, the dietary intakes recommended for healthy individuals (see, for example, Committee on Dietary Allowances, Food and Nutrition Board, *Nat Acad Sci,* 9th Ed, 1980).

Among the morphogens useful in this invention are proteins originally identified as osteogenic proteins, such as the OP-1, OP-2 and CBMP2 proteins, as well as amino acid sequence-related proteins such as DPP (from Drosophila), Vgl (from Xenopus), Vgr-1 (from mouse, see U.S. Pat. No. 5,011,691 to Oppermann et al.), GDF-1 (from mouse, see Lee (1991) *PNAS* 88: 4250–4254), all of which are presented in Table II and Seq. ID Nos.5–14), and the recently identified 60A protein (from Drosophila, Seq. ID No. 24, see Wharton et al. (1991) *PNAS* 88: 9214–9218.) The members of this family, which include members of the TGF-β superfamily of proteins, share substantial amino acid sequence homology in their C-terminal regions. The proteins are translated as a precursor, having an N-terminal signal peptide sequence, typically less than about 30 residues, followed by a "pro" domain that is cleaved to yield the mature sequence. The "pro" form of the protein includes the pro domain and the mature domain, and forms a soluble species that appears to be the primary form secreted from cultured mammalian cells. The signal peptide is cleaved rapidly upon translation, at a cleavage site that can be predicted in a given sequence using the method of Von Heijne ((1986) *Nucleic Acids Research* 14: 4683–4691.) Table I, below, describes the various morphogens identified to date, including their nomenclature as used herein, their Seq. ID references, and publication sources for the amino acid sequences for the full length proteins not included in the Seq. Listing. The disclosure of these publications is incorporated herein by reference.

TABLE I

| | |
|---|---|
| "OP-1" | Refers generically to the group of morphogenically active proteins expressed from part or all of a DNA sequence encoding OP-1 protein, including allelic and species variants thereof, e.g., human OP-1 ("hOP-1", Seq. ID No. 5, mature protein amino acid sequence), or mouse OP-1 ("mOP-1", Seq. ID No. 6, mature protein amino acid sequence.) The conserved seven cysteine skeleton is defined by residues 38 to 139 of Seq. ID Nos. 5 and 6. The cDNA sequences and the amino acids encoding the full length proteins are provided in Seq. Id Nos. 16 and 17 (hOP1 and Seq. ID Nos. 18 and 19 (mOP1.) The mature proteins are defined by residues 293–431 (hOP1) and 292–430 (mOP1). The "pro" regions of the proteins, cleaved to yield the mature, morphogenically active proteins are defined essentially by residues 30–292 (hOP1) and residues 30–291 (mOP1). |
| "OP-2" | refers generically to the group of active proteins expressed from part or all of a DNA sequence encoding OP-2 protein, including allelic and species variants thereof, e.g., human OP-2 ("hOP-2", Seq. ID No. 7, mature protein amino acid sequence) or mouse OP-2 ("mOP-2", Seq. ID No. 8, mature protein amino acid sequence). The conserved seven cysteine skeleton is defined by residues 38 to 139 of Seq. ID Nos. 7 and 8. The cDNA sequences and the amino acids encoding the full length proteins are provided in Seq. ID Nos. 20 and 21 (hOP2) and Seq. ID Nos. 22 and 23 (mOP2.) The mature proteins are defined essentially by residues 264–402 (hOP2) and 261–399 (mOP2). The "pro" regions of the proteins, cleaved to yield the mature, morphogenically active proteins likely are defined essentially by residues 18–263 (hOP2) and residues 18–260 (mOP2). (Another cleavage site also occurs 21 residues upstream for both OP-2 proteins.) |
| "CBMP2" | refers generically to the morphogenically active proteins expressed from a DNA sequence encoding the CBMP2 proteins, including allelic and species variants thereof, e.g., human CBMP2A ("CBMP2A(fx)", Seq ID No. 9) or human CBMP2B DNA ("CBMP2B(fx)", Seq. ID No. 10). The amino acid sequence for the full length proteins, referred to in the literature as BMP2A and BMP2B, or BMP2 and BMP4, appear in Wozney, et al. (1988) Science242:1528–1534. The pro domain for BMP2 (BMP2A) likely includes residues 25–248 or 25–282; the mature protein, residues 249–396 or 283–396. The pro domain for BMP4 (BMP2B) likely includes residues 25–256 or 25–292; the mature protein, residues 257–408 or 293–408. |
| "DPP(fx)" | refers to protein sequences encoded by the Drosophila DPP gene and defining the conserved seven cysteine skeleton (Seq. ID No. 11). The amino acid sequence for the full length protein appears in Padgett, et al (1987) Nature325: 81–84. The pro domain likely extends from the signal peptide cleavage site to residue 456; the mature protein likely is defined by residues 457–588. |
| "Vgl(fx)" | refers to protein sequences encoded by the Xenopus Vgl gene and defining the conserved seven cysteine skeleton (Seq. ID No. 12). The amino acid sequence for the full length protein appears in |

TABLE I-continued

| | |
|---|---|
| | Weeks (1987) Cell51: 861–867. The prodomain likely extends from the signal peptide cleavage site to residue 246; the mature protein likely is defined by residues 247–360. |
| "Vgr-1(fx)" | refers to protein sequences encoded by the murine Vgr-1 gene and defining the conserved seven cysteine skeleton (Seq. ID No. 13). The amino acid sequence for the full length protein appears in Lyons, et al, (1989) PNAS86: 4554–4558. The prodomain likely extends from the signal peptide cleavage site to residue 299; the mature protein likely is defined by residues 300–438. |
| "GDF-1(fx)" | refers to protein sequences encoded by the human GDF-1 gene and defining the conserved seven cysteine skeleton (Seq. ID No. 14). The cDNA and encoded amino sequence for the full length protein is provided in Seq. ID. No. 32. The prodomain likely extends from the signal peptide cleavage site to residue 214; the mature protein likely is defined by residues 215–372. |
| "60A" | refers generically to the morphogenically active proteins expressed from part or all of a DNA sequence (from the Drosophila 60A gene) encoding the 60A proteins (see Seq. ID No. 24 wherein the cDNA and encoded amino acid sequence for the full length protein is provided). "60A(fx)" refers to the protein sequences defining the conserved seven cysteine skeleton (residues 354 to 455 of Seq. ID No. 24.) The prodomain likely extends from the signal peptide cleavage site to residue 324; the mature protein likely is defined by residues 325–455. |
| "BMP3(fx)" | refers to protein sequences encoded by the human BMP3 gene and defining the conserved. seven cysteine skeleton (Seq. ID No. 26). The amino acid sequence for the full length protein appears in Wozney et al. (1988) Science242: 1528–1534. The pro domain likely extends from the signal peptide cleavage site to residue 290; the mature protein likely is defined by residues 291–472. |
| "BMP5(fx)" | refers to protein sequences encoded by the human BMP5 gene and defining the conserved seven cysteine skeleton (Seq. ID No. 27). The amino acid sequence for the full length protein appears in Celeste, et al. (1991) PNAS87: 9843–9847. The pro domain likely extends from the signal peptide cleavage site to residue 316; the mature protein likely is defined by residues 317–454. |
| "BMP6(fx)" | refers to protein sequences encoded by the human BMP6 gene and defining the conserved seven cysteine skeleton (Seq. ID No. 28). The amino acid sequence for the full length protein appears in Celeste, et al. (1990) PNAS87: 9843–5847. The pro domain likely includes extends from the signal peptide cleavage site to residue 374; the mature sequence likely includes residues 375–513. |

The OP-2 proteins have an additional cysteine residue in this region (e.g., see residue 41 of Seq. ID Nos. 7 and 8), in addition to the conserved cysteine skeleton in common with the other proteins in this family. The GDF-1 protein has a four amino acid insert within the conserved skeleton (residues 44–47 of Seq. ID No. 14) but this insert likely does not interfere with the relationship of the cysteines in the folded structure. In addition, the CBMP2 proteins are missing one amino acid residue within the cysteine skeleton.

The morphogens are inactive when reduced, but are active as oxidized homodimers and when oxidized in combination with other morphogens of this invention. Thus, as defined herein, a morphogen is a dimeric protein comprising a pair of polypeptide chains, wherein each polypeptide chain comprises at least the C-terminal six cysteine skeleton defined by residues 43–139 of Seq. ID No. 5, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- or inter-chain disulfide bonds such that the protein is capable of acting as a morphogen as defined herein. Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. In addition, it is also anticipated that these morphogens are capable of inducing redifferentiation of committed cells under appropriate environmental conditions.

In one preferred aspect, the morphogens of this invention comprise one of two species of generic amino acid sequences: Generic Sequence 1 (Seq. ID No. 1) or Generic Sequence 2 (Seq. ID No. 2); where each Xaa indicates one of the 20 naturally-occurring L-isomer, α-amino acids or a derivative thereof. Generic Sequence 1 comprises the conserved six cysteine skeleton and Generic Sequence 2 comprises the conserved six cysteine skeleton plus the additional cysteine identified in OP-2 (see residue 36, Seq. ID No. 2). In another preferred aspect, these sequences further comprise the following additional sequence at their N-terminus:

| Cys | Xaa | Xaa | Xaa | Xaa | (Seq. ID No. 15) |
|---|---|---|---|---|---|
| 1 | | | | 5 | |

Preferred amino acid sequences within the foregoing generic sequences include: Generic Sequence 3 (Seq. ID No. 3), Generic Sequence 4 (Seq. ID No. 4), Generic Sequence 5 (Seq. ID No. 30) and Generic Sequence 6 (Seq. ID No. 31), listed below. These Generic Sequences accommodate the homologies shared among the various preferred members of this morphogen family identified in Table II, as well as the amino acid sequence variation among them. Specifically, Generic Sequences 3 and 4 are composite amino acid sequences of the following proteins presented in Table II and identified in Seq. ID Nos. 5–14: human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14.) The generic sequences include both the amino acid identity shared by the sequences in Table II, as well as alternative residues for the variable positions within the sequence. Note that these generic sequences allow for an additional cysteine at position 41 or 46 in Generic Sequences 3 or 4, respectively, providing an appropriate cysteine skeleton where inter- or intramolecular disulfide bonds can form, and contain certain critical amino acids which influence the tertiary structure of the proteins.

| Generic Sequence 3 | | | | | | | | |
|---|---|---|---|---|---|---|---|---|
| | Leu 1 | Tyr | Val | Xaa | Phe 5 | | | |
| Xaa | Xaa | Xaa | Gly | Trp 10 | Xaa | Xaa | Trp | Xaa |
| Xaa 15 | Ala | Pro | Xaa | Gly | Xaa 20 | Xaa | Ala | |
| Xaa | Tyr | Cys 25 | Xaa | Gly | Xaa | Cys | Xaa 30 | |
| Xaa | Pro | Xaa | Xaa | Xaa 35 | Xaa | Xaa | | |
| Xaa | Xaa | Xaa 40 | Asn | His | Ala | Xaa | Xaa 45 | |
| Xaa | Xaa | Leu | Xaa | Xaa 50 | Xaa | Xaa | Xaa | |
| Xaa | Xaa 55 | Xaa | Xaa | Xaa | Xaa | Xaa 60 | Cys | |
| Cys | Xaa | Pro | Xaa 65 | Xaa | Xaa | Xaa | Xaa | |
| Xaa 70 | Xaa | Xaa | Leu | Xaa | Xaa 75 | Xaa | | |
| Xaa | Xaa | Xaa | Xaa 80 | Val | Xaa | Leu | Xaa | |
| Xaa 85 | Xaa | Xaa | Xaa | Met | Xaa 90 | Val | Xaa | |
| Xaa | Cys | Gly 95 | Cys | Xaa | | | | | wherein each Xaa is independently selected from a group of one or more specified amino acids defined as follows: "Res." means "residue" and Xaa at res.4=(Ser, Asp or Glu); Xaa at res.6=(Arg, Gln, Ser or Lys); Xaa at res.7=(Asp or Glu); Xaa at res.8=(Leu or Val); Xaa at res.11=(Gln, Leu, Asp, His or Asn); Xaa at res.12=(Asp, Arg or Asn); Xaa at res.14=(Ile or Val); Xaa at res.15=(Ile or Val); Xaa at res.18=(Glu, Gln, Leu, Lys, Pro or Arg); Xaa at res.20=(Tyr or Phe); Xaa at res.21=(Ala, Ser, Asp, Met, His, Leu or Gln); Xaa at res.23=(Tyr, Asn or Phe); Xaa at res.26=(Glu, His, Tyr, Asp or Gln); Xaa at res.28=(Glu, Lys, Asp or Gln); Xaa at res.30=(Ala, Ser, Pro or Gln); Xaa at res.31=(Phe, Leu or Tyr); Xaa at res.33=(Leu or Val); Xaa at res.34=(Asn, Asp, Ala or Thr); Xaa at res.35=(Ser, Asp, Glu, Leu or Ala); Xaa at res.36=(Tyr, Cys, His, Ser or Ile); Xaa at res.37=(Met, Phe, Gly or Leu); Xaa at res.38=(Asn or Ser); Xaa at res.39=(Ala, Ser or Gly); Xaa at res.40=(Thr, Leu or Ser); Xaa at res.44=(Ile or Val); Xaa at res.45=(Val or Leu); Xaa at res.46=(Gln or Arg); Xaa at res.47=(Thr, Ala or Ser); Xaa at res.49=(Val or Met); Xaa at res.50=(His or Asn); Xaa at res.51=(Phe, Leu, Asn, Ser, Ala or Val); Xaa at res.52=(Ile, Met, Asn, Ala or Val); Xaa at res.53=(Asn, Lys, Ala or Glu); Xaa at res.54=(Pro or Ser); Xaa at res.55=(Glu, Asp, Asn, or Gly); Xaa at res.56=(Thr, Ala, Val, Lys, Asp, Tyr, Ser or Ala); Xaa at res.57=(Val, Ala or Ile); Xaa at res.58=(Pro or Asp); Xaa at res.59=(Lys or Leu); Xaa at res.60=(Pro or Ala); Xaa at res.63=(Ala or Val); Xaa at res.65=(Thr or Ala); Xaa at res.66=(Gln, Lys, Arg or Glu); Xaa at res.67=(Leu, Met or Val); Xaa at res.68=(Asn, Ser or Asp); Xaa at res.69=(Ala, Pro or Ser); Xaa at res.70=(Ile, Thr or Val); Xaa at res.71=(Ser or Ala); Xaa at res.72=(Val or Met); Xaa at res.74=(Tyr or Phe); Xaa at res.75=(Phe, Tyr or Leu); Xaa at res.76=(Asp or Asn); Xaa at res.77=(Asp, Glu, Asn or Ser); Xaa at res.78=(Ser, Gln, Asn or Tyr); Xaa at res.79=(Ser, Asn, Asp or Glu); Xaa at res.80=(Asn, Thr or Lys); Xaa at res.82=(Ile or Val); Xaa at res.84=(Lys or Arg); Xaa at res.85=(Lys, Asn, Gln or His); Xaa at res.86=(Tyr or His);

Xaa at res.87=(Arg, Gln or Glu); Xaa at res.88=(Asn, Glu or Asp); Xaa at res.90=(Val, Thr or Ala); Xaa at res.92=(Arg, Lys, Val, Asp or Glu); Xaa at res.93=(Ala, Gly or Glu); and Xaa at res.97=(His or Arg);

| Generic Sequence 4 | | | | | | | | | |
|---|---|---|---|---|---|---|---|---|---|
| Cys 1 | Xaa | Xaa | Xaa | Xaa 5 | Leu | Tyr | Val | Xaa | Phe 10 |
| Xaa | Xaa | Xaa | Gly | Trp 15 | Xaa | Xaa | Trp | Xaa | |
| Xaa 20 | Ala | Pro | Xaa | Gly | Xaa 25 | Xaa | Ala | | |
| Xaa | Tyr | Cys 30 | Xaa | Gly | Xaa | Cys | Xaa 35 | | |
| Xaa | Pro | Xaa | Xaa | Xaa 40 | Xaa | Xaa | | | |
| Xaa | Xaa | Xaa 45 | Asn | His | Ala | Xaa | Xaa 50 | | |
| Xaa | Xaa | Leu | Xaa | Xaa 55 | Xaa | Xaa | Xaa | | |
| Xaa | Xaa 60 | Xaa | Xaa | Xaa | Xaa | Xaa 65 | Cys | | |
| Cys | Xaa | Pro | Xaa 70 | Xaa | Xaa | Xaa | Xaa | | |
| Xaa 75 | Xaa | Xaa | Leu | Xaa | Xaa 80 | Xaa | | | |
| Xaa | Xaa | Xaa | Xaa 85 | Val | Xaa | Leu | Xaa | | |
| Xaa 90 | Xaa | Xaa | Xaa | Met | Xaa 95 | Val | Xaa | | |
| Xaa | Cys | Gly 100 | Cys | Xaa | | | | | | wherein each Xaa is independently selected from a group of one or more specified amino acids as defined by the following: "Res." means "residue" and Xaa at res.2=(Lys or Arg); Xaa at res.3=(Lys or Arg); Xaa at res.4=(His or Arg); Xaa at res.5=(Glu, Ser, His, Gly, Arg or Pro); Xaa at res.9=(Ser, Asp or Glu); Xaa at res.11=(Arg, Gln, Ser or Lys); Xaa at res.12=(Asp or Glu); Xaa at res.13=(Leu or Val); Xaa at res.16=(Gln, Leu, Asp, His or Asn); Xaa at res.17=(Asp, Arg, or Asn); Xaa at res.19=(Ile or Val); Xaa at res.20=(Ile or Val); Xaa at res.23=(Glu, Gln, Leu, Lys, Pro or Arg); Xaa at res.25=(Tyr or Phe); Xaa at res.26=(Ala, Ser, Asp, Met, His, Leu, or Gln); Xaa at res.28=(Tyr, Asn or Phe); Xaa at res.31=(Glu, His, Tyr, Asp or Gln); Xaa at res.33=Glu, Lys, Asp or Gln); Xaa at res.35=(Ala, Ser or Pro); Xaa at res.36=(Phe, Leu or Tyr); Xaa at res.38=(Leu or Val); Xaa at res.39=(Asn, Asp, Ala or Thr); Xaa at res.40=(Ser, Asp, Glu, Leu or Ala); Xaa at res.41=(Tyr, Cys, His, Ser or Ile); Xaa at res.42=(Met, Phe, Gly or Leu); Xaa at res.44=(Ala, Ser or Gly); Xaa at res.45=(Thr, Leu or Ser); Xaa at res.49=(Ile or Val); Xaa at res.50=(Val or Leu); Xaa at res.51=(Gln or Arg); Xaa at res.52=(Thr, Ala or Ser); Xaa at res.54=(Val or Met); Xaa at res.55=(His or Asn); Xaa at res.56=(Phe, Leu, Asn, Ser, Ala or Val); Xaa at res.57=(Ile, Met, Asn, Ala or Val); Xaa at res.58=(Asn, Lys, Ala or Glu); Xaa at res.59=(Pro or Ser); Xaa at res.60=(Glu, Asp, or Gly); Xaa at res.61=(Thr, Ala, Val, Lys, Asp, Tyr, Ser or Ala); Xaa at res.62=(Val, Ala or Ile); Xaa at res.63=(Pro or Asp); Xaa at res.64=(Lys or Leu); Xaa at res.65=(Pro or Ala); Xaa at res.68=(Ala or Val); Xaa at res.70=(Thr or Ala); Xaa at res.71=(Gln, Lys, Arg or Glu); Xaa at res.72=(Leu, Met or Val); Xaa at res.73=(Asn, Ser or Asp); Xaa at res.74=(Ala, Pro or Ser); Xaa at res.75=(Ile, Thr or Val); Xaa at res.76=(Ser or Ala); Xaa at res.77=(Val or Met); Xaa at res.79=(Tyr or Phe); Xaa at res.80=(Phe, Tyr or Leu); Xaa at res.81=(Asp or Asn); Xaa at res.82=(Asp, Glu, Asn or Ser); Xaa at res.83=(Ser, Gln, Asn or Tyr); Xaa at res.84=(Ser, Asn, Asp or Glu); Xaa at res.85=(Asn, Thr or Lys); Xaa at res.87=(Ile or Val); Xaa at res.89=(Lys or Arg); Xaa at res.90=(Lys, Asn, Gln or His); Xaa at res.91=(Tyr or His); Xaa at res.92=(Arg, Gln or Glu); Xaa at res.93=(Asn, Glu or Asp); Xaa at res.95=(Val, Thr or Ala); Xaa at res.97=(Arg, Lys, Val, Asp or Glu); Xaa at res.98=(Ala, Gly or Glu); and Xaa at res.102=(His or Arg).

Similarly, Generic Sequence 5 (Seq. ID No. 30) and Generic Sequence 6 (Seq. ID No. 31) accommodate the homologies shared among all the morphogen protein family members identified in Table II. Specifically, Generic Sequences 5 and 6 are composite amino acid sequences of human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14), human BMP3 (Seq. ID No. 26), human BMP5 (Seq. ID No. 27), human BMP6 (Seq. ID No. 28) and 60(A) (from Drosophila, Seq. ID Nos. 24–25). The generic sequences include both the amino acid identity shared by these sequences in the C-terminal domain, defined by the six and seven cysteine skeletons (Generic Sequences 5 and 6, respectively), as well as alternative residues for the variable positions within the sequence. As for Generic Sequences 3 and 4, Generic Sequences 5 and 6 allow for an additional cysteine at position 41 (Generic Sequence 5) or position 46 (Generic Sequence 6), providing an appropriate cysteine skeleton where inter- or intramolecular disulfide bonds can form, and containing certain critical amino acids which influence the tertiary structure of the proteins.

| Generic Sequence 5 | | | | | | | |
|---|---|---|---|---|---|---|---|
| Leu 1 | Xaa | Xaa | Xaa | Phe 5 | | | |
| Xaa | Xaa | Xaa | Gly | Trp 10 | Xaa | Xaa | Trp | Xaa |
| Xaa 15 | Xaa | Pro | Xaa | Xaa 20 | Xaa | Ala | |
| Xaa | Tyr | Cys 25 | Xaa | Gly | Xaa | Cys | Xaa 30 |
| Xaa | Pro | Xaa | Xaa | Xaa 35 | Xaa | Xaa | |
| Xaa | Xaa | Xaa 40 | Asn | His | Ala | Xaa | Xaa 45 |
| Xaa | Xaa | Xaa | Xaa | Xaa 50 | Xaa | Xaa | Xaa |
| Xaa | Xaa 55 | Xaa | Xaa | Xaa | Xaa | Xaa 60 | Cys |
| Cys | Xaa | Pro | Xaa 65 | Xaa | Xaa | Xaa | Xaa |
| Xaa 70 | Xaa | Xaa | Leu | Xaa | Xaa 75 | Xaa | |
| Xaa | Xaa | Xaa | Xaa 80 | Val | Xaa | Leu | Xaa |
| Xaa 85 | Xaa | Xaa | Xaa | Met | Xaa 90 | Val | Xaa |
| Xaa | Cys | Xaa 95 | Cys | Xaa | | | | wherein each Xaa is independently selected from a group of one or more specified amino acids defined as follows: "Res." means "residue" and Xaa at res.2=(Tyr or Lys); Xaa at res.3=Val or Ile); Xaa at res.4=(Ser, Asp or Glu); Xaa at res.6=(Arg, Gln, Ser, Lys or Ala); Xaa at res.7=(Asp, Glu or Lys); Xaa at res.8=(Leu, Val or Ile); Xaa at res.11=(Gln, Leu, Asp, His, Asn or Ser); Xaa at res.12=(Asp, Arg, Asn or Glu); Xaa at res.14=(Ile or Val); Xaa at res.15=(Ile or Val); Xaa at res.16 (Ala or Ser); Xaa at res.18=(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln or Ser); Xaa at res.28=(Glu, Lys, Asp, Gln or Ala); Xaa at res.30=(Ala, Ser, Pro, Gln or Asn); Xaa at res.31=(Phe, Leu or Tyr); Xaa at res.33=(Leu, Val or Met); Xaa at res.34=(Asn, Asp, Ala, Thr or Pro); Xaa at res.35=(Ser, Asp, Glu, Leu, Ala or Lys); Xaa at res.36=(Tyr, Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40=(Thr, Leu or Ser); Xaa at res.44=(Ile, Val or Thr); Xaa at res.45=(Val, Leu or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val or Leu); Xaa at res.53=(Asn, Lys, Ala, Glu, Gly or Phe); Xaa at res.54=(Pro, Ser or Val); Xaa at res.55=(Glu, Asp, Asn, Gly, Val or Lys); Xaa at res.56=(Thr, Ala, Val, Lys, Asp, Tyr, Ser, Ala, Pro or His); Xaa at res.57=(Val, Ala or Ile); Xaa at res.58=(Pro or Asp); Xaa at res.59=(Lys, Leu or Glu); Xaa at res.60=(Pro or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Met or Ile); Xaa at res.74=(Tyr or Phe); Xaa at res.75=(Phe, Tyr, Leu or His); Xaa at res.76=(Asp, Asn or Leu); Xaa at res.77=(Asp, Glu, Asn or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His or Val); Xaa at res.86=(Tyr or His); Xaa at res.87=(Arg, Gln, Glu or Pro); Xaa at res.88=(Asn, Glu or Asp); Xaa at res.90=(Val, Thr, Ala or Ile); Xaa at res.92=(Arg, Lys, Val, Asp or Glu); Xaa at res.93=(Ala, Gly, Glu or Ser); Xaa at res.95=(Gly or Ala) and Xaa at res.97=(His or Arg).

| Generic Sequence 6 | | | | | | | | | |
|---|---|---|---|---|---|---|---|---|---|
| Cys 1 | Xaa | Xaa | Xaa | Xaa 5 | Leu | Xaa | Xaa | Xaa | Phe 10 |
| Xaa | Xaa | Xaa | Gly | Trp 15 | Xaa | Xaa | Trp | Xaa | |
| Xaa 20 | Xaa | Pro | Xaa | Xaa | Xaa 25 | Xaa | Ala | | |
| Xaa | Tyr | Cys 30 | Xaa | Gly | Xaa | Cys | Xaa 35 | | |
| Xaa | Pro | Xaa | Xaa | Xaa 40 | Xaa | Xaa | | | |
| Xaa | Xaa | Xaa | Asn 45 | His | Ala | Xaa | Xaa 50 | | |
| Xaa | Xaa | Xaa | Xaa | Xaa 55 | Xaa | Xaa | Xaa | | |
| Xaa | Xaa | Xaa | Xaa 60 | Xaa | Xaa | Xaa 65 | Cys | | |
| Cys | Xaa | Pro | Xaa 70 | Xaa | Xaa | Xaa | Xaa | | |
| Xaa 75 | Xaa | Xaa | Leu | Xaa | Xaa 80 | Xaa | | | |
| Xaa | Xaa | Xaa | Xaa 85 | Val | Xaa | Leu | Xaa | | |
| Xaa 90 | Xaa | Xaa | Xaa | Met | Xaa 95 | Val | Xaa | | |
| Xaa | Cys | Xaa 100 | Cys | Xaa | | | | | | wherein each Xaa is independently selected from a group of one or more specified amino acids as defined by the following: "Res." means "residue" and Xaa at res.2=(Lys, Arg, Ala or Gln); Xaa at res.3=(Lys, Arg or Met); Xaa at res.4=(His, Arg or Gln); Xaa at res.5=(Glu, Ser, His, Gly, Arg, Pro, Thr, or Tyr); Xaa at res.7=(Tyr or Lys); Xaa at res.8=(Val or Ile);

Xaa at res.9=(Ser, Asp or Glu); Xaa at res.11=(Arg, Gln, Ser, Lys or Ala); Xaa at res.12=(Asp, Glu, or Lys); Xaa at res.13=(Leu, Val or Ile); Xaa at res.16=(Gln, Leu, Asp, His, Asn or Ser); Xaa at res.17=(Asp, Arg, Asn or Glu); Xaa at res.19=(Ile or Val); Xaa at res.20=(Ile or Val); Xaa at res.21=(Ala or Ser); Xaa at res.23=(Glu, Gln, Leu, Lys, Pro or Arg); Xaa at res.24=(Gly or Ser); Xaa at res.25=(Tyr or Phe); Xaa at res.26=(Ala, Ser, Asp, Met, His, Gln, Leu, or Gly); Xaa at res.28=(Tyr, Asn or Phe); Xaa at res.31=(Glu, His, Tyr, Asp, Gln or Ser); Xaa at res.33=Glu, Lys, Asp, Gln or Ala); Xaa at res.35=(Ala, Ser, Pro, Gln or Asn); Xaa at res.36=(Phe, Leu or Tyr); Xaa at res.38=(Leu, Val or Met); Xaa at res.39=(Asn, Asp, Ala, Thr or Pro); Xaa at res.40= (Ser, Asp, Glu, Leu, Ala or Lys); Xaa at res.41=(Tyr, Cys, His, Ser or Ile); Xaa at res.42=(Met, Phe, Gly or Leu); Xaa at res.43=(Asn, Ser or Lys); Xaa at res.44=(Ala, Ser, Gly or Pro); Xaa at res.45=(Thr, Leu or Ser); Xaa at res.49=(Ile, Val or Thr); Xaa at res.50=(Val, Leu or Ile); Xaa at res.51=(Gln or Arg); Xaa at res.52=(Thr, Ala or Ser); Xaa at res.53=(Leu or Ile); Xaa at res.54=(Val or Met); Xaa at res.55=(His, Asn or Arg); Xaa at res.56=(Phe, Leu, Asn, Ser, Ala or Val); Xaa at res.57=(Ile, Met, Asn, Ala, Val or Leu); Xaa at res.58= (Asn, Lys, Ala, Glu, Gly or Phe); Xaa at res.59=(Pro, Ser or Val); Xaa at res.60=(Glu, Asp, Gly, Val or Lys); Xaa at res.61=(Thr, Ala, Val, Lys, Asp, Tyr, Ser, Ala, Pro or His); Xaa at res.62=(Val, Ala or Ile); Xaa at res.63=(Pro or Asp); Xaa at res.64=(Lys, Leu or Glu); Xaa at res.65=(Pro or Ala); Xaa at res.68=(Ala or Val); Xaa at res.70=(Thr, Ala or Glu); Xaa at res.71=(Gln, Lys, Arg or Glu); Xaa at res.72=(Leu, Met or Val); Xaa at res.73=(Asn, Ser, Asp or Gly); Xaa at res.74=(Ala, Pro or Ser); Xaa at res.75=(Ile, Thr, Val or Leu); Xaa at res.76=(Ser, Ala or Pro); Xaa at res.77=(Val, Met or Ile); Xaa at res.79=(Tyr or Phe); Xaa at res.80=(Phe, Tyr, Leu or His); Xaa at res.81=(Asp, Asn or Leu); Xaa at res.82=(Asp, Glu, Asn or Ser); Xaa at res.83=(Ser, Gln, Asn, Tyr or Asp); Xaa at res.84=(Ser, Asn, Asp, Glu or Lys); Xaa at res.85=(Asn, Thr or Lys); Xaa at res.87=(Ile, Val or Asn); Xaa at res.89=(Lys or Arg); Xaa at res.90=(Lys, Asn, Gln, His or Val); Xaa at res.91=(Tyr or His); Xaa at res.92=(Arg, Gln, Glu or Pro); Xaa at res.93=(Asn, Glu or Asp); Xaa at res.95=(Val, Thr, Ala or Ile); Xaa at res.97=(Arg, Lys, Val, Asp or Glu); Xaa at res.98=(Ala, Gly, Glu or Ser); Xaa at res.100=(Gly or Ala); and Xaa at res.102=(His or Arg).

Particularly useful sequences for use as morphogens in this invention include the C-terminal domains, e.g., the C-terminal 96–102 amino acid residues of Vgl, Vgr-1, DPP, OP-1, OP-2, CBMP-2A, CBMP-2B, GDF-1 (see Table II, below, and Seq. ID Nos. 5–14), as well as proteins comprising the C-terminal domains of 60A, BMP3, BMP5 and BMP6 (see Seq. ID Nos. 24–28), all of which include at least the conserved six or seven cysteine skeleton. In addition, biosynthetic constructs designed from the generic sequences, such as COP-1, 3–5, 7, 16, disclosed in U.S. Pat. No. 5,011,691, also are useful. Other sequences include the inhibins/activin proteins (see, for example, U.S. Pat. Nos. 4,968,590 and 5,011,691). Accordingly, other useful sequences are those sharing at least 70% amino acid sequence homology or "similarity", and preferably 80% homology or similarity with any of the sequences above. These are anticipated to include allelic and species variants and mutants, and biosynthetic muteins, as well as novel members of this morphogenic family of proteins. Particularly envisioned in the family of related proteins are those proteins exhibiting morphogenic activity and wherein the amino acid changes from the preferred sequences include conservative changes, e.g., those as defined by Dayoff et al., *Atlas of Protein Sequence and Structure*; vol. 5, Suppl. 3, pp. 345–362, (M. O. Dayoff, ed., Nat'l BioMed. Research Fdn., Washington, D.C. 1979). As used herein, potentially useful sequences are aligned with a known morphogen sequence using the method of Needleman et al. (((1970) *J.Mol.Biol.* 48: 443–453) and identities calculated by the Align program (DNAstar, Inc.). "Homology" or "similarity" as used herein includes allowed conservative changes as defined by Dayoff et al.

The currently most preferred protein sequences useful as morphogens in this invention include those having greater than 60% identity, preferably greater than 65% identity, with the amino acid sequence defining the conserved six cysteine skeleton of hOP1 (e.g., residues 43–139 of Seq. ID No. 5). These most preferred sequences include both allelic and species variants of the OP-1 and OP-2 proteins, including the Drosophila 60A protein. Accordingly, in another preferred aspect of the invention, useful morphogens include active proteins comprising species of polypeptide chains having the generic amino acid sequence herein referred to as "OPX", which accommodates the homologies between the various identified species of OP1 and OP2 (Seq. ID No. 29).

The morphogens useful in the methods, composition and devices of this invention include proteins comprising any of the polypeptide chains described above, whether isolated from naturally-occurring sources, or produced by recombinant DNA or other synthetic techniques, and includes allelic and species variants of these proteins, naturally-occurring or biosynthetic mutants thereof, as well as various truncated and fusion constructs. Deletion or addition mutants also are envisioned to be active, including those which may alter the conserved C-terminal cysteine skeleton, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The morphogenic proteins can be expressed from intact or truncated cDNA or from synthetic DNAs in procaryotic or eucaryotic host cells, and purified, cleaved, refolded, and dimerized to form morphogenically active compositions. Currently preferred host cells include *E. coli* or mammalian cells, such as CHO, COS or BSC cells. A detailed description of the morphogens useful in the methods, compositions and devices of this invention is disclosed in copending U.S. patent application Ser. No. 752,764, filed Aug. 30, 1991, and Ser. No. 667,274, filed Mar. 11, 1991, the disclosure of which are incorporated herein by reference.

Thus, in view of this disclosure, skilled genetic engineers can isolate genes from cDNA or genomic libraries of various different species which encode appropriate amino acid sequences, or construct DNAs from oligonucleotides, and then can express them in various types of host cells, including both procaryotes and eucaryotes, to produce large quantities of active proteins useful as dietary compositions for enhancing tissue morphogenesis, including enhancing tissue development and tissue viability in a variety of mammals, including humans.

The foregoing and other objects, features and advantages of the present invention will be made more apparent from the following detailed description of the invention.

BRIEF DESCRIPTION OF THE DRAWINGS

The foregoing and other objects and features of this invention, as well as the invention itself, may be more fully understood from the following description, when read together with the accompanying drawings, in which.

DETAILED DESCRIPTION OF THE INVENTION

Figure 1A:
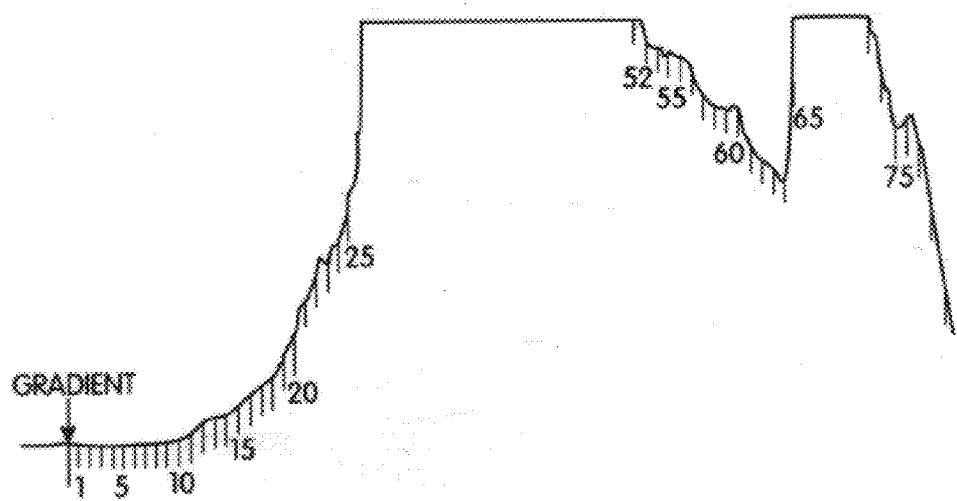
FIG. 1A and B shows relative amounts of protein present in mammary gland extract eluate fractions of a C-18 reverse phase chromatography column (A), and the corresponding results of a Western Blot (B)

It now has been discovered that the proteins described herein are found in nursing mother's milk and are useful as components of a dietary composition for enhancing tissue morphogenesis in a mammal, particularly in an individual at risk for normal tissue development and viability. As described herein, these proteins ("morphogens") are capable of enhancing tissue development in growing mammals, stimulating CAM expression and maintaining the normal tissue function in adult tissue.

Provided below are detailed descriptions of suitable morphogens useful in the compositions and methods of this invention, as well as methods for their administration and application, and numerous, nonlimiting examples which demonstrate the suitability of the morphogens described herein as active components of a dietary composition for a mammal; and 2) provide assays with which to test candidate morphogens for their efficacy. Specifically, examples are provided which (1) demonstrate the presence of endogenous morphogen in milk and human serum (Examples 1 and 2), (2) demonstrate the ability of morphogens to induce CAM expression in a mammal (Example 3), (3) demonstrate the ability of morphogens to enhance tissue development in developing embryos (Example 4) and juveniles (Example 5); (4) demonstrate the ability of morphogens to reduce an osteoporotic condition in a mammal (Example 6); (5) demonstrate the presence of morphogens in developing tissues and adult stomach and gut tissue, demonstrate the ability of parenterally provided morphogen to localize to stomach tissue, and describe protocols for identifying morphogen-synthesizing tissue (Example 7) and (6) describe protocols for obtaining morphogen-specific antibodies and measuring morphogens in solution (Example 8).

I. Useful Morphogens

As defined herein a protein is morphogenic if it is capable of inducing the developmental cascade of cellular and molecular events that culminate in the formation of new, organ-specific tissue and comprises at least the conserved C-terminal six cysteine skeleton or its functional equivalent (see supra). Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. Details of how the morphogens useful in the method of this invention first were identified, as well as a description on how to make, use and test them for morphogenic activity are disclosed in U.S. Ser. No. 667,274 abandoned in favor of U.S. Ser. No. 752,764 (currently pending as U.S. Ser. No. 08/404,113), the disclosures of which A candidate morphogen or morphogen composition can be evaluated for in vivo morphogenic utility generally according to the procedures set forth in U.S. Ser. No. 08/404,113. The proteins and compositions may be injected or surgically implanted in a mammal, following any of a number of procedures well known in the art. For example, surgical implant bioassays may be performed essentially following the procedure of Sampath et al. (1983) *PNAS* 80: 6591–6595.

Histological sectioning and staining is preferred to determine the extent of morphogenesis in vivo, particularly in tissue repair procedures. Excised implants are fixed in Bouins Solution, embedded in paraffin, and cut into 6–8 $\mu$m sections. Staining with toluidine blue or hemotoxylin/eosin demonstrates clearly the ultimate development of the new tissue. Twelve day implants are usually sufficient to determine whether the implants contain newly induced tissue.

Successful implants exhibit a controlled progression through the stages of induced tissue development allowing one to identify and follow the tissue-specific events that occur. For example, in endochondral bone formation the stages include:

(1) leukocytes on day one;

(2) mesenchymal cell migration and proliferation on days two and three;

(3) chondrocyte appearance on days five and six;

(4) cartilage matrix formation on day seven;

(5) cartilage calcification on day eight;

(6) vascular invasion, appearance of osteoblasts, and formation of new bone on days nine and ten;

(7) appearance of osteoblastic and bone remodeling and dissolution of the implanted matrix on days twelve to eighteen; and (8) hematopoietic bone marrow differentiation in the ossicle on day twenty-one.

In addition to histological evaluation, biological markers may be used as a marker for tissue morphogenesis. Useful markers include tissue-specific enzymes whose activity may be assayed (e.g., spectrophotometrically) after homogenization of the implant. These assays may be useful for quantitation and for obtaining an estimate of tissue formation quickly after the implants are removed from the animal. For example, alkaline phosphatase activity may be used as a marker for osteogenesis.

Incorporation of systemically provided morphogens may be followed using tagged morphogens (e.g., radioactively labelled) and determining their localization in new tissue, and/or by monitoring their disappearance from the circulatory system using a standard pulse-chase labeling protocol. The morphogen also may be provided with a tissue-specific molecular tag, whose uptake may be monitored and correlated with the concentration of morphogen provided. As an example, ovary removal in female rats results in reduced bone alkaline phosphatase activity, rendering the rats predisposed to osteoporosis. If the female rats now are provided with a morphogen, e.g., OP-1, a reduction in the systemic concentration of calcium ($CA^{2+}$) is seen, which correlates with the presence of the provided morphogen and can be shown to correspond to increased alkaline phosphatase activity.

The morphogen to be assayed according to the above-described exemplary procedures can be purified from naturally-sourced material, or can be recombinantly produced from procaryotic or eucaryotic host cells, into which genetic material encoding a morphogen, e.g., genetic material bearing one of the nucleic acid sequences disclosed herein, has been introduced. Alternatively, the above-described exemplary procedures can be used to determine whether a novel protein suspected of being a morphogen indeed has morphogenic activity.

Particularly useful proteins include those which comprise the naturally derived sequences disclosed in Table II. Other useful sequences include biosynthetic constructs such as those disclosed in U.S. Pat. No. 5,011,691, the disclosure of which is incorporated herein by reference (e.g., COP-1, COP-3, COP-4, COP-5, COP-7, and COP-16).

Accordingly, the morphogens useful in the methods and compositions of this invention also may be described by morphogenically active proteins having amino acid sequences sharing 70% or, preferably, 80% homology (similarity) with any of the sequences described above, where "homology" is as defined herein above.

The morphogens useful in the method of this invention also can be described by any of the 6 generic sequences described herein (Generic Sequences 1, 2, 3, 4, 5 and 6). Generic sequences 1 and 2 also may include, at their N-terminus, the sequence

| Cys | Xaa | Xaa | Xaa | Xaa | (Seq. ID No. 15) |
|---|---|---|---|---|---|
| 1 | | | | 5 | |

Table II, set forth below, compares the amino acid sequences of the active regions of native proteins that have been id entified as morphogens, including human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–23), CBMP2A (Seq. ID No. 9), CBMP2B (Seq. ID No. 10), BMP3 (Seq. ID No. 26), DPP (from Drosophila, Seq. ID No. 11), Vgl, (from Xenopus, Seq. ID No. 12), Vgr-1 (from mouse, Seq. ID No. 13), GDF-1 (from mouse, Seq. ID Nos. 14, 32 and 33), 60A protein (from Drosophila, Seq. ID Nos. 24 and 25), BMP5 (Seq. ID No. 27) and BMP6 (Seq. ID No. 28). The sequences are aligned essentially following the method of Needleman et al. (1970) *J. Mol. Biol.,* 48: 443–453, calculated using the Align Program (DNAstar, Inc.) In the table, three dots indicates that the amino acid in that position is the same as the amino acid in hOP-1. Three dashes indicates that no amino acid is present in that position, and are included for purposes of illustrating homologies. For example, amino acid residue 60 of CBMP-2A and CBMP-2B is "missing". Of course, both these amino acid sequences in this region comprise Asn-Ser (residues 58, 59), with CBMP-2A then comprising Lys and Ile, whereas CBMP-2B comprises Ser and Ile.

TABLE II

| | | | | | | | | |
|---|---|---|---|---|---|---|---|---|
| hOP-1 | Cys | Lys | Lys | His | Glu | Leu | Tyr | Val |
| mOP-1 | ... | ... | ... | ... | ... | ... | ... | ... |
| hOP-2 | ... | Arg | Arg | ... | ... | ... | ... | ... |
| mOP-2 | ... | Arg | Arg | ... | ... | ... | ... | ... |
| DPP | ... | Arg | Arg | ... | Ser | ... | ... | ... |
| Vgl | ... | ... | Lys | Arg | His | ... | ... | ... |
| Vgr-1 | ... | ... | ... | ... | Gly | ... | ... | ... |
| CBMP-2A | ... | ... | Arg | ... | Pro | ... | ... | ... |
| CBMP-2B | ... | Arg | Arg | ... | Ser | ... | ... | ... |
| BHP3 | ... | Ala | Arg | Arg | Tyr | ... | Lys | ... |
| GDF-1 | ... | Arg | Ala | Arg | Arg | ... | ... | ... |
| 60A | ... | Gln | Met | Glu | Thr | ... | ... | ... |
| BHP5 | ... | ... | ... | ... | ... | ... | ... | ... |
| BMP6 | ... | Arg | ... | ... | ... | ... | ... | ... |
| | 1 | | | | 5 | | | |
| hOP-1 | Ser | Phe | Arg | Asp | Leu | Gly | Trp | Gln | Asp |
| mOP-1 | ... | ... | ... | ... | ... | ... | ... | ... | ... |
| hOP-2 | ... | ... | Gln | ... | ... | ... | ... | Leu | ... |
| mOP-2 | Ser | ... | ... | ... | ... | ... | ... | Leu | ... |
| DPP | Asp | ... | Ser | ... | Val | ... | ... | Asp | ... |
| Vgl | Glu | ... | Lys | ... | Val | ... | ... | ... | Asn |
| Vgr-1 | ... | ... | Gln | ... | Val | ... | ... | ... | ... |
| CBMP-2A | Asp | ... | Ser | ... | Val | ... | ... | Asn | ... |
| CBMP-2B | Asp | ... | Ser | ... | Val | ... | ... | Asn | ... |
| BHP3 | Asp | ... | Ala | ... | Ile | ... | ... | Ser | Glu |
| GDF-1 | ... | ... | ... | Glu | Val | ... | ... | His | Arg |
| 60A | Asp | ... | Lys | ... | ... | ... | ... | His | ... |
| BHP5 | ... | ... | ... | ... | ... | ... | ... | ... | ... |
| BHP6 | ... | ... | Gln | ... | ... | ... | ... | ... | ... |

TABLE II-continued

| | | 10 | | | | | 15 | | |
|---|---|---|---|---|---|---|---|---|---|
| hOP-1 | Trp | Ile | Ile | Ala | Pro | Glu | Gly | Tyr | Ala |
| mOP-1 | ... | ... | ... | ... | ... | ... | ... | ... | ... |
| hOP-2 | ... | Val | ... | ... | ... | Gln | ... | ... | Ser |
| mOP-2 | ... | Val | ... | ... | ... | Gln | ... | ... | Ser |
| DPP | ... | ... | Val | ... | ... | Leu | ... | ... | Asp |
| Vgl | ... | Val | ... | ... | ... | Gln | ... | ... | Met |
| Vgr-1 | ... | ... | ... | ... | ... | Lys | ... | ... | ... |
| CBMP-2A | ... | ... | Val | ... | ... | Pro | ... | ... | His |
| CBMP-2B | ... | ... | Val | ... | ... | Pro | ... | ... | Gln |
| BHP3 | ... | ... | ... | Ser | ... | Lys | Ser | Phe | Asp |
| GDF-1 | ... | Val | ... | ... | ... | Arg | ... | Phe | Leu |
| 60A | ... | ... | ... | ... | ... | ... | ... | ... | Gly |
| BHP5 | ... | ... | ... | ... | ... | ... | ... | ... | ... |
| BHP6 | ... | ... | ... | ... | ... | Lys | ... | ... | ... |

| | | | | 20 | | | | 25 | |
|---|---|---|---|---|---|---|---|---|---|
| hOP-1 | Ala | Tyr | Tyr | Cys | Glu | Gly | Glu | Cys | Ala |
| mOP-1 | ... | ... | ... | ... | ... | ... | ... | ... | ... |
| hOP-2 | ... | ... | ... | ... | ... | ... | ... | ... | Ser |
| mOP-2 | ... | ... | ... | ... | ... | ... | ... | ... | ... |
| DPP | ... | ... | ... | ... | His | ... | Lys | ... | Pro |
| Vgl | ... | Asn | ... | ... | Tyr | ... | ... | ... | Pro |
| Vgr-1 | ... | Asn | ... | ... | Asp | ... | ... | ... | Ser |
| CBMP-2A | ... | Phe | ... | ... | His | ... | Glu | ... | Pro |
| CBMP-2B | ... | Phe | ... | ... | His | ... | Asp | ... | Pro |
| BMP3 | ... | ... | ... | ... | Ser | ... | Ala | ... | Gln |
| GDF-1 | ... | Asn | ... | ... | Gln | ... | Gln | ... | ... |
| 60A | ... | Phe | ... | ... | Ser | ... | ... | ... | Asn |
| BMP5 | ... | Phe | ... | ... | Asp | ... | ... | ... | Ser |
| BMP6 | ... | Asn | ... | ... | Asp | ... | ... | ... | Ser |

| | | | | | 30 | | | | 35 |
|---|---|---|---|---|---|---|---|---|---|
| hOP-1 | Phe | Pro | Leu | Asn | Ser | Tyr | Met | Asn | Ala |
| mOP-1 | ... | ... | ... | ... | ... | ... | ... | ... | ... |
| hOP-2 | ... | ... | ... | Asp | ... | Cys | ... | ... | ... |
| mOP-2 | ... | ... | ... | Asp | ... | Cys | ... | ... | ... |
| DPP | ... | ... | ... | Ala | Asp | His | Phe | ... | Ser |
| Vgl | Tyr | ... | ... | Thr | Glu | Ile | Leu | ... | Gly |
| Vgr-1 | ... | ... | ... | ... | Ala | His | ... | ... | ... |
| CBMP-2A | ... | ... | ... | Ala | Asp | His | Leu | ... | Ser |
| CBMP-2B | ... | ... | ... | Ala | Asp | His | Leu | ... | Ser |
| GDF-1 | Leu | ... | Val | Ala | Leu | Ser | Gly | Ser** | ... |
| BMP3 | ... | ... | Met | Pro | Lys | Ser | Leu | Lys | Pro |
| 60A | ... | ... | ... | ... | Ala | His | ... | ... | ... |
| BMP5 | ... | ... | ... | ... | Ala | His | Met | ... | ... |
| BMP6 | ... | ... | ... | ... | Ala | His | Met | ... | ... |

| | | | | | | 40 | | | |
|---|---|---|---|---|---|---|---|---|---|
| hOP-1 | Thr | Asn | His | Ala | Ile | Val | Gln | Thr | Leu |
| mOP-1 | ... | ... | ... | ... | ... | ... | ... | ... | ... |
| hOP-2 | ... | ... | ... | ... | ... | Leu | ... | Ser | ... |
| mOP-2 | ... | ... | ... | ... | ... | Leu | ... | Ser | ... |
| DPP | ... | ... | ... | ... | Val | ... | ... | ... | ... |
| Vgl | Ser | ... | ... | ... | ... | Leu | ... | ... | ... |
| Vgr-1 | ... | ... | ... | ... | ... | ... | ... | ... | ... |
| CBMP-2A | ... | ... | ... | ... | ... | ... | ... | ... | ... |
| CBMP-2B | ... | ... | ... | ... | ... | ... | ... | ... | ... |
| BHP3 | Ser | ... | ... | ... | Thr | Ile | ... | Ser | Ile |
| GDF-1 | Leu | ... | ... | ... | Val | Leu | Arg | Ala | ... |
| 60A | ... | ... | ... | ... | ... | ... | ... | ... | ... |
| BHP5 | ... | ... | ... | ... | ... | ... | ... | ... | ... |
| BHP6 | ... | ... | ... | ... | ... | ... | ... | ... | ... |

| | 45 | | | | | 50 | | | |
|---|---|---|---|---|---|---|---|---|---|
| hOP-1 | Val | His | Phe | Ile | Asn | Pro | Glu | Thr | Val |
| mOP-1 | ... | ... | ... | ... | ... | ... | Asp | ... | ... |
| hOP-2 | ... | His | Leu | Met | Lys | ... | Asn | Ala | ... |
| mOP-2 | ... | His | Leu | Met | Lys | ... | Asp | Val | ... |
| DPP | ... | Asn | Asn | Asn | ... | ... | Gly | Lys | ... |
| Vgl | ... | ... | Ser | ... | Glu | ... | ... | Asp | Ile |
| Vgr-1 | ... | ... | Val | Met | ... | ... | ... | Tyr | ... |
| CBMP-2A | ... | Asn | Ser | Val | ... | Ser | — | Lys | Ile |
| CBMP-2B | ... | Asn | Ser | Val | ... | Ser | — | Ser | Ile |
| BHP3 | ... | Arg | Ala** | Gly | Val | Val | Pro | Gly | Ile |
| GDF-1 | Met | ... | Ala | Ala | Ala | ... | Gly | Ala | Ala |
| 60A | ... | ... | Leu | Leu | Glu | ... | Lys | Lys | ... |
| BHP5 | ... | ... | Leu | Met | Phe | ... | Asp | His | ... |
| BHP6 | ... | ... | Leu | Met | ... | ... | ... | Tyr | ... |

| | | 55 | | | | | 60 | | |
|---|---|---|---|---|---|---|---|---|---|
| hOP-1 | Pro | Lys | Pro | Cys | Cys | Ala | Pro | Thr | Gln |
| mOP-1 | ... | ... | ... | ... | ... | ... | ... | ... | ... |
| hOP-2 | ... | ... | Ala | ... | ... | ... | ... | ... | Lys |

TABLE II-continued

|  | | | | | | | | | 70 |
|---|---|---|---|---|---|---|---|---|---|
| mOP-2 | ... | ... | Ala | ... | ... | ... | ... | ... | Lys |
| DPP | ... | ... | Ala | ... | ... | Val | ... | ... | ... |
| Vgl | ... | Leu | ... | ... | ... | Val | ... | ... | Lys |
| Vgr-1 | ... | ... | ... | ... | ... | ... | ... | ... | Lys |
| CBMP-2A | ... | ... | Ala | ... | ... | Val | ... | ... | Glu |
| CBMP-2B | ... | ... | Ala | ... | ... | Val | ... | ... | Glu |
| BMP3 | ... | Glu | ... | ... | ... | Val | ... | Glu | Lys |
| GDF-1 | Asp | Leu | ... | ... | ... | Val | ... | Ala | Arg |
| 60A | ... | ... | ... | ... | ... | ... | ... | ... | Arg |
| BHP5 | ... | ... | ... | ... | ... | ... | ... | ... | Lys |
| BMP6 | ... | ... | ... | ... | ... | ... | ... | ... | Lys |

|  | | | 65 | | | | | 70 | |
|---|---|---|---|---|---|---|---|---|---|
| hOP-1 | Leu | Asn | Ala | Ile | Ser | Val | Leu | Tyr | Phe |
| mOP-1 | ... | ... | ... | ... | ... | ... | ... | ... | ... |
| hOP-2 | ... | Ser | ... | Thr | ... | ... | ... | ... | Tyr |
| mOP-2 | ... | Ser | ... | Thr | ... | ... | ... | ... | Tyr |
| Vgl | Met | Ser | Pro | ... | ... | Met | ... | Phe | Tyr |
| Vgr-1 | Val | ... | ... | ... | ... | ... | ... | ... | ... |
| DPP | ... | Asp | Ser | Val | Ala | Met | ... | ... | Leu |
| CBMP-2A | ... | Ser | ... | ... | ... | Met | ... | ... | Leu |
| CBMP-2B | ... | Ser | ... | ... | ... | Met | ... | ... | Leu |
| BMP3 | Met | Ser | Ser | Leu | ... | Ile | ... | Phe | Tyr |
| GDF-1 | ... | Ser | Pro | ... | ... | ... | ... | Phe | ... |
| 60A | ... | Gly | ... | Leu | Pro | ... | ... | ... | His |
| BMP5 | ... | ... | ... | ... | ... | ... | ... | ... | ... |
| BMP6 | ... | ... | ... | ... | ... | ... | ... | ... | ... |

|  | | | | 75 | | | | | 80 |
|---|---|---|---|---|---|---|---|---|---|
| hOP-1 | Asp | Asp | Ser | Ser | Asn | Val | Ile | Leu | Lys |
| mOP-1 | ... | ... | ... | ... | ... | ... | ... | ... | ... |
| hOP-2 | ... | Ser | ... | Asn | ... | ... | ... | ... | Arg |
| mOP-2 | ... | Ser | ... | Asn | ... | ... | ... | ... | Arg |
| DPP | Asn | ... | Gln | ... | Thr | ... | Val | ... | ... |
| Vgl | ... | Asn | Asn | Asp | ... | ... | Val | ... | Arg |
| Vgr-1 | ... | ... | Asn | ... | ... | ... | ... | ... | ... |
| CBMP-2A | ... | Glu | Asn | Glu | Lys | ... | Val | ... | ... |
| CBMP-2B | ... | Glu | Tyr | Asp | Lys | ... | Val | ... | ... |
| BHP3 | ... | Glu | Asn | Lys | ... | ... | Val | ... | ... |
| GDF-1 | ... | Asn | ... | Asp | ... | ... | Val | ... | Arg |
| 60A | Leu | Asn | Asp | Glu | ... | ... | Asn | ... | ... |
| BMP5 | ... | ... | ... | ... | ... | ... | ... | ... | ... |
| BHP6 | ... | ... | Asn | ... | ... | ... | ... | ... | ... |

|  | | | | | 85 | | | |
|---|---|---|---|---|---|---|---|---|
| hOP-1 | Lys | Tyr | Arg | Asn | Met | Val | Val | Arg |
| mOP-1 | ... | ... | ... | ... | ... | ... | ... | ... |
| hOP-2 | ... | His | ... | ... | ... | ... | ... | Lys |
| mOP-2 | ... | His | ... | ... | ... | ... | ... | Lys |
| DPP | Asn | ... | Gln | Glu | ... | Thr | ... | Val |
| Vgl | His | ... | Glu | ... | ... | Ala | ... | Asp |
| Vgr-1 | ... | ... | ... | ... | ... | ... | ... | ... |
| CBMP-2A | Asn | ... | Gln | Asp | ... | ... | ... | Glu |
| CBMP-2B | Asn | ... | Gln | Glu | ... | ... | ... | Glu |
| BHP3 | Val | ... | Pro | ... | ... | Thr | ... | Glu |
| GDF-1 | Gln | ... | Glu | Asp | ... | ... | ... | Asp |
| 60A | ... | ... | ... | ... | ... | Ile | ... | Lys |
| BHP5 | ... | ... | ... | ... | ... | ... | ... | ... |
| BMP6 | ... | ... | ... | Trp | ... | ... | ... | ... |

| 90 | | | | | 95 |
|---|---|---|---|---|---|
| hOP-1 | Ala | Cys | Gly | Cys | His |
| mOP-1 | ... | ... | ... | ... | ... |
| hOP-2 | ... | ... | ... | ... | ... |
| mOP-2 | ... | ... | ... | ... | ... |
| DPP | Gly | ... | ... | ... | Arg |
| Vgl | Glu | ... | ... | ... | Arg |
| Vgr-1 | ... | ... | ... | ... | ... |
| CBMP-2A | Gly | ... | ... | ... | Arg |
| CBMP-2B | Gly | ... | ... | ... | Arg |
| BHP3 | Ser | ... | Ala | ... | Arg |
| GDF-1 | Glu | ... | ... | ... | Arg |
| 60A | Ser | ... | ... | ... | ... |
| BMP5 | Ser | ... | ... | ... | ... |
| BMP6 | ... | ... | ... | ... | ... |
| 100 | | | | | |

**Between residues 56 and 57 of BMP3 is a Val residue; between residues 43 and 44 of GDF-1 lies the amino acid sequence Gly-Gly-Pro-Pro.

As is apparent from the foregoing amino acid sequence comparisons, significant amino acid changes can be made within the generic sequences while retaining the morphogenic activity. For example, while the GDF-1 protein sequence depicted in Table II shares only about 50% amino acid identity with the hOP1 sequence described therein, the GDF-1 sequence shares greater than 70% amino acid sequence homology (or "similarity") with the hOP1 sequence, where "homology" or "similarity" includes allowed conservative amino acid changes within the sequence as defined by Dayoff, et al., *Atlas of Protein Sequence and Structure* vol.5, supp.3, pp.345–362, (M. O. Dayoff, ed., Nat'l BioMed. Res. Fd'n, Washington D.C. 1979.)

The currently most preferred protein sequences useful as morphogens in this invention include those having greater than 60% identity, preferably greater than 65% identity, with the amino acid sequence defining the conserved six cysteine skeleton of hOP1 (e.g., residues 43–139 of Seq. ID No. 5). These most preferred sequences include both allelic and species variants of the OP-1 and OP-2 proteins, including the Drosophila 60A protein. Accordingly, in still another preferred aspect, the invention includes morphogens comprising species of polypeptide chains having the generic amino acid sequence referred to herein as "OPX", which defines the seven cysteine skeleton and accommodates the identities between the various identified mouse and human OP1 and OP2 proteins. OPX is presented in Seq. ID No. 29. As described therein, each Xaa at a given position independently is selected from the residues occurring at the corresponding position in the C-terminal sequence of mouse or human OP1 or OP2 (see Seq. ID Nos. 5–8 and/or Seq. ID Nos. 16–23).

II. Formulations and Methods for Administering Therapeutic Agents

A. General Considerations

The morphogens may be provided to an individual by any suitable means, most preferably orally, or, alternatively, parenterally. Where the morphogen is to be provided parenterally, such as intravenously or by enteral feeding tube, the morphogen preferably comprises part of an aqueous solution. The solution is physiologically acceptable so that in addition to delivery of the desired morphogen to the patient, the solution does not otherwise adversely affect the patient's electrolyte and volume balance. The aqueous medium for the morphogen thus may comprise normal physiologic saline (0.85% NaCl, 0.15 M), pH 7–7.4. The aqueous solution containing the morphogen can be made, for example, by dissolving the protein in 50% ethanol containing acetonitrile in 0.1% trifluoroacetic acid (TFA) or 0.1% HCl, or equivalent solvents. One volume of the resultant solution then is added, for example, to ten volumes of phosphate buffered saline (PBS), which further may include 0.1–0.2% human serum albumin (HSA). The resultant solution preferably is vortexed extensively. If desired, a given morphogen may be made more soluble by association with a suitable molecule. For example, the pro form of the morphogenic protein comprises a species that is soluble in physiologically buffered solutions. In fact, the endogenous protein is thought to be transported (e.g., secreted and circulated) in this form. This soluble form of the protein may be obtained from the culture medium of morphogen-secreting mammalian cells. Alternatively, a soluble species may be formulated by complexing the mature dimer (or an active fragment thereof) with part or all of a pro domain. Another molecule capable of enhancing solubility and particularly useful for oral administrations, is casein, including salts, derivatives and analogs thereof. For example, addition of 0.2% casein increases solubility of the mature active form of OP-1 in physiologically buffered solutions by 80%. Other components found in milk and/or various serum proteins also may be useful.

Useful solutions for parenteral administration may be prepared by any of the methods well known in the pharmaceutical art, described, for example, in *Remington's Pharmaceutical Sciences* (Gennaro, A., ed.), Mack Pub., 1990. Formulations may include, for example, polyalkylene glycols such as polyethylene glycol, oils of vegetable origin, hydrogenated naphthalenes, and the like. Biocompatible, preferably bioresorbable, polymers, including, for example, hyaluronic acid, collagen, polybutyrate, tricalcium phosphate, lactide and lactide/glycolide copolymers, may be useful excipients to control the release of the morphogen in vivo.

As described above, the dietary supplements comprising the morphogens described herein preferably are provided orally. Oral administration of proteins as therapeutics generally is not practiced as most proteins are readily degraded by digestive enzymes and acids in the mammalian digestive system before they can be absorbed into the bloodstream. However, the morphogens described herein typically are acid stable and protease-resistant (see, for example, U.S. Pat. No. 4,968,590.) In addition, at least one morphogen, OP-1, has been identified in mammary gland extract, colostrum and 57-day milk (see Example 1, below). Moreover, the OP-1 purified from mammary gland extract is morphogenically active. Specifically, this protein induces endochondral bone formation in mammals when implanted subcutaneously in association with a suitable matrix material, using a standard in vivo bone assay, such as is disclosed in U.S. Pat. No. 4,968,590. Moreover, the morphogen also is detected in the bloodstream (see Example 2, below). These findings indicate that oral and parenteral administration are viable means for administering morphogens to an individual. In addition, while the mature forms of certain morphogens described herein typically are sparingly soluble, the morphogen form found in milk (and mammary gland extract and colostrum) is readily soluble, probably by association of the mature, morphogenically active form with part or all of the pro domain of the intact sequence and/or by association with one or more milk components. Accordingly, the compounds provided herein also may be associated with molecules capable of enhancing their solubility in vitro or in vivo.

The dietary compositions for oral administration may be formulated as a liquid, for example, as part of an aqueous medium as described above for parenteral administration, and which further may contain flavoring and coloring agents. The formulation also may be combined with a beverage or may be provided in a syrup. The dietary composition also may be provided as an aerosol for oral or nasal administration. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Alternatively, the dietary composition may be provided as a solid, for example as a tablet, capsule or lozenge. As for parenteral administration, formulations for oral administration also may include molecules to enhance a controlled release of the morphogen in vivo.

As will be appreciated by those skilled in the art, the concentration of the compounds described in a given dietary supplement composition will vary depending upon a number of factors, including the dosage number to be administered, the chemical characteristics (e.g., hydrophobicity) of the compounds employed, and the route of administration. The preferred dosage to be administered also is likely to depend on such variables as the type and extent of tissue development enhancement desired, the type and extent of any tissue damage present to be repaired, the overall health status of the particular individual, the relative biological efficacy of the compound selected, the formulation of the compound excipients, and its route of administration. In general terms, the compounds of this invention may be provided in a formulation containing about 0.001 to 10% w/v of morphogen to formulation. Typical dose ranges are from about 10 ng/kg to about 1 g/kg of body weight per day; a preferred dose range is from about 0.1 μg/kg to 100 mg/kg of body weight per day. Optimally, the morphogen dosage given is between 0.1–100 μg of protein per kilogram weight of the individual. No obvious morphogen induced pathological lesions are induced when mature morphogen (e.g., OP-1, 20 μg) is administered daily to normal growing rats for 21 consecutive days. Moreover, 10 μg systemic injections of morphogen (e.g., OP-1) injected daily for 10 days into normal newborn mice does not produce any gross abnormalities.

In administering morphogens parenterally in the methods of the present invention, preferably a large volume loading dose is used at the start of the treatment. The treatment then is continued with a maintenance dose. In all cases administration dosages then can be monitored by measuring at intervals the levels of the morphogen in the blood.

B. Considerations for Infant and Other Formulas

1. Infant Formulas

In all cases the morphogens of this invention preferably are added to an infant formula that complies with the nutritional guidelines provided by the AAP and ESPGAN. Basic ingredients for infant formulas include cow's milk, protein, whey proteins, casein and its salts (i.e. calcium caseinate). Soy protein isolates may be substituted for milk-derived proteins, and preferably are used in the products made for infants with lactose intolerance and/or cow's protein intolerance. Protein hydrolyzates (i.e. casein and lactalbumin hydrolyzates) with low molecular weight, also may be used for these products.

The proportions of the diverse component nutrients preferably are similar to those of human milk. Thus, the ratio of whey proteins to casein preferably varies from 60:40 to 70:30 in infant formulas based on milk. The mixture of fats employed is made up of edible fats to provide an essential fatty acid profile. Lactose preferably is used as the carbohydrate source for at-term newborns infants, and dextrin-maltose preferably is employed in products used for the treatment of lactose intolerance and malabsorption syndromes in infancy.

Infant formulas according to the invention also preferably contain minerals (including calcium, phosphorus, sodium, potassium, chloride, magnesium, iron, zinc, copper, manganese and iodine) and vitamins (including vitamin A, vitamin D3, vitamin C, vitamin B1, vitamin B2, vitamin B6, vitamin B12, pantothenic acid, vitamin E, vitamin K1, folic acid, biotin) adequate for the infants' requirements. Also, in the products whose source of proteins is derived from soy or protein isolates or hydrolyzates, carnitine preferably is included to satisfy the nutritional requirements for this compound in infants with malabsorptive syndromes.

A typical ready-to-feed morphogen-enriched formulation for infants, when diluted to feeding concentrations, preferably comprises in addition to the added morphogen, from about 1–5% by weight fat, from about 0.01 to about 0.5% by weight immunoglobulins as appropriate, from about 4–10% by weight carbohydrate in a quantity substantially to mimic the carbohydrate content of human mother's milk, from about 0.5 to 4% by weight protein in a quantity substantially to mimic the protein content of human mother's milk, optional vitamins and minerals as required, a total solids content of from about 8 to 17% by weight, and the remainder water.

A typical protein source for use in infant formula is electrodialyzed whey or electrodialyzed skim milk or milk whey, although other protein sources are also available and may be used. Preferred sugars include food grade substances such as glucose, dextrose, sucrose, or edible lactose. The following vitamins and minerals may also be incorporated in the infant formula: calcium, phosphorus, potassium, sodium, chloride, magnesium, manganese, iron, copper, zinc, selenium, iodine, and vitamins A, E, D, and B complex. These micronutrients are added in the form of commonly accepted nutritional compounds in amounts equivalent to those present in human milk on a per calories basis.

The infant formula according to the present invention also preferably is sterilized and subsequently used on a ready-to-feed basis, or can be stored as a concentrate. The concentrate can be prepared using standard procedures known in the art, and the formula can be reconstituted by rehydrating the concentrate. The infant formula preferably is a stable liquid and has a suitable shelf life. A more detailed description of infant formula considerations, including preferred formulations for newborn, preterm and low birth-weight infants, lactose-intolerant infants, may be found, for example, in U.S. Pat. No. 5,066,500 to Gil et al., the disclosure of which is incorporated herein by reference.

2. Other Nutritional Products

The morphogen-enriched dietary products for balanced nutrition (e.g., dietary food formulations) according to the present invention, preferably have, in addition to added morphogen, a composition of nutrients adequate to the specific requirements of not only healthy human in need of a balanced nutritional product, but also those individuals at risk for lost or reduced tissue function due malnutrition-maladsorption disorder, and/or altered metabolism. Individuals particularly affected by an altered metabolic function include postmenopausal women or aged individuals, hypercatabolic individuals, and individuals undergoing periods of rapid growth or physical stress, such as developing juveniles, and pregnant, lactating and nursing mothers. Other individuals at risk are those suffering from malnutrition, induced, for example, by starvation and/or an eating disorder, and individuals affected with energy-protein malnutrition and in hypercatablic states derived from traumatic, septic, surgical processes and other clinically-derived malabsorption syndromes.

Morphogen-enriched nutritional products according to the present invention preferably also provide mineral elements which include trace elements and vitamins in adequate proportions to satisfy the specific requirements of normal healthy individuals as well as individuals at risk, such as those suffering malabsorption-malnutrition processes and in a hypercatabolic state. The nutritional products also preferably are enriched with amino acids sources, vitamins, nucleosides and/or nucleotides in similar amounts to those present in ordinary foods.

As described above for infant formulas, liquid products may be formulated ready for consumption or as concentrates to be diluted before use. Preferably, liquid dietary compositions have pH values generally ranging from about 6.0 to about 8.0, most preferably 6.8–7.5.

Useful dietary compositions and considerations for their formulation are well described in the medical and nutritional arts. Useful compositions for clinical nutrition, also are described in detail in U.S. Pat. No. 5,066,500.

III. Examples

Example 1

Determination of the Presence of Morphogen in Milk

Morphogenically active OP-1 was demonstrated to be present in mammary gland extract, colostrum, and milk, as described below. The discovery that the morphogen naturally is present in milk, together with the known observation that mature, active OP-1 is acid-stable and protease-resistant, indicate that oral administration is a useful route for therapeutic administration of morphogen to a mammal. Oral administration typically is the preferred mode of delivery for extended or prophylactic therapies. In addition, the identification of morphogen in all milk forms, including colostrum, indicates that the protein plays a significant role in tissue development, including skeletal development of juveniles.

Rat mammary gland extract and bovine colostrum and 57 day milk were subjected to purification procedures designed to partially purify OP-1. The partially purified product then was examined for the presence of OP-1 by Western blot analysis using OP-1-specific antisera, and tested for in vivo and in vitro activity.

1.1 Purification

The purification protocol for all three "milk" forms (e.g., mammary gland extract, colostrum and 57-day milk), involved three chromatography steps: (1) cation-exchange chromatography (S-Sepharose and followed by Phenyl-Sepharose chromatography); (2) Copper-Immobilized Metal Affinity chromatography (Cu++-IMAC); and finally, (3) C-18 reverse phase chromatography. Fractions were sampled at each step for the presence of OP-1. Fraction samples for testing were dialyzed versus water/0.1% TFA, then against 30% acetonitrile/0.1% TFA for analysis on SDS-polyacrylamide gels and immunoblots, using standard methodologies well described in the art. Unless otherwise stated, the primary antibody used for the immunoblots was made against full length OP-1 produced in *E.coli* using standard recombinant DNA and antibody production techniques (see, for example, Example 8, below for a general description for producing morphogen-specific antibodies.) Fractions found to contain the morphogen then were applied to the next column step or used in the immunoreactivity or activity assays described below.

Essentially the same protocol was followed for all three milk sources, except that two alternative cation-exchange methodologies were employed for colostrum purification, described in detail below. Unless otherwise indicated, all chemicals referenced are standard, commercially available reagents, readily available from a number of sources, including Sigma Chemical, Co., St. Louis; Calbiochem, Corp., San Diego and Aldrich Chemical Co., Milwaukee.

step 1. Cation-Exchange Chromatography

The S-Sepharose purification step was performed as follows. 200 ml of cation exchanger (S-Sepharose, Sigma Chemical Corp.) were equilibrated with equilibration buffer (6M urea, 20 mM MES, 70 mM NaCl, pH 6.5). The supernatant from the centrifuged extract was diluted to final concentration of 6M urea, 20 mM MES, 70 mM NaCl, pH 6.5. After loading, the column was washed to baseline using equilibration buffer, and the bound components were eluted stepwise from the column with 6M urea, 20 mM MES, 100 mM and 500 mM NaCl, pH 6.5. The more tightly bound components then were eluted with 4M guanidine, 20 mM sodium phosphate, pH 7.0.

The Phenyl-Sepharose purification step was performed as follows. 15 ml of Phenyl-Sepharose CL-4B (Sigma) were equilibrated with 6M urea, 20 mM HEPES, 1M ammonium sulfate, 300 mM NaCl, pH 7.0. The 500 mM NaCl eluate from the S-Sepharose step was diluted with 6M urea, 20 mM HEPES, 3M ammonium sulfate, 300 mM NaCl, pH 7.0, to a final concentration of 1M ammonium sulfate, pH 7.0. After loading, the column was washed to baseline with equilibration buffer. The column was eluted with 6M urea, 20 mM HEPES, 0.6M ammonium sulfate, 300 mM NaCl, pH 7.0, and then with 4M guanidine, 20 mM sodium phosphate, pH 7.0.

Two alternative cation-exchange chromatography schemes (A and B) were exploited in the purification of OP-1 from colostrum, as follows. For both schemes, 200 ml of S-Sepharose (Sigma) was poured into a 5×10 cm Bio-Rad econocolumn (Bio-Rad, Inc. Cambridge.)

Scheme A: The colostrum, which had been diluted to 6M urea, 20 mM sodium phosphate, pH 7.0, was loaded onto a column equilibrated with 6M urea, 20 mM sodium phosphate, 50 mM NaCl, pH 7.0. Elution was stepwise, with 6M urea, 20 mM sodium phosphate, 100 mM and then 500 mM NaCl, pH 7.0; and the final wash was with 4M guanidine, 20 mM sodium phosphate, pH 7.0. The Phenyl-Sepharose column was run as described above, except that sodium phosphate was used as the running buffer instead of HEPES. The Phenyl-Sepharose bound fraction (0.0M ammonium sulfate eluate) from scheme A then was dialyzed into 6M urea, 20 mM Hepes, 500 mM NaCl, pH 7.0, before it was applied to the Cu++-IMAC column, which was run as described below.

Scheme B: The alternative S-Sepharose purification was performed as follows. Ethanol-precipitated protein was loaded onto an S-Sepharose column equilibrated in 6M urea, 20 mM MES, 50 mM NaCl, pH 6.5. Elution was stepwise with 6M urea, 20 mM MES, 100 mM NaCl and then 500 mM NaCl, and finally 4M guanidine, 20 mM sodium phosphate, pH 7.0. The Phenyl-Sepharose column was run as described above, with the 0.0M ammonium sulfate eluate then applied to a Cu++-IMAC column.

step 2. Cu++IMAC Chromatography

The Cu++IMAC purification step was performed as follows. 10 ml of Pharmacia Fast Flow Chelating Resin were charged with 0.2M cupric sulfate, and equilibrated with 6M urea, 20 mM HEPES, 0.5M NaCl, pH 7.0. After loading, the column was washed to baseline with equilibration buffer. Elution from the column was stepwise, using equilibration buffer containing 1 mM, 5 mM, or 10 mM imidazole. The column then was stripped with equilibration buffer containing 10 mM EDTA. The 10 mM imidazole elution was dialyzed against water/0.1% TFA, then against 30% acetonitirile/0.1% TFA.

step 3. Reverse Phase Chromatography

The C-18 reverse phase chromatography purification step was performed as follows. An HPLC C-18 semi-prep column was used for the final purification step. The gradient used was 30–50% acetonitrile/0.1% TFA over 60 minutes at 3 ml/minutes. After the sample was loaded, the column was washed to baseline with 30% acetonitrile/0.1% TFA before the gradient is started. Fractions collected were 3 ml in size. Chromatograms were read at 214 nm.

(a) OP-1 from Rat Mammary Gland Extract

Mammary glands were obtained from 2 female Long Evan rats (Charles River Labs, Wilmington, Mass.) one week post-partum. The excised glands were mildly homogenized in 6M urea, 20 mM methylethansulfonate (MES), 0.5M NaCl, pH 6.5 using a polytron homogenizer. The suspension then was centrifuged for 20 minutes at 8,000 RPM, and the supernatant removed for further purification.

Following S-Sepharose chromatography, fractions containing 6M urea, 20 mM MES containing 500 mM NaCl, also appeared to contain OP-1 as determined by SDS and immunoblot, and were applied to the Phenyl-Sepharose column. The eluate from the 6M urea, 20 mM HEPES, 300 mM NaCl, pH 7.0 elution step from this column were found to contain OP-1. This eluate then was applied to a Cu++-IMAC column. Eluate fractions found to contain OP-1 were then applied to the C-18 column and chromatographed as described.

Figure 1B:
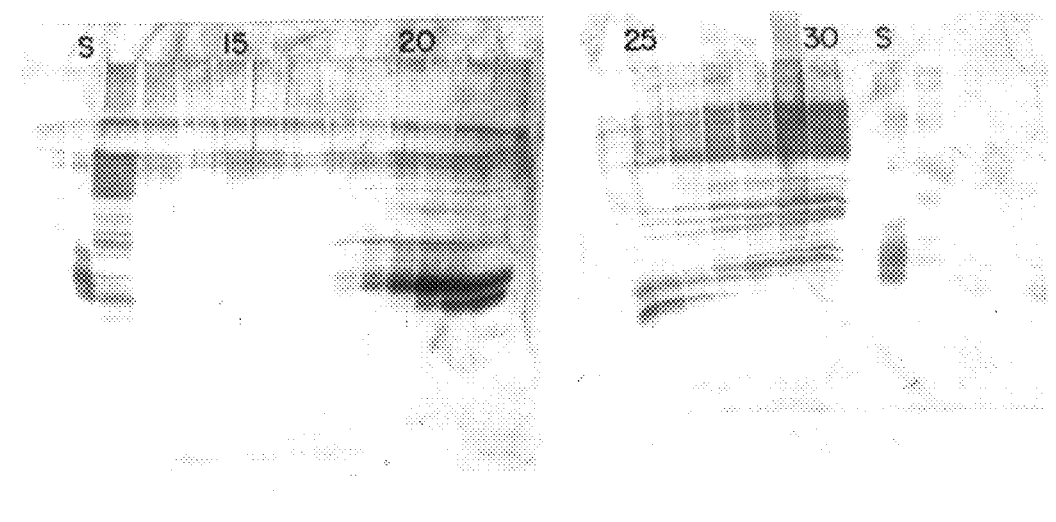

FIG. 1(A) shows the chromatogram and 1(B) the corresponding Western blot for fractions from the C-18 reverse phase chromatography step run under reducing conditions. Lane S of the Western blot is a standard, containing reduced, purified, recombinantly-produced OP-1. The arrows show molecular weight markers corresponding to 17, 27, and 39 Kd. The reduced monomer run at approximately 16–18 Kd; the oxidized homodimer at approximately 36 Kd. Lanes 13–30 represent the corresponding fractions of the C-18 reverse phase column as numbered in FIG. 1(A). As can be seen in FIG. 1(B), mammary extract OP-1 elutes primarily in fractions 21–25 from this final chromatography step.

(b) OP-1 from Bovine Colostrum

Colostrum is the first milk to be produced by the mother following birth. Approximately 5 gallons of bovine colostrum were obtained from a local dairy farm and delipidated by centrifugation (8000 rpm for approximately 10 min. at 4° C.). The supernatant then was filtered through cheese cloth. The filtered supernatant was stored in 500 ml aliquots at 70° C.

50 ml of colostrum were diluted with 100 ml of 9M urea, 30 mM sodium phosphate, pH 7.0. Alternately, 50 ml of colostrum was added to 50 ml of 8M guanidine-HCl, 50 mM Tris, pH 7.2 and precipitated with 40%, then 85% ice cold ethanol. The pellet was washed with 90% cold ethanol and lyophilized overnight. The lyophilized pellet was resuspended in 6M urea, 20 mM MES, 500 mM NaCl, pH 6.5, stirred overnight at 4° C., and centrifuged at 9,000 RPM for 10 minutes to clarify the suspension before loading onto the column as described in schemes A and B, above.

Following S-Sepharose chromatography by scheme A, both the 100 mM and the 500 mM eluate fractions were found to contain OP-1, with the 100 mM fraction containing relatively more morphogen. This fraction then was loaded onto the Phenyl-Sepharose column following dilution with an equal volume of 6M urea, 20 mM sodium phosphate, 2M ammonium sulfate, and 300 mM NaCl.

Following S-Sepharose chromatography by scheme B, the 500 mM NaCl eluate was found to contain OP-1 and was loaded onto a Phenyl-Sepharose column as described above, following dilution with 6M urea, 40 mM HEPES, 2M ammonium sulfate, pH 7.0.

Following Cu++IMAC chromatography OP-1 was identified in the 5 mM and 10 mM imidazole eluates for both purification schemes, and was dialyzed for further purification on the C-18 column.

Figure 2A:
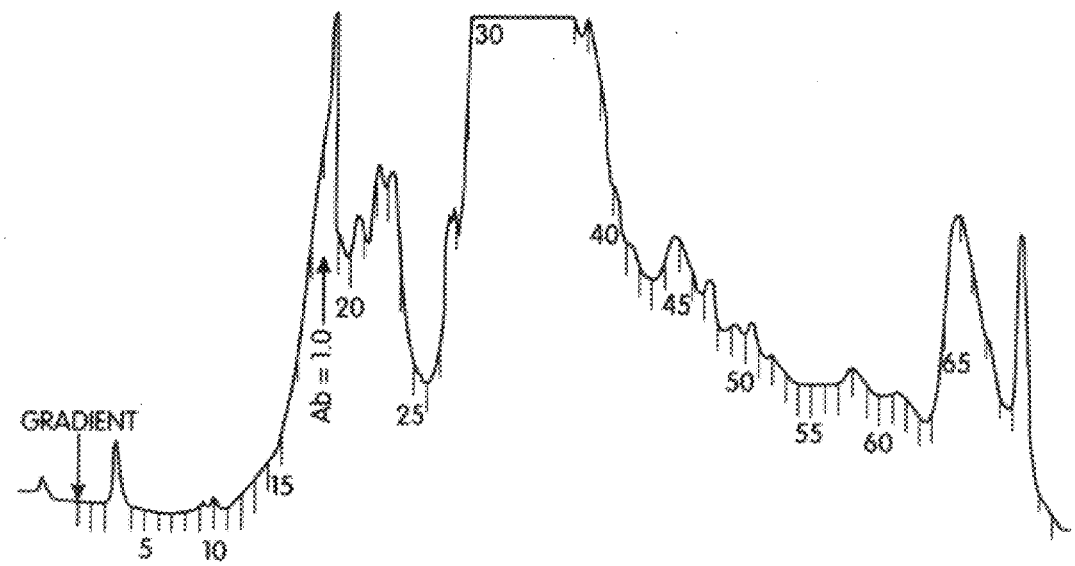
FIG. 2A and B shows relative amounts of protein present in bovine colostrum eluate fractions from purification scheme A of a C-18 reverse phase chromatography column (A), and the corresponding results of a Western blot under reduced (1) and oxidized (2) conditions (B)
Figure 2B:
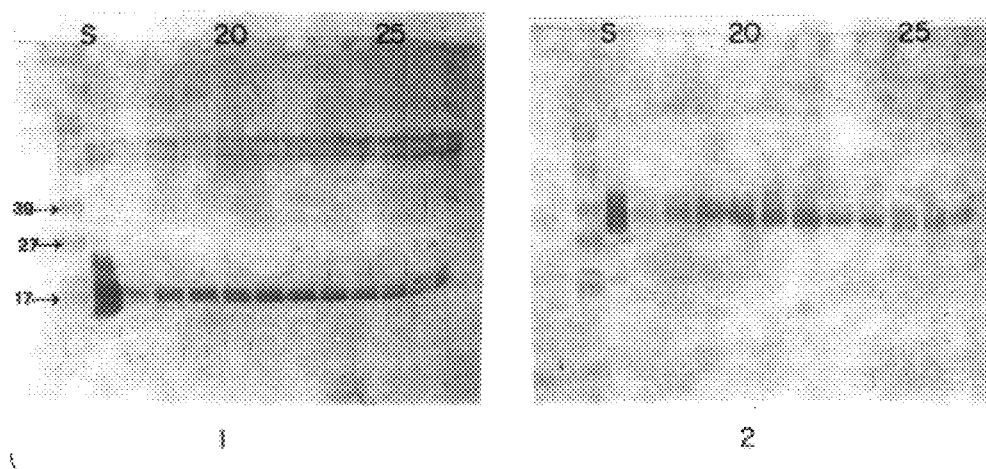
Figure 3A:
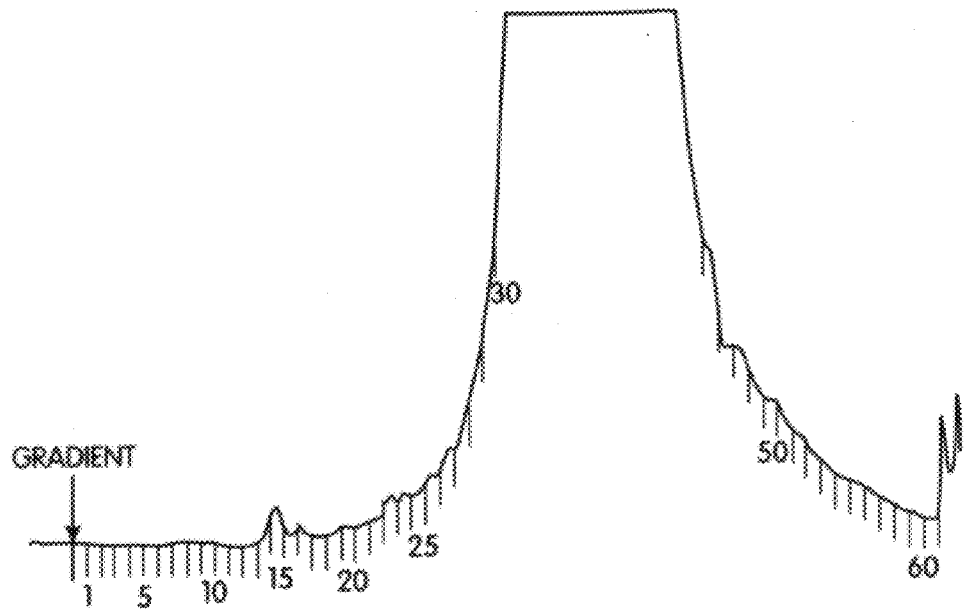
FIG. 3A and B shows relative amounts of protein present in bovine colostrum eluate fractions from purification scheme B of a C-18 reverse phase chromatography column (A), and the corresponding results of a Western Blot under reduced conditions (B)
Figure 3B:
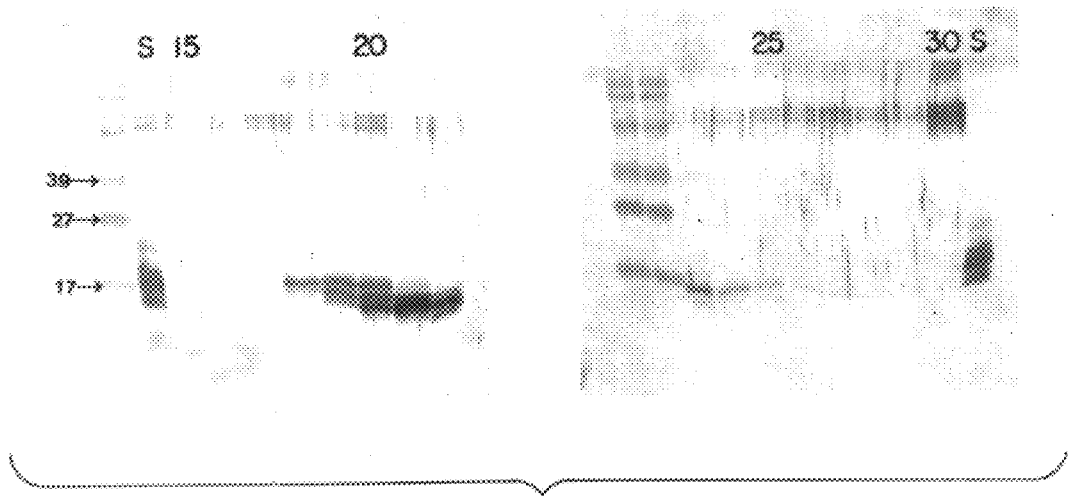

Both purification schemes produce purified OP-1, as determined by immunoblot. FIG. 2 shows the chromatogram (A) and corresponding Western blot (B) for results of purification scheme A (FIG. 2B-1, reduced and FIG. 2B-2, oxidized); and FIG. 3 shows the chromatogram (A) and Western blot (B, reduced) for C-18-purified protein from scheme B. As for FIG. 1B, lane S in FIGS. 2B and 3B is a standard, containing purified, recombinantly produced OP-1; 17, 27 and 39 are molecular weight markers, and lane numbers correspond to fraction numbers in the corresponding chromatograms. OP-1 purified by scheme A appears predominantly in fractions 18–27, and OP-1 purified by scheme B appears predominantly in fractions 18–25.

OP-1 from 57-day milk

Milk was obtained from the same cow from which the colostrum came, 57 days after the birth of the calf. The milk was delipidated by centrifugation at 10,000 RPM for 15 minutes, and the milk was poured off and away from the fat layer.

100 ml of milk then were diluted with 200 ml of 9M urea, 30 mM MES, pH 6.5 and loaded onto a 200 ml S-Sepharose column which had been equilibrated with 6M urea, 20 mM MES, 50 mM NaCl, pH 6.5. Elution was with 6M urea, 20 mM MES, 100 mM and 500 mM NaCl, and 4M guanidine, 20 mM sodium phosphate, pH 7.0. The 500 mM elution was put over a Phenyl-Sepharose column after being diluted with an equal volume of 6M urea, 20 mM MES, 2M ammonium sulfate, pH 7.0.

The Phenyl-Sepharose column then was run as described above. The Phenyl-Sepharose-bound sample was eluted and applied to a Cu++IMAC column, prepared and run as described above. The 10 mM imidazole eluate was found to contain OP-1 and was dialyzed for further purification on the C-18 column.

Figure 4A:
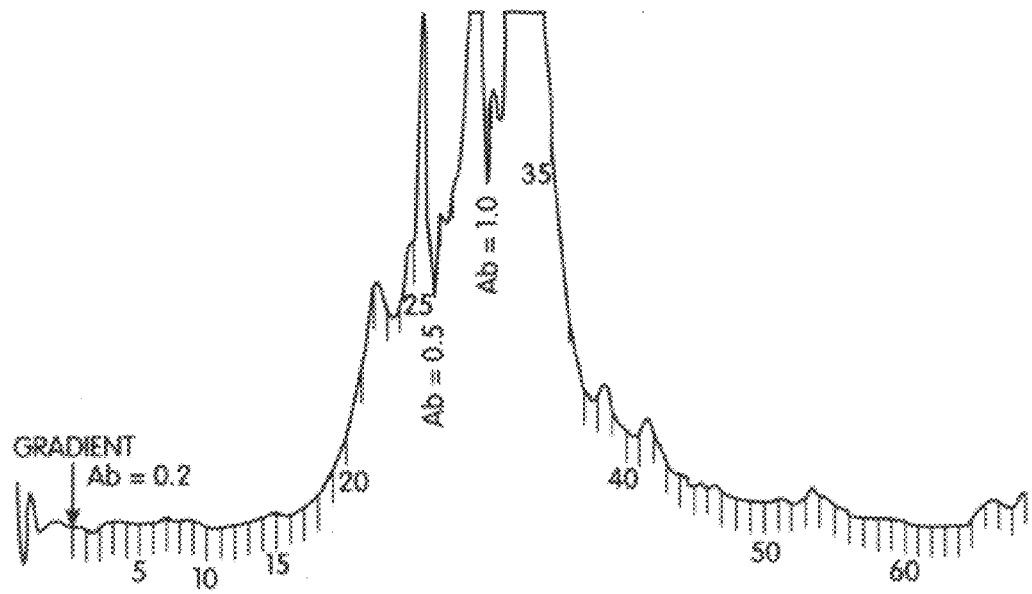
FIG. 4A and B shows relative amounts of protein present in bovine 57 day milk eluate fractions of a C-18 reverse phase chromatography column (A), and the corresponding results of a Western Blot under reduced (1) and oxidized (2) conditions (B)
Figure 4B:
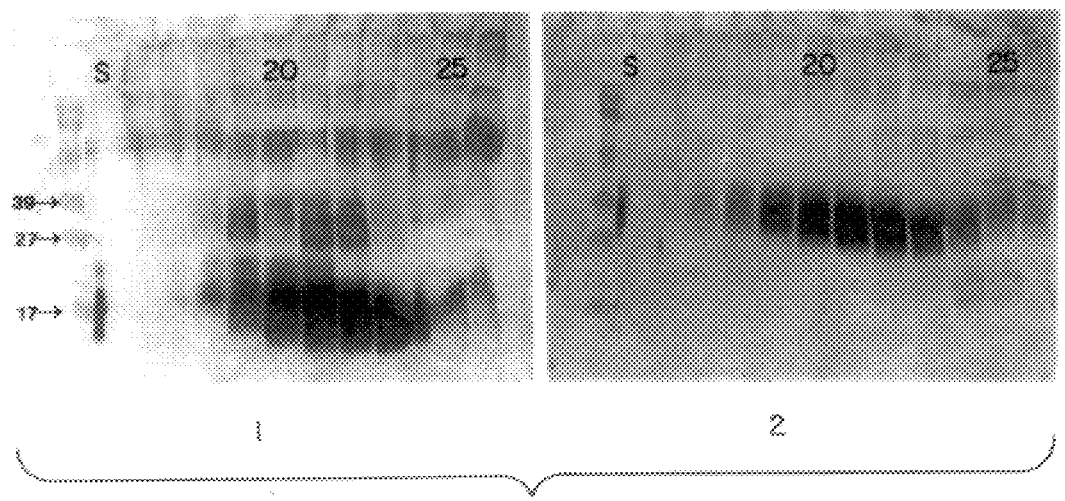

The C-18 reverse phase chromatography column and gradient were performed as described above. The results are presented in FIG. 4A (chromatogram) and 4B (immunoblot, 10B-1, oxidized; 4B-2, reduced.) As above, lane S is a standard, containing purified, recombinantly produced OP-1; 17, 27, and 39 are molecular weight markers, and the lane numbers correspond to the fractions numbers in FIG. 4A. OP-1 purified from 57-day milk appears predominantly in fractions 18–26.

1.2 OP-1 Characterization by immunoreactivity

OP-1 purified from the different milk sources as described above also were characterized by Western blotting using antibodies raised against OP-1 and BMP2. Antibodies were prepared using standard immunology protocols well known in the art, and as described in Example 8, below using full-length *E. coli*-produced OP-1 and BMP2 as the immunogens.

Figure 5:
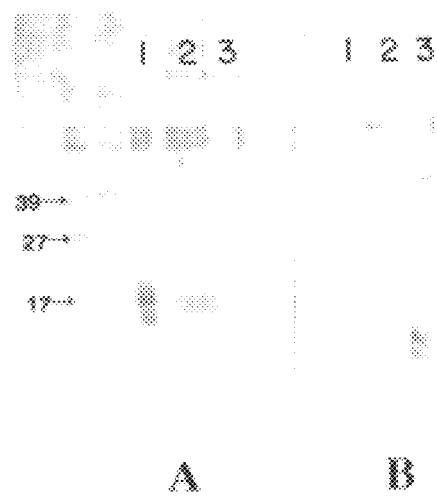
FIG. 5 shows Western Blot analysis of bovine colostrum using OP-1 and BMP2-specific antibodies.

As shown in FIG. 5 OP-1 purified from colostrum reacts with the anti-OP-1 antibody, but not with anti-BMP2 antibody. In FIG. 5A and B, lane 1 contains reduced, purified, recombinantly-produced OP-1; lane 2 contains C-18 purified bovine colostrum, and lane 3 contains reduced COP-16, a biosynthetic construct having morphogenic activity and an amino acid sequence modeled on the proteins described herein, but having highest amino acid sequence homology with BMP2 (see U.S. Pat. No. 5,011,691 for the COP-16 amino acid sequence.) In FIG. 5A the gel was probed with anti-OP-1 antibody; in FIG. 5B, the gel was probed with anti-BMP2 antibody. As can be seen in the figure, anti-OP-1 antibody hybridizes with protein in lanes 1 and 2, but not 3; while anti-BMP2 antibody hybridizes with lane 3 only.

C-18 purified mammary gland extract and 57-day milk also were shown to react with anti-OP-1 antibodies, including antibody raised against the full length *E. coli* OP-1, full length mammalian-produced OP-1, and the OP-1 Ser-17-Cys peptide (e.g., the OP-1 N-terminal 17 amino acids).

1.3 OP-1 Characterization by Activity

The morphogenic activity of OP-1 purified from mammary gland extract was evaluated in vivo as follows. 33% of each OP-1 immunoreactive fraction of C-18-purified mammary gland extract was lyophilized and resuspended in 220 μl of 50% acetonitrile/0.1% TFA. After vortexing, 25 mg of collagen matrix was added. The samples were lyophilized overnight, and implanted in Long Evans rats (Charles River Laboratories, Wilmington, Mass., 28–35 days old). Each fraction was implanted in duplicate. For details of the collagen matrix implantation procedure, see, for example, U.S. Pat. No. 4,968,590, hereby incorporated by reference. After 12 days, the implants were removed and evaluated for new bone formation by histological observation.

Figure 6A:
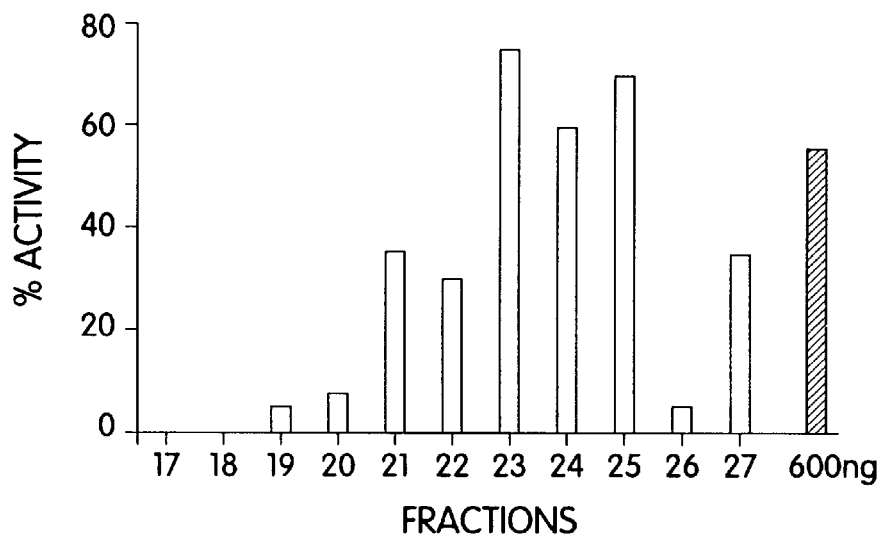
FIG. 6A and B show results of in vivo and in vitro activity assays, respectively, for the corresponding fractions shown in FIG. 1.

The results are presented in FIG. 6A, where "% activity" refers to the % of bone formation/total area covered by bone in the histology sample. In the figure, solid bars represent implants using mammary extract-derived OP-1, where the fraction numbers correspond to the related fractions eluted from the C-18 reverse phase column (see FIG. 1B), and the hatched bar represents implants using recombinantly produced OP-1 (600 ng). The results demonstrate that the peak bone forming activity of C-18-purified mammary gland extract corresponds with the immunoreactive fraction peaks of FIG. 1B (compare FIG. 6A and 1B.)

Figure 6B:
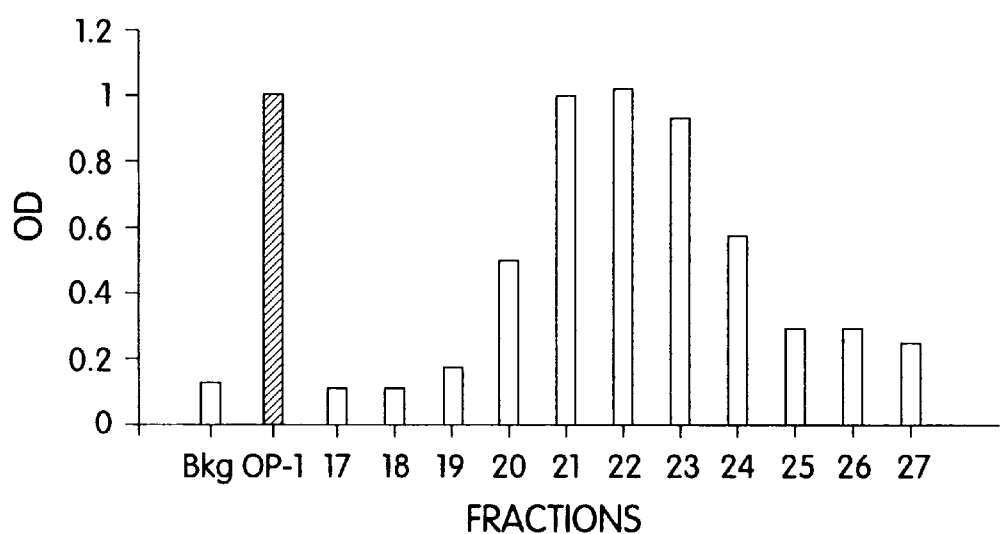

Similarly, the morphogenic activity of OP-1 purified from mammary gland extract was evaluated in vitro by measuring alkaline phosphatase activity in vitro using the following assay. Test samples were prepared using 15–20% of individual immunoreactive fractions from the C-18 run which were precipitated and resuspended in a smaller volume of 50% acetonitrile/0.1% TFA. Alkaline phosphatase activity was tested using ROS 17/2.8 cells (Rat Osteosarcoma, e.g., obtained, for example, from Dr. Robert J. Majeska, Mt. Sinai Medical Center, New York, N.Y., in a standard alkaline phosphatase activity assay (see, for example, U.S. Pat. No. 4,968,590). The results, presented in FIG. 6B, indicate that the immunoreactive fractions obtained from C-18-purified mammary gland extract correspond with alkaline phosphatase activity in vitro (compare FIG. 6B and FIG. 1B.) In FIG. 6B solid bars represent assays performed with mammary gland-purified OP-1, where the fraction numbers correspond to the related fractions eluted from the C-18 reverse phase column (see FIG. 1B), the hatched bar represents the assay performed with purified, recombinantly-produced OP-1 (100 ng/ml), and the cross-hatched bar represents background. As for FIG. 6A, alkaline phosphatase activity corresponds with immunoreactivity of the C-18-purified extract (compare FIG. 6B and 1B.)

Example 2.
Morphogen Identification in Human Serum

Figure 7:
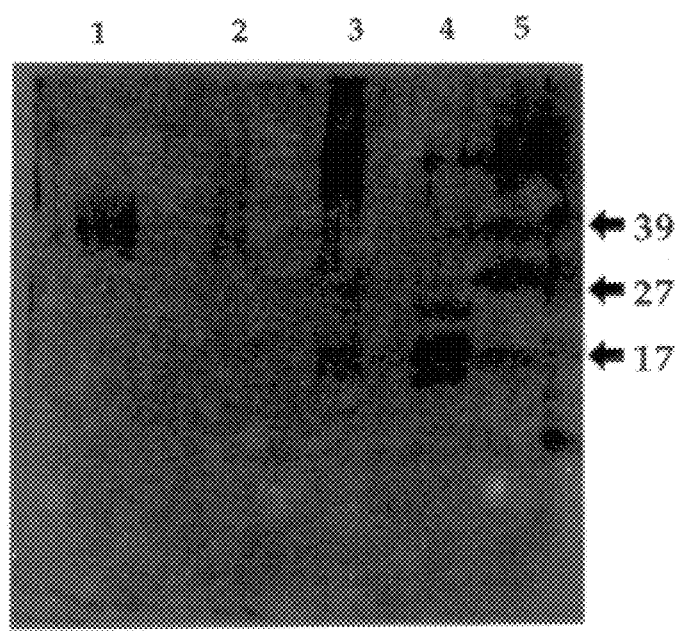
FIG. 7 is a photomicrograph of an immunoblot showing the presence of hOP-1 in serum.

OP-1 was detected in human serum using the following assay. A monoclonal antibody raised against mammalian, recombinantly produced OP-1 using standard immunology techniques well described in the art and described generally in Example 8, was immobilized by passing the antibody over an activated agarose gel (e.g., Affi-Gel™, from Bio-Rad Laboratories, Richmond, Calif., prepared following manufacturer's instructions), and used to purify OP-1 from serum. Human serum then was passed over the column and eluted with 3M K-thiocyanate. K-thiocyanante fractions then were dialyzed in 6M urea, 20 mM $PO_4$, pH 7.0, applied to a C8 HPLC column, and eluted with a 20 minute, 25–50% acetonitrile/0.1% TFA gradient. Mature, recombinantly produced OP-1 homodimers elute between 20–22 minutes. Fractions then were collected and tested for the presence of OP-1 by standard immunoblot. FIG. 7 is an immunoblot showing OP-1 in human sera under reducing and oxidized conditions. In the figure, lanes 1 and 4 are OP-1 standards, run under oxidized (lane 1) and reduced (lane 4) conditions. Lane 5 shows molecular weight markers at 17, 27 and 39 kDa. Lanes 2 and 3 are human sera OP-1, run under oxidized (lane 2) and reduced (lane 3) conditions.

Example 3.
Morphogen-Induced CAM Expression

The morphogens described herein induce CAM expression as part of their induction of morphogenesis. CAMs are morphoregulatory molecules identified in all tissues as an essential step in tissue development. N-CAMs, which comprise at least 3 isoforms (N-CAM-180, N-CAM-140 and N-CAM-120, where "180", "140" and "120" indicate the apparent molecular weights of the isoforms as measured by polyacrylamide gel electrophoresis) are expressed at least transiently in developing tissues, and permanently in nerve tissue. Both the N-CAM-180 and N-CAM-140 isoforms are expressed in both developing and adult tissue. The N-CAM-120 isoform is found only in adult tissue. Another neural CAM is L1.

CAMs are implicated in normal tissue development; N-CAMs are implicated in appropriate neural development, including appropriate neurulation, neuronal migration, fasciculation, and synaptogenesis. Inhibition of N-CAM production, as by complexing the molecule with an N-CAM-specific antibody, inhibits retina organization, including retinal axon migration, and axon regeneration in the peripheral nervous system, as well as axon synapses with target muscle cells. CAMs also have been postulated as part of a morphoregulatory pathway whose activity is induced by a to date unidentified molecule (See, for example, Edelman, G. M. (1986) Ann. Rev. Cell Biol. 2: 81–116). Without being limited to any given theory, the morphogens described herein may act as the inducer of this pathway.

The morphogens described herein can stimulate CAM production. As described below, the morphogens stimulate L1 and N-CAM production, including all three isoforms of the N-CAM molecule, in nerve tissue. A detailed description of this protocol is described in copending U.S. Ser. No. 922,813 the disclosure of which is incorporated hereinabove by reference.

Figure 8A:
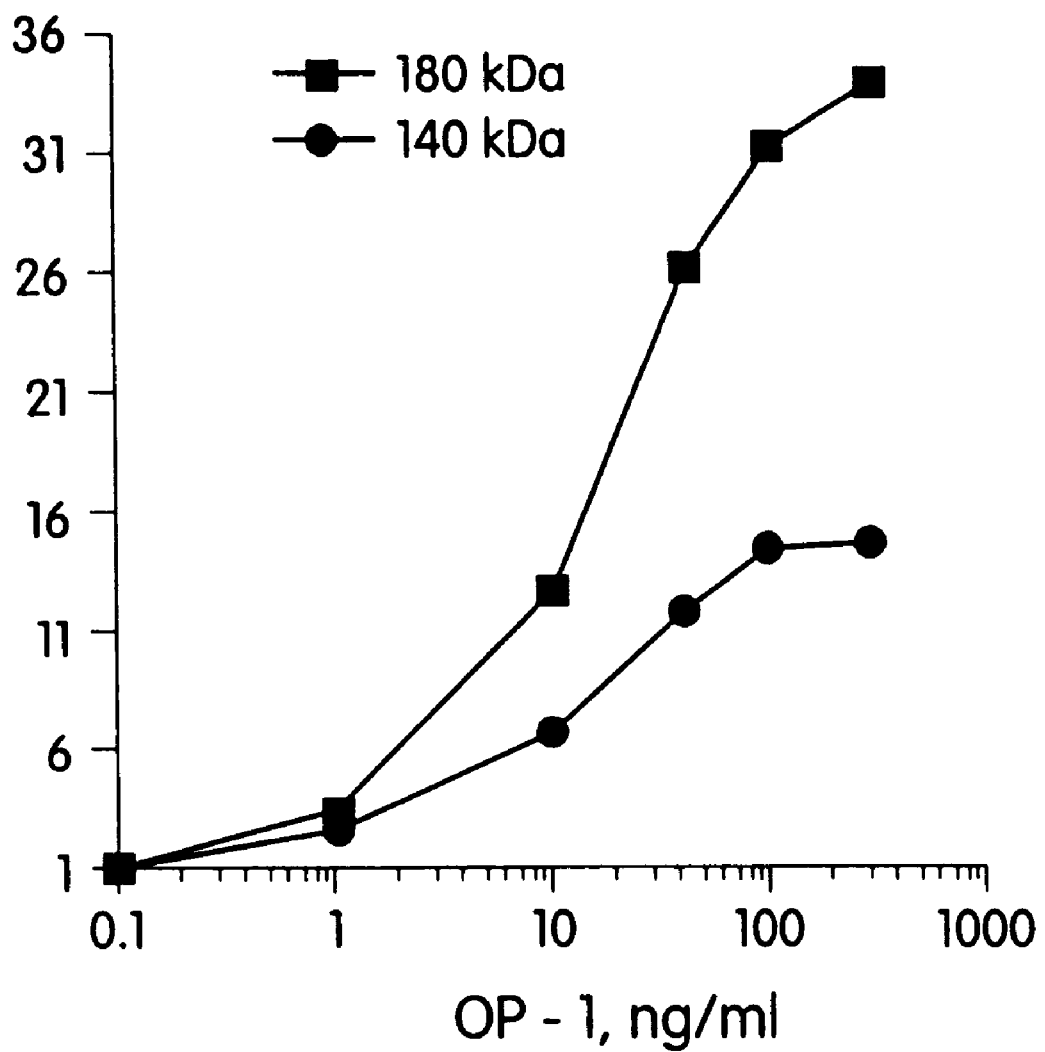
FIG. 8A is a dose response curve for the induction of the 180 kDa and 140 kDa N-CAM isoforms in morphogen-treated NG108-15 cells.
Figure 8B:
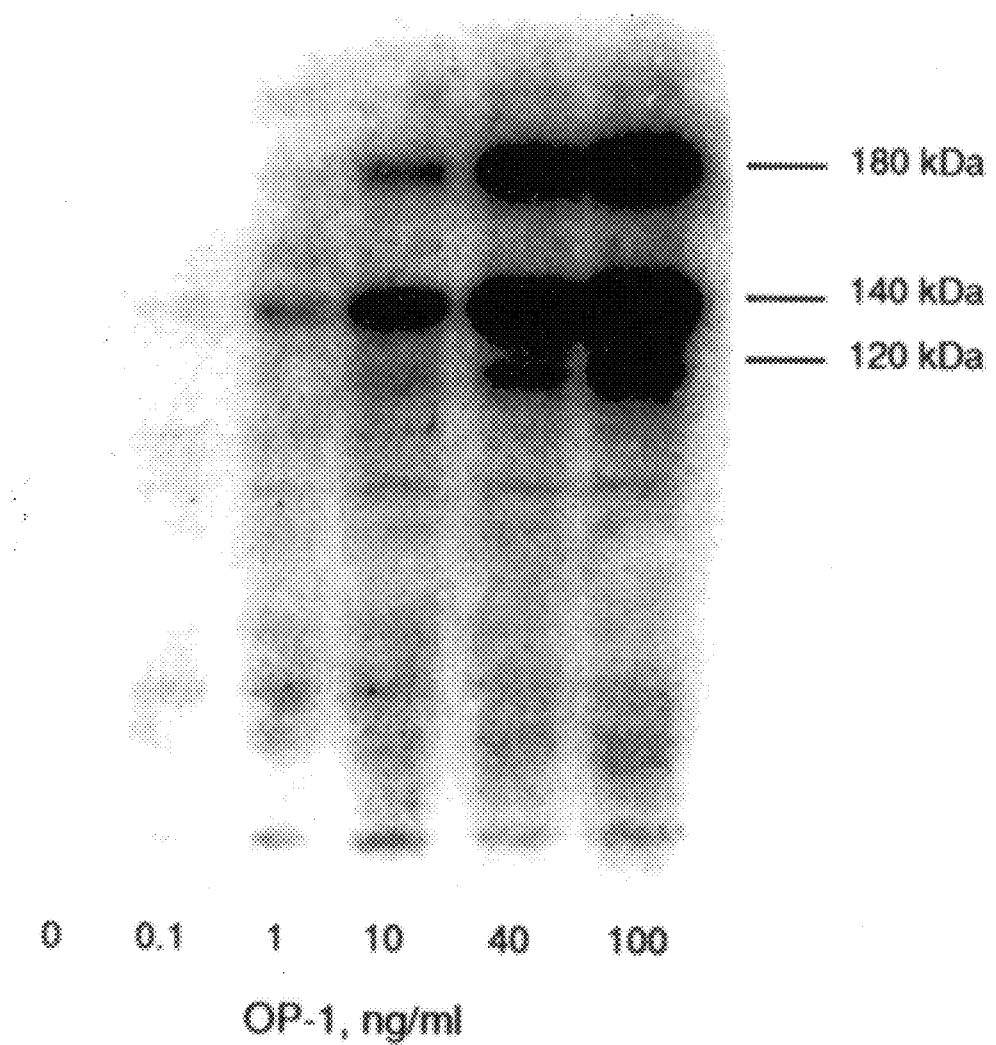
FIG. 8B is a photomicrograph of a Western blot of whole cell extracts from morphogen-treated NG108-15 cells with an N-CAM-specific antibody.

In this example NG108-15 cells were cultured for 4 days in the presence of increasing concentrations of OP-1 and standard Western blots performed on whole cells extracts. The NG108-15 cell line is a hybrid cell line (neuroblastoma x glioma, American Type Culture Collection, Rockville, Md.). N-CAM isoforms were detected with an antibody which crossreacts with all three isoforms, mAb H28.123, obtained from Sigma Chemical Co., St. Louis, the different isoforms being distinguishable by their different mobilities on an electrophoresis gel. Control NG108-15 cells (untreated) express both the 140 kDa and the 180 kDa isoforms, but not the 120 kDa, as determined by western blot analyses using up to 100 $\mu$g of protein. As shown in FIG. 8, treatment of NG108-15 cells with OP-1 resulted in a dose-dependent increase in the expression of the 180 kDa and 140 kDa isoforms, as well as the induction of the 120 kDa isoform. FIG. 8B is a Western blot of OP1-treated NG108-15 cell extracts, probed with mAb H28.123, showing the induction of all three isoforms. FIG. 8A is a dose response curve of N-CAM-180 and N-CAM-140 induction as a function of morphogen concentration. N-CAM-120 is not shown in the graph as it could not be quantitated in control cells. However, as is clearly evident from the Western blot in FIG. 8A, N-CAM-120 is induced in response to morphogen treatment. The induction of the 120 isoform also indicates that morphogen-induced redifferentiation of transformed cells stimulates not only redifferentiation of these cells from a transformed phenotype, but also differentiation to a phenotype corresponding to a developed cell. The differential induction of N-CAM 180 and 140 isoforms seen may be because constitutive expression of the 140 isoform is close to maximum. In addition, the increase in N-CAM expression corresponded in a dose-dependent manner with the morphogen induction of multicellular aggregates.

In addition, the cell aggregation effects of OP-1 on NG108-15 cells can be inhibited with anti-N-CAM antibodies or antisense N-CAM oligonucleotides. Antisense oligonucleotides can be made synthetically on a nucleotide synthesizer, using standard means known in the art. Preferably, phosphorothioate oligonucleotides ("S-oligos") are prepared, to enhance transport of the nucleotides across cell membranes. Concentrations of both N-CAM antibodies and N-CAM antisense oligonucleotides sufficient to inhibit N-CAM induction also inhibited formation of multilayered cell aggregates. Specifically, incubation of morphogen-treated NG108-115 cells with 0.3–3 $\mu$M N-CAM antisense S-oligos, 5–500 μM unmodified N-CAM antisense oligos, or 10 μg/ml mAb H28.123 significantly inhibits cell aggregation. It is likely that morphogen treatment also stimulates other CAMs, as inhibition is not complete.

The experiments also have been performed with soluble morphogen (e.g., mature OP-1 associated with its pro domain) which also specifically induced CAM expression.

Example 4.
Effect of Morphogen Neutralization on Embryogenesis

As described in Example 7, below, at least one morphogen, OP2, is found principally in early developing embryos (8-day embryos). As described below, morphogen neutralization with morphogen-specific antibodies inhibits embryogenesis.

Morphogen inhibition in developing embryos inhibits tissue and organ development. Specifically, 9-day mouse embryo cells, cultured in vitro under standard culturing conditions, were incubated in the presence and absence of an OP-1-specific monoclonal antibody prepared using recombinantly produced, purified mature OP-1 as the immunogen. The antibody was prepared using standard antibody production means well known in the art and essentially as described for Example 9, below. After two days, the effect of the antibody on the developing embryo was evaluated by histology using standard histology procedures well known in the art. As determined by histological examination, the OP-1-specific antibody specifically inhibits eye lobe formation in the developing embryo. In particular, the diencephalon outgrowth does not develop. In addition, the heart is malformed. Moreover, in separate immunolocalization studies on embryo sections with labelled OP-1 specific antibody, the OP-1-specific antibody localizes to neural epithelia.

Similarly, morphogen activity may be demonstrated in fetal development in the mouse model using the following assay. Single lip injections comprising 10–100 μg/injection of morphogen-specific antibody are administered to pregnant female mice during each day of the gestation period and tissue development (e.g., bone development) in treated and control new mice evaluated by standard histomorphometric analysis at birth.

Finally, stimulation of endogenous morphogen antibody production in egg-laying hens interferes with shell formation in the developing eggs.

All of these data demonstrate that inhibition of morphogen activity significantly interferes with tissue development during embryogenesis.

Example 5.
Effect of Morphogen Neutralization on Juvenile Tissue Development

The effect of the morphogens described herein on tissue development in developing mammals also may be demonstrated using neutralizing antibodies specific for particular morphogens and assessing the effect of these antibodies on tissue development as described below. Specifically, anti-morphogen monoclonal and/or polyclonal antibodies may be prepared using standard methodologies including, for example, the protocol provided in Example 8, below, and provided to juveniles to inhibit the activity of endogenous morphogens.

Figure 9A:
FIG. 9 (A and B) are photographs showing the effect of morphogen-specific antibody on mouse development (9B) compared to untreated, control mice (9A).
Figure 9B:

Generally, purified antibodies are provided regularly to new born mice, e.g., 10–100 μg/injection/day for 10–15 days. At 10 or 21 days, the mice are sacrificed and the effect of morphogen on bone development assessed by body weight, gross visual examination and histology. In this example, anti-OP-1 antibodies were used in 10 μg injections/day for 14 days, and the mice were sacrificed at 21 days. As is dramatically demonstrated in FIG. 9, mice treated with OP-1 specific antibody show consistent and significant stunted growth, including reduced body length and body weight, (9B) as compared with untreated mice (9A). Histological examination showed reduced bone growth as evidenced by reduced bone size in the treated mice.

In a variation on this protocol, single lip injections also may be provided to older juveniles and adult mice (e.g., 10–100 μg) over a prolonged time (e.g., 10–15 days) to evaluate the effect or morphogen neutralization on bone growth and bone integrity and to evaluate the onset of osteoporosis.

Example 6.

Morphogen Treatment of Osteoporosis 6.1 Effect of Morphogen on Trabecular Bone in Ovariectomized (OVX) Rats Aged individuals, and particularly postmenopausal women are particularly at risk for osteoporosis. Provided below is an animal osteoporosis model demonstrating the ability of morphogens to substantially inhibit and/or reduce the tissue damage effects associated with osteoporosis, wherein osteoporosis is induced by ovary removal in rats. Bone growth is evaluated in these animals by measuring serum alkaline phosphatase and osteocalcin levels in treated and untreated rats.

Forty Long-Evans rats (Charles River Laboratories, Wilmington) weighing about 200 g each are ovariectomized (OVX) using standard surgical procedures, and ten rats are sham-operated. The ovariectomization of the rats produces an osteoporotic condition within the rats as a result of decreased estrogen production. Food and water are provided ad libitum. Eight days after ovariectomy, the rats, prepared as described above, were divided into five groups: (A), 10 sham-operated rats; (B), 10 ovariectomized rats receiving 1 ml of phosphate-buffered saline (PBS) i.v. in the tail vein; (C) 10 ovariectomized rats receiving about 1 mg of $17\beta E_2$ ($17\text{-}\beta$-estradiol $E_2$) by intravenous injection through the tail vein; (D) 9 ovariectomized rats receiving daily injections of approximately 2 μg of morphogen by tail vein for 22 days; and (E) 9 ovariectomized rats receiving daily injections of approximately 20 μg of morphogen by tail vein for 22 days. In this example, OP-1 was the morphogen tested.

On the 15th and 21st day of the study, each rat was injected with 5 mg of tetracycline, and on day 22, the rats were sacrificed. The body weights, uterine weights, serum alkaline phosphate levels, serum calcium levels and serum osteocalcin levels then were determined for each rat. The results are shown in Tables III and IV.

TABLE III

Body Weights, Uterine Weights and Alkaline Phosphatase

| Group | Body Weights (g) | Uterine Weights (g) | Alk. Phosphatase (U/L) |
| --- | --- | --- | --- |
| A-SHAM | 250.90 ± 17.04 | 0.4192 ± 0.10 | 43.25 ± 6.11 |
| B-OVX + PBS | 273.40 ± 16.81 | 0.1650 ± 0.04 | 56.22 ± 6.21 |
| C-OVX + E2 | 241.66 ± 21.54 | 0.3081 ± 0.03 | 62.66 ± 4.11 |
| D-OVX + OP-1 (2 μg) | 266.67 ± 10.43 | 0.1416 ± 0.03 | 58.09 ± 12.97 |
| E-OVX + OP-1 (20 μg) | 272.40 ± 20.48 | 0.1481 ± 0.05 | 66.24 ± 15.74 |

TABLE IV

Serum Calcium and Serum Osteocalcin Levels

| Group | Serum Calcium (ng/dl) | Serum Osteocalcin (ng/ml) |
|---|---|---|
| A-SHAM | 8.82 ± 1.65 | 64.66 ± 14.77 |
| B-OVX + PBS | 8.95 ± 1.25 | 69.01 ± 10.20 |
| C-OVX + E2 | 9.20 ± 1.39 | 67.13 ± 17.33 |
| D-OVX + OP-1 (2 μg) | 8.77 ± 0.95 | 148.50 ± 84.11 |
| E-OVX + OP-1 (20 μg) | 8.67 ± 1.94 | 182.42 ± 52.11 |

The results presented in Table III and IV show that intravenous injection of morphogen into ovariectomized rats produces a significant increase in serum alkaline phosphatase and serum osteocalcin levels and demonstrates that systemic administration of the morphogen stimulates bone formation in osteoporotic bone.

6.2 Histomorphometric Analysis of Morphogen on the Tibia Diaphysis in Ovariectomized(OVX) Rats Fifteen female Long-Evans rats weighing about 160 g were ovariectomized (OVX) to produce an osteoporotic condition and five rats were sham operated (Charles River Laboratories, Wilmington, Mass.) as described for Example 8. Food and water were provided ad libitum. Twenty-two days after ovariectomy, the rats were divided into four groups: (A) sham-operated (1 ml of PBS by intravenous injection through tail vein (5 rats); (B) OVX, into which nothing was injected (5 rats); (C) OVX, receiving about 1 mg of $17\beta E_2$ by intravenous injection through the tail vein (5 rats), and (D) OVX, receiving about 1 βg of morphogen by intravenous injection through the tail vein (5 rats). In this example, OP-1 was morphogen tested.

The rats were injected daily as described for seven days, except no injections were given on the thirteenth day. The rats then were sacrificed on the nineteenth day. The tibial diaphyseal long bones then were removed and fixed in ethanol and histomorphometric analysis was carried out using standard procedures well known in the art. The results are shown in Table V.

TABLE V

| MEASUREMENT | (A) CONTROL | (B) OVX | (C) OVX + $E_2$ | (D) OVX + OP-1 |
|---|---|---|---|---|
| Longitudinal Growth Rate (μm/day) | 20.2 ± 0.3 | 19.4 ± 0.2 | 4.9 ± 0.5 | 17.9 ± 0.9 |
| Cancellous Bone Volume (BV/TV, bone vol/total vol) | 20.2 ± 1.5 | 13.0 ± 1.6 | 13.7 ± 2.1 | 16.6 ± 1.8 |
| Cancellous Bone Perimeter (mm) | 16.2 ± 1.8 | 9.6 ± 0.9 | 11.5 ± 1.1 | 12.2 ± 0.7 |
| Labeled Cancellous Perimeter (%) | 35.5 ± 1.5 | 51.9 ± 5.6 | 58.0 ± 4.2 | 39.2 ± 1.9 |
| Mineral Apposition Rate (μm/day) | 1.76 ± 0.14 | 2.25 ± 0.16 | 1.87 ± 0.08 | 1.86 ± 0.20 |

The results presented in Table V confirm the results of Example 6.1, namely that intravenous injection of OP-1 into ovariectomized rats stimulates bone growth for bone which had been lost due to the drop in estrogen within the individual rat. Specifically, the inhibition of cancellous bone volume in OVX rats is repaired by the systemically provided morphogen. In addition, in morphogen-treated rats the labelled cancellous perimeter and mineral apposition rate now return to levels measured in the control, sham-operated rats. Moreover, morphogen treatment does not inhibit longitudinal bone growth, unlike estrogen treatment, which appears to inhibit bone growth significantly. Accordingly, systemic administration of a morphogen in therapeutically effective concentrations effectively inhibits loss of bone mass in a mammal without inhibiting natural bone formation.

Example 7.
Identification of Morphogen-Expressing Tissue

Determining the tissue distribution of morphogens may be used to identify different morphogens expressed in a given tissue, as well as to identify new, related morphogens. Tissue distribution also may be used to identify useful morphogen-producing tissue for use in screening and identifying candidate morphogen-stimulating agents. The morphogens (or their mRNA transcripts) readily are identified in different tissues using standard methodologies and minor modifications thereof in tissues where expression may be low. For example, protein distribution may be determined using standard Western blot analysis or immunofluorescent techniques, and antibodies specific to the morphogen or morphogens of interest. Similarly, the distribution of morphogen transcripts may be determined using standard Northern hybridization protocols and transcript-specific probes.

Any probe capable of hybridizing specifically to a transcript, and distinguishing the transcript of interest from other, related transcripts may be used. Because the morphogens described herein share such high sequence homology in their active, C-terminal domains, the tissue distribution of a specific morphogen transcript may best be determined using a probe specific for the pro region of the immature protein and/or the N-terminal region of the mature protein. Another useful sequence is the 3' non-coding region flanking and immediately following the stop codon. These portions of the sequence vary substantially among the morphogens of this invention, and accordingly, are specific for each protein. For example, a particularly useful Vgr-1-specific probe sequence is the PvuII-SacI fragment, a 265 bp fragment encoding both a portion of the untranslated pro region and the N-terminus of the mature sequence (see Lyons et al. (1989) *PNAS* 86: 4554–4558 for a description of the cDNA sequence). Similarly, particularly useful mOP-1-specific probe sequences are the BstX11-BglI fragment, a 0.68 Kb sequence that covers approximately two-thirds of the mOP-1 pro region; a StuI-StuI fragment, a 0.2 Kb sequence immediately upstream of the 7-cysteine domain; and the Ear1-Pst1 fragment, an 0.3 Kb fragment containing a portion of the 3'untranslated sequence (See Seq. ID No. 18, where the pro region is defined essentially by residues 30–291.) Similar approaches may be used, for example, with hOP-1 (Seq. ID No. 16) or human or mouse OP-2 (Seq. ID Nos. 20 and 22.)

Using these morphogen-specific probes, which may be synthetically engineered or obtained from cloned sequences, morphogen transcripts can be identified in mammalian tissue, using standard methodologies well known to those having ordinary skill in the art. Briefly, total RNA is prepared from various adult murine tissues (e.g., liver, kidney, testis, heart, brain, thymus and stomach) by a standard methodology such as by the method of Chomczyaski et al. ((1987) *Anal. Biochem* 162: 156–159) and described below. Poly (A)+RNA is prepared by using oligo (dT)-cellulose chromatography (e.g., Type 7, from Pharmacia LKB Biotechnology, Inc.). Poly (A)+RNA (generally 15 µg) from each tissue is fractionated on a 1% agarose/formaldehyde gel and transferred onto a Nytran membrane (Schleicher & Schuell). Following the transfer, the membrane is baked at 80° C. and the RNA is cross-linked under UV light (generally 30 seconds at 1 mW/cm$^2$). Prior to hybridization, the appropriate probe is denatured by heating. The hybridization is carried out in a lucite cylinder rotating in a roller bottle apparatus at approximately 1 rev/min for approximately 15 hours at 37° C. using a hybridization mix of 40% formamide, 5×Denhardts, 5×SSPE, and 0.1% SDS. Following hybridization, the non-specific counts are washed off the filters in 0.1×SSPE, 0.1% SDS at 50° C.

Examples demonstrating the tissue distribution of various morphogens, including Vgr-1, OP-1, BMP2, BMP3, BMP4, BMP5, GDF-1, and OP-2 in developing and adult tissue are disclosed in co-pending U.S. Ser. No. 08/404,113, and in Ozkaynak, et al., (1991) *Biochem. Biophys. Res. Commn.* 179: 116–123, and Ozkaynak, et al. (1992) (JBC, in press), the disclosures of which are incorporated herein by reference. Using the general probing methodology described herein, northern blot hybridizations using probes specific for these morphogens to probe brain, spleen, lung, heart, liver and kidney tissue indicate that kidney-related tissue appears to be the primary expression source for OP-1, with brain, heart and lung tissues being secondary sources. Lung tissue appears to be the primary tissue expression source for Vgr-1, BMP5, BMP4 and BMP3. Lower levels of Vgr-1 also are seen in kidney and heart tissue, while the liver appears to be a secondary expression source for BMP5, and the spleen appears to be a secondary expression source for BMP4. GDF-1 appears to be expressed primarily in brain tissue.

Of particular relevance to the present application, OP-1 also is detected in adult rat stomach and gut tissue. Moreover, OP-2 appears to be expressed primarily in early embryonic tissue. Specifically, northern blots of murine embryos and 6-day post-natal animals shows abundant OP2 expression in 8-day embryos. Expression is reduced significantly in 17-day embryos and is not detected in post-natal animals.

In addition, labelled soluble OP-1 (iodinated with $^{125}$I, using standard labelling procedures well known in the art) and injected into the rat tail vein also is localized to the stomach tissue within 30 minutes of injection.

Example 8.
Detecting Morphogenic Protein in Solution by Immunoassay

Morphogens are readily detected in solution with a standard immunoassay, using a polyclonal or monoclonal antibody specific for that protein and standard Western blot, ELISA (enzyme-linked immunoabsorbant assay) or other immunoassay technique well known in the art. A currently preferred, exemplary protocol for an ELISA assay, as well as means for generating morphogen-specific antibody are presented below. Standard protocols for antibody production, Western blot and other immunoassays also are described, for example, in *Molecular Cloning A Laboratory Manual*, Sambrook et al., eds. 1989, Cold Spring Harbor Press, Cold Spring Harbor, N.Y. Standard ELISA technique is described, for example, by Engvall (1980) *Methods Enzymol.* 70: 419–439.

8.1 Morphogen-Specific Antiserum

Polyclonal antibody was prepared as follows. Each rabbit was given a primary immunization of 100 µg/500 µl E. coli-produced OP-1 monomer (amino acids 328–431 in SEQ ID NO:5) in 0.1% SDS mixed with 500 µl Complete Freund's Adjuvant. The antigen was injected subcutaneously at multiple sites on the back and flanks of the animal. The rabbit was boosted after a month in the same manner using incomplete Freund's Adjuvant. Test bleeds are taken from the ear vein seven days later. Two additional boosts and test bleeds were performed at monthly intervals until antibody against OP-1 was detected in the serum using an ELISA assay. Then, the rabbit was boosted monthly with 100 µg of antigen and bled (15 ml per bleed) at days seven and ten after boosting.

8.2 Morphogen-Specific Antibody

Monoclonal antibody specific for a given morphogen was prepared as follows. A mouse was given two injections of *E. coli* produced OP-1 monomer. The first injection contains 100 µg of OP-1 in complete Freund's adjuvant and was given subcutaneously. The second injection contained 50 µg of OP-1 in incomplete adjuvant and was given intraperitoneally. The mouse then received a total of 230 µg of OP-1 (amino acids 307–431 in SEQ ID NO:5) in four intraperitoneal injections at various times over an eight month period. One week prior to fusion, both mice were boosted intraperitoneally with 100 µg of OP-1 (307–431) and 30 µg of the N-terminal peptide (Ser293-Asn309-Cys) conjugated through the added cysteine to bovine serum albumin with SMCC crosslinking agent. This boost was repeated five days (IP), four days (IP), three days (IP) and one day (IV) prior to fusion. The mouse spleen cells then were fused to commercially available myeloma cells at a ratio of 1:1 using PEG 1500 (Boeringer Mannheim, Germany), and the cell fusion plated and screened for OP-1-specific antibodies using OP-1 (307–431) as antigen. The cell fusion and monoclonal screening then were according to standard procedures well described in standard texts widely available in the art e.g., Maniatis et al. *Molecular Cloning A Laboratory Manual*, Cold Spring Harbor Press.

8.3 Morphogen ELISA

1 µg/100 µl of affinity-purified polyclonal rabbit IgG specific for OP-1 was added to each well of a 96-well plate and incubated at 37° C. for an hour. The wells were washed four times with 0.167M sodium borate buffer with 0.15 M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 µl aliquot of an appropriate dilution of each of the test samples of cell culture supernatant was added to each well in triplicate and incubated at 37° C. for 30 min. After incubation, 100 µl biotinylated rabbit anti-OP-1 serum (stock solution is about 1 mg/ml and diluted 1:400 in BSB containing 1% BSA before use) are added to each well and incubated at 37° C. for 30 min. The wells were then washed four times with BSB containing 0.1% Tween 20. 100 µl strepavidin-alkaline (Southern Biotechnology Associates, Inc. Birmingham, Alabama, diluted 1:2000 in BSB containing 0.1% Tween 20 before use) was added to each well and incubated at 37° C. for 30 min. The plates were washed four times with 0.5M Tris buffered Saline (TBS), pH 7.2. 50 µl substrate (ELISA Amplification System Kit, Life Technologies, Inc., Bethesda, Md.) was added to each well incubated at room temperature for 15 min. Then, 50 µl amplifier (from the same amplification system kit) is added and incubated for another 15 min at room temperature. The reaction was stopped by the addition of 50 µl 0.3 M sulphuric acid. The OD at 490 nm of the solution in each well was recorded. To quantitate OP-1 in culture media, an OP-1 standard curve was performed in parallel with the test samples.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A composition comprising:
   (a) a nutrient, trace mineral, or vitamin required for normal metabolism in mammalian tissue; and
   (b) a morphogen capable of being absorbed from the digestive system into the bloodstream, wherein it retains morphogenic activity, said morphogen comprising an acid-stable, protease-resistant dimeric protein that
      (i) induces tissue-specific morphogenesis of at least mammalian bone tissue; and
      (ii) comprises a pair of folded polypeptides, each having an amino acid sequence comprising a conserved cysteine skeleton of approximately 102 amino acids, wherein cysteines occupy relative positions 1, 30, 34, 66, 67, 99, and 101, and wherein at least 70% of amino acids in said skeleton are selected independently from amino acids occupying corresponding positions within the C-terminal seven cysteine domain of human OP-1, residues 38–139 of Seq. ID No. 5, and conservative substitution variants of said amino acids, said morphogen being dispersed in said composition in a dosage sufficient to induce tissue-specific morphogenesis and to protect mammalian tissue from tissue damage or reduced tissue function due to metabolic stress or dysfunction.

2. A composition comprising:
   (a) a nutrient, trace mineral, or vitamin required for normal metabolism in mammalian tissue; and
   (b) a morphogen capable of being absorbed from the digestive system into the bloodstream, wherein it retains morphogenic activity, said morphogen comprising an acid-stable, protease-resistant dimeric protein that
      (i) induces tissue-specific morphogenesis of at least mammalian bone tissue; and
      (ii) comprises a pair of folded polypeptides, each having an amino acid sequence comprising a conserved cysteine skeleton of approximately 102 amino acids, wherein cysteines occupy relative positions 1, 30, 34, 66, 67, 99, and 101, an wherein at least 70% of amino acids in said skeleton are selected independently from amino acids occupying corresponding positions within the C-terminal seven cysteine domain of human OP-1, residues 38–139 of Seq. ID No. 5, and conservative substitution variants said amino acids, said morphogen being dispersed in said composition in a dosage sufficient to induce tissue-specific morphogenesis and to restore the function of senescent or quiescent mammalian tissue or mammalian tissue afflicted with tissue damage or reduced tissue function due to metabolic stress or dysfunction.

3. The composition of claim 1 or 2, wherein said morphogen is associated with a controlled release component, adapted such that the morphogen is released in a controlled manner in the gastrointestinal tract subsequent to passage through the stomach.

4. The composition of claim 1 or 2 adapted for enteral administration.

5. The composition of claim 1 or 2, formulated as a solid.

6. The composition of claim 5, wherein said solid is a tablet, troche or lozenge.

7. The composition of claim 1 or 2 formulated as a liquid.

8. The composition of claim 7, wherein said liquid is a beverage or a syrup.

9. The composition of claim 1 or 2, wherein said morphogen is associated with a morphogen-solubilizing molecule.

10. The composition of claim 9, wherein said molecule is casein or a derivative, salt or analog thereof.

11. The composition of claim 9, wherein said morphogen-solubilizing molecule comprises one or more prodomains selected from the group consisting of human OP-1, mouse OP-1, human OP-2, mouse OP-2, 60A, GDF-1, BMP2A, BMP2B, DPP, Vgl, Vgr-1, BMP3, BMP5, BMP6, and conservative substitution variants of any of the foregoing which retain morphogenic activity.

12. The composition of claim 1 or 2, wherein at least 80% of amino acids within said skeleton are selected independently from amino acids occupying corresponding positions within the C-terminal seven cysteine domain of human OP-1, residues 38–139 of Seq. ID No. 5, and conservative substitution variants of said amino acids.

13. The composition of claim 1 or 2, wherein said skeleton has greater than 60% amino acid sequence identity with the C-terminal seven cysteine domain of human OP-1, residues 38–139 of Seq. ID No. 5.

14. The composition of claim 13, wherein said skeleton has greater than 65% amino acid sequence identity with the C-terminal seven cysteine domain of human OP-1, residues 38–139 of Seq. ID No. 5.

15. The composition of claim 14, wherein said morphogen comprises an acid-stable, protease-resistant dimeric protein comprising a pair of folded polypeptides, each comprising a C-terminal seven cysteine domain of human OP-1, residues 43–139 of Seq. ID No. 5.

16. The composition of claim 1 or 2, wherein said nutrient is selected from the group consisting of proteins, amino acids, carbohydrates, lipids, fatty acids, sugars, nucleosides, and nucleotides.

17. The composition of claims 1 or 2, wherein said mineral is selected from the group consisting of calcium, phosphorus, sodium, potassium, chloride, magnesium, iron, zinc, copper, manganese, and iodine.

18. The composition of claim 1 or 2, wherein said vitamin is selected from the group consisting of vitamin A, vitamin D3, vitamin C, vitamin B1, vitamin B2, vitamin B6, vitamin B12, pantothenic acid, vitamin E, vitamin K1, folic acid and biotin.

19. The composition of claim 1 or 2, wherein said morphogen is present in its pro form.

20. The composition of claim 19, wherein said morphogen is an acid-stable, protease-resistant dimeric protein comprising a pair of folded polypeptides, each comprising a sequence of human pro OP-1, residues 30–431 of Seq. ID No. 17.

21. A composition comprising:
   (a) a nutrient, trace mineral, or vitamin required for normal metabolism in mammalian tissue; and
   (b) a morphogen capable of being absorbed from the digestive system into the bloodstream, wherein it retains morphogenic activity, said morphogen comprising an acid-stable, protease-resistant dimeric protein that
      (i) induces tissue-specific morphogenesis of at least mammalian bone tissue; and
      (ii) comprises a pair of folded polypeptides, each comprising an amino acid sequence defined by Generic Sequence 6, Seq. ID No. 31, said morphogen being dispersed in said composition at a dosage sufficient to induces tissue-specific morphogenesis and to protect mammalian tissue at risk of incurring tissue damage or reduced tissue function, or for treating mammalian tissue afflicted with tissue damage or reduced tissue function due to metabolic stress or dysfunction.

22. The composition of claim 21, wherein said morphogen comprises an acid-stable, protease-resistant dimeric protein comprising a pair of folded polypeptides, each comprising an amino acid sequence defined by OPX, Seq. ID No. 29.

* * * * *